US012594590B2

(12) United States Patent
Quigley et al.

(10) Patent No.: US 12,594,590 B2
(45) Date of Patent: Apr. 7, 2026

(54) DEVICES AND TECHNIQUES RELATING TO LANDFILL GAS EXTRACTION

(71) Applicant: Loci Controls, Inc., Wareham, MA (US)

(72) Inventors: Peter Quigley, Duxbury, MA (US); Ian Martin, Higganum, CT (US); Jack Rowbottom, Swansea, MA (US); Nicole Neff, North Potomac, MD (US)

(73) Assignee: Loci Controls, Inc., Wareham, MA (US)

( * ) Notice: Subject to any disclaimer, the term of this patent is extended or adjusted under 35 U.S.C. 154(b) by 0 days.

(21) Appl. No.: 18/929,312

(22) Filed: Oct. 28, 2024

(65) Prior Publication Data

US 2025/0050395 A1    Feb. 13, 2025

Related U.S. Application Data

(63) Continuation of application No. 18/132,753, filed on Apr. 10, 2023, now Pat. No. 12,162,053, which is a
(Continued)

(51) Int. Cl.
B09C 1/00 (2006.01)
E21B 34/00 (2006.01)
(Continued)

(52) U.S. Cl.
CPC .............. B09C 1/005 (2013.01); E21B 34/00 (2013.01); E21B 43/12 (2013.01); E21B 47/06 (2013.01);
(Continued)

(58) Field of Classification Search
CPC ....... B09C 1/005; E21B 43/12; E21B 49/087; E21B 49/0875; G01N 33/0047
See application file for complete search history.

(56) References Cited

U.S. PATENT DOCUMENTS 3,062,037 A    11/1962  Donner et al.
3,567,387 A     3/1971  Jones
(Continued)

FOREIGN PATENT DOCUMENTS

EP        0 743 515  A1    11/1996
WO    WO 2006/005014 A2     1/2006
(Continued)

OTHER PUBLICATIONS

U.S. Appl. No. 16/927,471, filed Jul. 13, 2020, Quigley et al.
(Continued)

*Primary Examiner* — Catherine Loikith
(74) *Attorney, Agent, or Firm* — Wolf, Greenfield & Sacks, P.C.

(57)    ABSTRACT
Systems and methods for controlling extraction of landfill gas from a landfill via a gas extraction system are provided herein. According to some aspects of the technology, there is provided site-level control methods for globally controlling one or more wells based on one or more characteristics of aggregate landfill gas collected from a plurality of wells at a gas output. According to some aspects of the technology, there is provided well-level control methods for locally controlling a first well based on or more characteristics of landfill gas collected from the first well. According to further aspects of the technology, there is provided hybrid control methods for making adjustments to a respective well based on both site-level and well-level control methods.

20 Claims, 17 Drawing Sheets

Related U.S. Application Data continuation of application No. 16/927,482, filed on Jul. 13, 2020, now Pat. No. 11,623,256.

(51) Int. Cl.
| | |
|---|---|
| *E21B 43/12* | (2006.01) |
| *E21B 47/06* | (2012.01) |
| *E21B 49/08* | (2006.01) |
| *G01N 33/00* | (2006.01) |

(52) U.S. Cl.
CPC ........ *E21B 49/087* (2013.01); *E21B 49/0875* (2020.05); *G01N 33/004* (2013.01); *G01N 33/0044* (2013.01); *G01N 33/0047* (2013.01)

(56) References Cited

U.S. PATENT DOCUMENTS

| | | | |
|---|---|---|---|
| 4,026,355 A | 5/1977 | Johnson et al. | |
| 4,191,541 A | 3/1980 | Jenkins | |
| 4,226,675 A | 10/1980 | Lewis et al. | |
| 4,227,897 A | 10/1980 | Reed | |
| 4,494,380 A | 1/1985 | Cross | |
| 4,499,378 A | 2/1985 | Miyatake et al. | |
| 4,670,148 A | 6/1987 | Schneider | |
| 4,890,672 A | 1/1990 | Hall | |
| 5,063,519 A | 11/1991 | Zison | |
| 5,209,941 A | 5/1993 | Wuest | |
| 5,223,229 A | 6/1993 | Brucker | |
| 5,239,861 A | 8/1993 | Fujita et al. | |
| 5,451,249 A | 9/1995 | Spiegel et al. | |
| 5,458,006 A | 10/1995 | Roqueta | |
| 5,665,314 A | 9/1997 | Berger et al. | |
| 5,681,360 A | 10/1997 | Siwajek et al. | |
| 5,695,641 A | 12/1997 | Cosulich et al. | |
| 5,830,262 A | 11/1998 | Marchini et al. | |
| 6,169,962 B1 | 1/2001 | Brookshire et al. | |
| 6,196,324 B1 | 3/2001 | Giacomino et al. | |
| 6,241,950 B1 | 6/2001 | Veelenturf et al. | |
| 6,399,391 B1 | 6/2002 | Tomlin | |
| 6,591,695 B1 | 7/2003 | Brookshire et al. | |
| 6,595,287 B2 | 7/2003 | Fisher | |
| 6,611,760 B2 | 8/2003 | Bentley et al. | |
| 6,749,368 B2 | 6/2004 | Ankeny et al. | |
| 6,799,477 B2 | 10/2004 | Brookshire et al. | |
| 6,999,883 B1 | 2/2006 | Brady et al. | |
| 7,187,299 B2 | 3/2007 | Kunerth et al. | |
| 7,198,433 B2 | 4/2007 | Augenstein et al. | |
| 7,243,730 B2 | 7/2007 | Casey | |
| 7,273,098 B2 | 9/2007 | Evans et al. | |
| 7,373,976 B2 | 5/2008 | Casey | |
| 7,387,163 B2 | 6/2008 | Seegers et al. | |
| 7,448,828 B2 | 11/2008 | Augenstein et al. | |
| 7,748,450 B2 | 7/2010 | Mundell | |
| 7,866,921 B2 | 1/2011 | Stamoulis | |
| 7,950,464 B2 | 5/2011 | Atencio et al. | |
| 7,972,082 B2 | 7/2011 | Augenstein et al. | |
| 8,047,276 B2 | 11/2011 | Stamoulis | |
| 8,163,242 B2 | 4/2012 | Elkins | |
| 8,168,121 B2 | 5/2012 | Elkins | |
| 8,186,211 B2 | 5/2012 | Boult et al. | |
| 8,840,708 B1 | 9/2014 | Morrow et al. | |
| 8,924,029 B2 | 12/2014 | Nath et al. | |
| 9,062,536 B2 | 6/2015 | Fischer et al. | |
| 10,029,290 B2 | 7/2018 | Campanella et al. | |
| 10,400,560 B2 | 9/2019 | Campanella et al. | |
| 10,408,747 B2 | 9/2019 | Schlueter et al. | |
| 10,449,578 B2 | 10/2019 | Campanella et al. | |
| 10,556,259 B2 | 2/2020 | Campanella et al. | |
| 10,576,514 B2 | 3/2020 | Campanella et al. | |
| 10,576,515 B2 | 3/2020 | Campanella et al. | |
| 10,639,687 B2 | 5/2020 | Campanella et al. | |
| 10,682,678 B2 | 6/2020 | Campanella et al. | |
| 10,705,063 B2 | 7/2020 | Campanella et al. | |
| 10,882,086 B2 | 1/2021 | Quigley et al. | |
| 10,946,420 B2 | 3/2021 | Quigley et al. | |
| 11,007,555 B2 | 5/2021 | Campanella et al. | |
| 11,067,549 B2 | 7/2021 | Campanella et al. | |
| 11,072,006 B2 | 7/2021 | Campanella et al. | |
| 11,084,074 B2 | 8/2021 | Campanella et al. | |
| 11,235,361 B2 | 2/2022 | Quigley et al. | |
| 11,273,473 B2 | 3/2022 | Quigley et al. | |
| 11,484,919 B2 | 11/2022 | Quigley et al. | |
| 11,486,573 B1 | 11/2022 | Siegel | |
| 11,491,521 B2 | 11/2022 | Quigley et al. | |
| 11,602,777 B2 | 3/2023 | Campanella et al. | |
| 11,602,778 B2 | 3/2023 | Campanella et al. | |
| 11,623,256 B2 | 4/2023 | Quigley et al. | |
| 11,845,115 B2 | 12/2023 | Campanella et al. | |
| 11,850,639 B2 | 12/2023 | Campanella et al. | |
| 11,865,594 B2 | 1/2024 | Quigley et al. | |
| 11,872,610 B2 | 1/2024 | Quigley et al. | |
| 11,883,864 B2 | 1/2024 | Quigley et al. | |
| 11,885,784 B2 | 1/2024 | Campanella et al. | |
| 11,977,062 B2 | 5/2024 | Campanella et al. | |
| 12,083,565 B2 | 9/2024 | Quigley et al. | |
| 12,090,532 B2 | 9/2024 | Campanella et al. | |
| 12,151,271 B2 | 11/2024 | Campanella et al. | |
| 12,162,053 B2 | 12/2024 | Quigley et al. | |
| 2001/0005812 A1 | 6/2001 | Brookshire et al. | |
| 2002/0101718 A1 | 8/2002 | Negishi | |
| 2003/0000281 A1 | 1/2003 | Ketler et al. | |
| 2004/0055359 A1 | 3/2004 | Ketler et al. | |
| 2004/0121201 A1 | 6/2004 | Roche et al. | |
| 2006/0034664 A1 | 2/2006 | Augenstein et al. | |
| 2006/0251540 A1 | 11/2006 | Benning et al. | |
| 2007/0224085 A1 | 9/2007 | Tooley | |
| 2007/0225923 A1 | 9/2007 | Tooley | |
| 2007/0254196 A1 | 11/2007 | Richards et al. | |
| 2008/0011248 A1 | 1/2008 | Cutlip et al. | |
| 2008/0127726 A1 | 6/2008 | Elkins | |
| 2009/0136298 A1 | 5/2009 | Augenstein et al. | |
| 2010/0006281 A1 | 1/2010 | DuBrucq | |
| 2010/0310733 A1 | 12/2010 | Hoffman | |
| 2011/0061439 A1 | 3/2011 | Dong et al. | |
| 2011/0061874 A1 | 3/2011 | Stamoulis | |
| 2011/0081586 A1 | 4/2011 | McAlister | |
| 2011/0132104 A1 | 6/2011 | Benson et al. | |
| 2011/0198094 A1 | 8/2011 | Stamoulis | |
| 2011/0231099 A1 | 9/2011 | Elkins | |
| 2011/0272420 A1 | 11/2011 | Landess et al. | |
| 2012/0191349 A1 | 7/2012 | Lenz et al. | |
| 2012/0206715 A1 | 8/2012 | Laub | |
| 2012/0287418 A1 | 11/2012 | Scherer et al. | |
| 2013/0036811 A1 | 2/2013 | Boult | |
| 2013/0180703 A1 | 7/2013 | Colby | |
| 2013/0193325 A1 | 8/2013 | Phillips et al. | |
| 2013/0247647 A1 | 9/2013 | Mahoney et al. | |
| 2013/0334418 A1 | 12/2013 | Cowie et al. | |
| 2014/0023576 A1 | 1/2014 | Yezerets et al. | |
| 2014/0182846 A1 | 7/2014 | Fischer et al. | |
| 2014/0284935 A1 | 9/2014 | Disbennett et al. | |
| 2014/0338878 A1 | 11/2014 | Tessnow | |
| 2015/0000426 A1 | 1/2015 | Rolston et al. | |
| 2015/0168274 A1 | 6/2015 | Sheffield | |
| 2015/0226045 A1 | 8/2015 | Fischer et al. | |
| 2015/0275632 A1 | 10/2015 | Fischer et al. | |
| 2015/0330938 A1 | 11/2015 | Henson et al. | |
| 2015/0354032 A1 | 12/2015 | Yuan et al. | |
| 2015/0362468 A1 | 12/2015 | Gerhold | |
| 2016/0011159 A1 | 1/2016 | Sekiya et al. | |
| 2016/0025696 A1 | 1/2016 | Birks et al. | |
| 2016/0033391 A1 | 2/2016 | Stroganov et al. | |
| 2016/0123946 A1 | 5/2016 | Dufresne | |
| 2016/0169826 A1 | 6/2016 | Youssi et al. | |
| 2016/0209133 A1 | 7/2016 | Hu et al. | |
| 2016/0237007 A1 | 8/2016 | Morrow et al. | |
| 2016/0238494 A1 | 8/2016 | Chrin, II | |
| 2016/0247183 A1 | 8/2016 | Foody | |
| 2016/0287870 A1 | 10/2016 | Yip et al. | |
| 2016/0377457 A1 | 12/2016 | Zhang et al. | |
| 2017/0080762 A1 | 3/2017 | Guinart et al. | |
| 2017/0122065 A1 | 5/2017 | Fischer et al. | |
| 2017/0173505 A1 | 6/2017 | Dhingra et al. | |
| 2017/0176590 A1 | 6/2017 | Sharonov et al. | |

(56)                References Cited

U.S. PATENT DOCUMENTS

| | | |
|---|---|---|
| 2017/0216891 A1 | 8/2017 | Campanella et al. |
| 2017/0216892 A1 | 8/2017 | Campanella et al. |
| 2017/0216893 A1 | 8/2017 | Campanella et al. |
| 2017/0218730 A1 | 8/2017 | Campanella et al. |
| 2017/0218731 A1 | 8/2017 | Campanella et al. |
| 2017/0218732 A1 | 8/2017 | Campanella et al. |
| 2017/0254196 A1 | 9/2017 | Campanella et al. |
| 2017/0254787 A1 | 9/2017 | Campanella et al. |
| 2017/0328750 A1 | 11/2017 | Jehle et al. |
| 2018/0003572 A1 | 1/2018 | Garsd et al. |
| 2018/0003684 A1 | 1/2018 | Kerr |
| 2018/0024202 A1 | 1/2018 | Erickson et al. |
| 2018/0154408 A1 | 6/2018 | Ko et al. |
| 2018/0164137 A1 | 6/2018 | Layher et al. |
| 2018/0171604 A1 | 6/2018 | Kim et al. |
| 2018/0209248 A1 | 7/2018 | Patel et al. |
| 2018/0304323 A1 | 10/2018 | Campanella et al. |
| 2019/0069245 A1 | 2/2019 | Miller et al. |
| 2019/0232346 A1 | 8/2019 | Speer et al. |
| 2019/0277119 A1 | 9/2019 | Campion |
| 2019/0277821 A1 | 9/2019 | Quigley et al. |
| 2020/0086365 A1 | 3/2020 | Campanella et al. |
| 2020/0101504 A1 | 4/2020 | Quigley et al. |
| 2020/0101505 A1 | 4/2020 | Quigley et al. |
| 2020/0130033 A1 | 4/2020 | Campanella et al. |
| 2020/0197990 A1 | 6/2020 | Quigley et al. |
| 2020/0254497 A1 | 8/2020 | Campanella et al. |
| 2020/0306806 A1 | 10/2020 | Quigley et al. |
| 2020/0306807 A1 | 10/2020 | Quigley et al. |
| 2021/0046524 A1 | 2/2021 | Quigley et al. |
| 2021/0178436 A1 | 6/2021 | Quigley et al. |
| 2021/0229142 A1 | 7/2021 | Quigley et al. |
| 2021/0372977 A1 | 12/2021 | Campanella et al. |
| 2022/0008970 A1 | 1/2022 | Quigley et al. |
| 2022/0008971 A1 | 1/2022 | Quigley et al. |
| 2022/0008972 A1 | 1/2022 | Quigley et al. |
| 2022/0008973 A1 | 1/2022 | Quigley et al. |
| 2022/0062959 A1 | 3/2022 | Campanella et al. |
| 2022/0062960 A1 | 3/2022 | Campanella et al. |
| 2023/0114970 A1 | 4/2023 | Quigley et al. |
| 2023/0234112 A1 | 7/2023 | Campanella et al. |
| 2023/0271234 A1 | 8/2023 | Campanella et al. |
| 2023/0302508 A1 | 9/2023 | Campanella et al. |
| 2023/0302509 A1 | 9/2023 | Campanella et al. |
| 2023/0324353 A1 | 10/2023 | Campanella et al. |
| 2024/0017311 A1 | 1/2024 | Campanella et al. |
| 2024/0066572 A1 | 2/2024 | Campanella et al. |
| 2024/0066573 A1 | 2/2024 | Campanella et al. |
| 2024/0100578 A1 | 3/2024 | Campanella et al. |
| 2024/0109110 A1 | 4/2024 | Quigley et al. |
| 2024/0109111 A1 | 4/2024 | Campanella et al. |
| 2024/0316605 A1 | 9/2024 | Campanella et al. |
| 2024/0316606 A1 | 9/2024 | Campanella et al. |
| 2024/0390958 A1 | 11/2024 | Quigley et al. |
| 2024/0390961 A1 | 11/2024 | Campanella et al. |

FOREIGN PATENT DOCUMENTS

| | | |
|---|---|---|
| WO | WO 2015/072989 A1 | 5/2015 |
| WO | WO 2016/010985 A1 | 1/2016 |
| WO | WO 2018/194650 A1 | 10/2018 |
| WO | WO 2020/072457 A1 | 4/2020 |

OTHER PUBLICATIONS

U.S. Appl. No. 16/927,479, filed Jul. 13, 2020, Quigley et al.
U.S. Appl. No. 18/168,983, filed Feb. 14, 2023, Campanella et al.
U.S. Appl. No. 18/327,580, filed Jun. 1, 2023, Campanella et al.
U.S. Appl. No. 18/498,770, filed Oct. 31, 2023, Campanella et al.
U.S. Appl. No. 18/498,869, filed Oct. 31, 2023, Campanella et al.
U.S. Appl. No. 18/526,824, filed Dec. 1, 2023, Quigley et al.
U.S. Appl. No. 18/540,281, filed Dec. 14, 2023, Quigley et al.
U.S. Appl. No. 18/425,421, filed Jan. 29, 2024, Campanella et al.

U.S. Appl. No. 18/733,043, filed Jun. 4, 2024, Campanella et al.
U.S. Appl. No. 18/733,111, filed Jun. 4, 2024, Campanella et al.
U.S. Appl. No. 18/797,136, filed Aug. 7, 2024, Quigley et al.
U.S. Appl. No. 18/796,741, filed Nov. 28, 2024, Quigley et al.
U.S. Appl. No. 18/917,145, filed Oct. 16, 2024, Campanella et al.
PCT/US2017/020196m Jun. 7, 2017, International Search Report and Written Opinion.
PCT/US77/28818, Jul. 10, 2017, Invitation to Pay Additional Fees.
PCT/US77/28818, Sep. 8, 2017, International Search Report and Written Opinion.
PCT/US2019/020251, May 31, 2019, International Search Report and Written Opinion.
EP 17760717.3, Oct. 2, 2019, Extended European Search Report.
PCT/US2019/054013, Dec. 4, 2019, International Search Report and Written Opinion.
EP 17906368.0, Oct. 15, 2020, Extended European Search Report.
PCT/US2021/013850, Jun. 21, 2021, International Search Report and Written Opinion.
PCT/US2021/040653, Nov. 26, 2021, International Search Report and Written Opinion.
EP 17760717.3, Feb. 21, 2022, Communication pursuant to Article 94(3) EPC.
EP 19869105.7, May 23, 2022, Extended European Search Report.
EP 17906368.0, Aug. 4, 2022, Communication pursuant to Article 94(3) EPC.
PCT/US2019/054013, Apr. 15, 2021, International Preliminary Report on Patentability.
PCT/US2021/013850, Aug. 11, 2022, International Preliminary Report on Patentability.
PCT/US2021/040653, Jan. 26, 2023, International Preliminary Report on Patentability.
EP 17906368.0, May 11, 2023, Communication pursuant to Article 94(3) EPC.
EP 21705025.1, Feb. 15, 2024, Communication pursuant to Article 94(3) EPC.
CA 3109081, Dec. 20, 2023, Examiner's Report.
EP 24154125.9, Apr. 30, 2024, Extended European Search Report.
EP 19869105.7, Oct. 31, 2024, Communication pursuant to Article 94(3) EPC.
EP 21763162.1, Nov. 8, 2024, Communication pursuant to Article 94(3) EPC.
International Search Report and Written Opinion for International Application No. PCT/US2017/020196 mailed Jun. 7, 2017.
Invitation to Pay Additional Fees for International Application No. PCT/US17/28818 mailed Jul. 10, 2017.
International Search Report and Written Opinion for International Application No. PCT/US17/28818 mailed Sep. 8, 2017.
International Search Report and Written Opinion for International Application No. PCT/US2019/020251 mailed May 31, 2019.
Extended European Search Report for European Application No. 17760717.3 dated Oct. 2, 2019.
International Search Report and Written Opinion for International Application No. PCT/US2019/054013 mailed Dec. 4, 2019.
Extended European Search Report for European Application No. 17906368.0 dated Oct. 15, 2020.
International Preliminary Report on Patentability for International Application No. PCT/US2019/054013 mailed Apr. 15, 2021.
International Search Report and Written Opinion for International Application No. PCT/US2021/013850 mailed Jun. 21, 2021.
International Search Report and Written Opinion for International Application No. PCT/US2021/040653 mailed Nov. 26, 2021.
Communication pursuant to Article 94(3) EPC for European Application No. 17760717.3 dated Feb. 21, 2022.
Extended European Search Report for European Application No. 19869105.7 dated May 23, 2022.
Communication pursuant to Article 94(3) EPC for European Application No. 17906368.0 dated Aug. 4, 2022.
International Preliminary Report on Patentability for International Application No. PCT/US2021/013850 mailed Aug. 11, 2022.
International Preliminary Report on Patentability for International Application No. PCT/US2021/040653 mailed Jan. 26, 2023.
Communication pursuant to Article 94(3) EPC for European Application No. 17906368.0 dated May 11, 2023.

(56) References Cited

OTHER PUBLICATIONS

Communication pursuant to Article 94(3) EPC for European Application No. 21705025.1 dated Feb. 15, 2024.

Examiner's Report for Canadian Application No. 3109081 dated Dec. 20, 2023.

Extended European Search Report for European Application No. 24154125.9 dated Apr. 30, 2024.

Communication pursuant to Article 94(3) EPC for European Application No. 19869105.7 dated Oct. 31, 2024.

Communication pursuant to Article 94(3) EPC for European Application No. 21763162.1 dated Nov. 8, 2024.

Campanella et al., Designs for Enhanced Reliability and Calibration of Landfill Gas Measurement and Control Devices. Co-pending U.S. Appl. No. 15/464,236, filed Mar. 20, 2017.

Campanella et al., Designs for Enhanced Reliability and Calibration of Landfill Gas Measurement and Control Devices. Co-pending U.S. Appl. No. 15/478,583, filed Apr. 4, 2017.

Campanella et al., Designs for Enhanced Reliability and Calibration of Landfill Gas Measurement and Control Devices. Co-pending U.S. Appl. No. 17/343,317, filed Jun. 9, 2021.

Campanella et al., Designs for Enhanced Reliability and Calibration of Landfill Gas Measurement and Control Devices. Co-pending U.S. Appl. No. 18/327,580, filed Jun. 1, 2023.

Campanella et al., Designs for Enhanced Reliability and Calibration of Landfill Gas Measurement and Control Devices. Co-pending U.S. Appl. No. 18/425,421, filed Jan. 29, 2024.

Campanella et al., Devices and Techniques Relating to Landfill Gas Extraction. Co-pending U.S. Appl. No. 14/532,807, filed Nov. 4, 2014.

Campanella et al., Devices and Techniques Relating to Landfill Gas Extraction. Co-pending U.S. Appl. No. 15/456,936, filed Mar. 13, 2017.

Campanella et al., Devices and Techniques Relating to Landfill Gas Extraction. Co-pending U.S. Appl. No. 15/456,982, filed Mar. 13, 2017.

Campanella et al., Devices and Techniques Relating to Landfill Gas Extraction. Co-pending U.S. Appl. No. 15/493,174, filed Apr. 21, 2017.

Campanella et al., Devices and Techniques Relating to Landfill Gas Extraction. Co-pending U.S. Appl. No. 15/493,184, filed Apr. 21, 2017.

Campanella et al., Devices and Techniques Relating to Landfill Gas Extraction. Co-pending U.S. Appl. No. 15/493,201, filed Apr. 21, 2017.

Campanella et al., Devices and Techniques Relating to Landfill Gas Extraction. Co-pending U.S. Appl. No. 16/024,085, filed Jun. 29, 2018.

Campanella et al., Devices and Techniques Relating to Landfill Gas Extraction. Co-pending U.S. Appl. No. 16/694,745, filed Nov. 25, 2019.

Campanella et al., Devices and Techniques Relating to Landfill Gas Extraction. Co-pending U.S. Appl. No. 16/726,232, filed Dec. 23, 2019.

Campanella et al., Devices and Techniques Relating to Landfill Gas Extraction. Co-pending U.S. Appl. No. 16/745,892, filed Jan. 17, 2020.

Campanella et al., Devices and Techniques Relating to Landfill Gas Extraction. Co-pending U.S. Appl. No. 16/831,131, filed Mar. 26, 2020.

Campanella et al., Devices and Techniques Relating to Landfill Gas Extraction. Co-pending U.S. Appl. No. 17/369,318, filed Jul. 7, 2021.

Campanella et al., Devices and Techniques Relating to Landfill Gas Extraction. Co-pending U.S. Appl. No. 17/369,395, filed Jul. 7, 2021.

Campanella et al., Devices and Techniques Relating to Landfill Gas Extraction. Co-pending U.S. Appl. No. 18/158,742, filed Jan. 24, 2023.

Campanella et al., Devices and Techniques Relating to Landfill Gas Extraction. Co-pending U.S. Appl. No. 18/168,983, filed Feb. 14, 2023.

Campanella et al., Devices and Techniques Relating to Landfill Gas Extraction. Co-pending U.S. Appl. No. 18/327,516, filed Jun. 1, 2023.

Campanella et al., Devices and Techniques Relating to Landfill Gas Extraction. Co-pending U.S. Appl. No. 18/327,638, filed Jun. 1, 2023.

Campanella et al., Devices and Techniques Relating to Landfill Gas Extraction. Co-pending U.S. Appl. No. 18/327,694, filed Jun. 1, 2023.

Campanella et al., Devices and Techniques Relating to Landfill Gas Extraction. Co-pending U.S. Appl. No. 18/498,770, filed Oct. 31, 2023.

Campanella et al., Devices and Techniques Relating to Landfill Gas Extraction. Co-pending U.S. Appl. No. 18/498,869, filed Oct. 31, 2023.

Quigley et al., Automated Compliance Measurement and Control for Landfill Gas Extraction Systems. Co-pending U.S. Appl. No. 17/152,252, filed Jan. 19, 2021.

Quigley et al., Automated Compliance Measurement and Control for Landfill Gas Extraction Systems. Co-pending U.S. Appl. No. 18/540,281, filed Dec. 14, 2023.

Quigley et al., Devices and Techniques Relating to Landfill Gas Extraction. Co-pending U.S. Appl. No. 16/927,471, filed Jul. 13, 2020.

Quigley et al., Devices and Techniques Relating to Landfill Gas Extraction. Co-pending U.S. Appl. No. 16/927,479, filed Jul. 13, 2020.

Quigley et al., Devices and Techniques Relating to Landfill Gas Extraction. Co-pending U.S. Appl. No. 16/927,482, filed Jul. 13, 2020.

Quigley et al., Devices and Techniques Relating to Landfill Gas Extraction. Co-pending U.S. Appl. No. 16/927,488, filed Jul. 13, 2020.

Quigley et al., Devices and Techniques Relating to Landfill Gas Extraction. Co-pending U.S. Appl. No. 18/132,753, filed Apr. 10, 2023.

Quigley et al., Landfill Gas Extraction Control System. Co-pending U.S. Appl. No. 16/290,387, filed Mar. 1, 2019.

Quigley et al., Landfill Gas Extraction Control System. Co-pending U.S. Appl. No. 17/167,539, filed Feb. 4, 2021.

Quigley et al., Landfill Gas Extraction Control System. Co-pending U.S. Appl. No. 18/526,824, filed Dec. 1, 2023.

Quigley et al., Landfill Gas Extraction Systems and Methods. Co-pending U.S. Appl. No. 16/589,372, filed Oct. 1, 2019.

Quigley et al., Landfill Gas Extraction Systems and Methods. Co-pending U.S. Appl. No. 16/589,391, filed Oct. 1, 2019.

Quigley et al., Landfill Gas Extraction Systems and Methods. Co-pending U.S. Appl. No. 16/901,405, filed Jun. 15, 2020.

Quigley et al., Landfill Gas Extraction Systems and Methods. Co-pending U.S. Appl. No. 16/901,430, filed Jun. 15, 2020.

Quigley et al., Landfill Gas Extraction Systems and Methods. Co-pending U.S. Appl. No. 17/086,987, filed Nov. 2, 2020.

Quigley et al., Landfill Gas Extraction Systems and Methods. Co-pending U.S. Appl. No. 17/959,446, filed Oct. 4, 2022.

Campanella et al., Devices and Techniques Relating to Landfill Gas Extraction. Co-pending U.S. Appl. No. 18/733,043, filed Jun. 4, 2024.

Campanella et al., Devices and Techniques Relating to Landfill Gas Extraction. Co-pending U.S. Appl. No. 18/733,111, filed Jun. 4, 2024.

Quigley et al., Landfill Gas Extraction Systems and Methods. Co-pending U.S. Appl. No. 18/797,136, filed Aug. 7, 2024.

Quigley et al., Devices and Techniques Relating to Landfill Gas Extraction. Co-pending U.S. Appl. No. 18/796,741, filed Aug. 7, 2024.

Campanella et al., Devices and Techniques Relating to Landfill Gas Extraction. Co-pending U.S. Appl. No. 18/917,145, filed Oct. 16, 2024.

(56)                    References Cited

OTHER PUBLICATIONS

Quigley et al., Devices and Techniques Relating to Landfill Gas Extraction. Co-pending U.S. Appl. No. 18/929,312, filed Oct. 28, 2024.

[No Author Listed], 40 CFR 60.755. US Code of Federal Regulations. Jul. 2017:243-45. https://www.govinfo.gov/content/pkg/CFR-2017-title40-vol8/pdf/CFR-2017-title40-vol8-sec60-755.pdf (Last accessed Feb. 27, 2024).

[No Author Listed], 50% CH4, 35% CO2, 15% N2. Instrument Depot. 2015. http://www.instrumentdepot.com/50-methane-35-carbon-dioxide-15-nitrogen-c-1_27_472.html.

[No Author Listed], Cloud-Based Wellwatcher Analytics Platform Offers 24/7/365 Visibility on Landfill Gas-Collection Systems. Tech Note. Loci Controls. Nov. 2016. 1 page.

[No Author Listed], Green House Gas Emissions Reduction with Loci Controls. YouTube. Jun. 25, 2021. https://www.youtube.com/watch?v=-reQosq7TJw&t=50s [last accessed Nov. 10, 2022]. 3 pages.

[No Author Listed], Increase Landfill Gas Collection By Up To 30%. Tech Note. Loci Controls. Oct. 2016. 1 page.

[No Author Listed], Loci—EPP RNG Works Presentation Preview. YouTube. Sep. 5, 2019. https://www.youtube.com/watch?v=33_WcvJxidY&t=128s [last accessed Nov. 10, 2022]. 3 pages.

[No Author Listed], Loci Controller Combines Active Flow Control With 24/7/365 Real-Time Gas-Composition Analysis to Maximize Landfill Gas Extraction. Tech Note. Loci Controls. Nov. 2016. 1 page.

[No Author Listed], Loci Controls—Automated Landfill Wellfield Tuning to External Variables. YouTube. Mar. 5, 2021. https://www.youtube.com/watch?v=AdQRep0x3XM&t=82s [last accessed Nov. 10, 2022]. 4 pages.

[No Author Listed], Loci Controls—Automated Wellfield Tuning. YouTube. Mar. 5, 2021. https://www.youtube.com/watch?v=IbdMx2CCKbc&t=100s [last accessed Nov. 10, 2022]. 5 pages.

[No Author Listed], Loci Controls, Inc Expands Number of Proprietary Advanced Technologies, Company Adds Flo-Wing Meter Measurement System to Its Roster of Issued Patents. News Release. Apr. 6, 2021. https://www.locicontrols.com/perch/resources/loci-expands-advanced-technologies-with-flo-wing-1.pdf [Last accessed Nov. 10, 2022]. 2 pages.

[No Author Listed], Loci Controls, Inc. Achieves Milestone with Exceptional Safety Record. News Release. Oct. 20, 2021. https://www.locicontrols.com/perch/resources/loci-achieves-exceptional-safety-record-1.pdf [Last accessed Nov. 10, 2022]. 2 pages.

[No Author Listed], Loci Controls, Inc. and American Carbon Registry Develop New Carbon Market Incentives to Reduce Methane Emissions from Large Landfills. News Release. Jun. 3, 2021. https://www.locicontrols.com/perch/resources/acr-approves-loci-methodology-1.pdf [Last accessed Nov. 10, 2022]. 3 pages.

[No Author Listed], Loci Sentry Utilizes Passive Flow and Gas-Composition Monitoring in Conjunction With Loci Controller and Wellwatcher Analytics to Maximize Landfill Gas Collection. Tech Note. Loci Controls. Nov. 2016. 1 page.

[No Author Listed], Methacontrol® Optimizing landfill gas recovery. Oct. 9, 2013. http://www.veolia.com/en/veolia-group/media/news/methacontrol-r. 1 page.

Bieker et al., Real-Time Production Optimization of Offshore Oil and Gas Production Systems: A Technology Survey. SPE International. 2006. 8 pages.

Bingham et al., Automated Landfill Gas Collection Increases Landfill Gas Flow and Quality at Oklahoma City Landfill. Loci Controls. Mar. 7, 2018. 14 pages. https://locicontrols.com/perch/resources/aria-white-paper-022119-1.pdf [Last accessed Nov. 10, 2022].

Caton et al., Automated Landfill Gas Collection Increases Uptime and Revenue for Landfill in Lawrence, KS. Loci Controls. 2019. 22 pages. [Last accessed May 11, 2022].

Collins et al., Web-based monitoring of year-length deployments of autonomous gas sensing platforms on landfill sites. 2011 IEEE Sensors Proceedings. 2011:1620-3.

Fay et al., Remote Real-Time Monitoring of Subsurface Landfill Gas Migration. Sensors. 2011;11(7):6603-29.

Messics et al., Automated Landfill Gas Collection Improves Operations and Increases Revenue for one of the Largest High-BTU Landfill-Gas-to-Energy Sites in the US. Technical Paper. Sep. 10, 2019. 10 pages.

Office Communication mailed Aug. 1, 2023 for U.S. Appl. No. 16/927,471.

Office Communication mailed Aug. 1, 2023 for U.S. Appl. No. 16/927,479.

Office Communication mailed Aug. 25, 2022 for U.S. Appl. No. 17/152,252.

Office Communication mailed Feb. 2, 2023 for U.S. Appl. No. 17/959,446.

Office Communication mailed May 12, 2022 for U.S. Appl. No. 16/927,479.

Office Communication mailed May 3, 2022 for U.S. Appl. No. 16/927,471.

Quigley, Loci Controls, Inc. (Fall River, MA), and Enerdyne Power Systems Inc., ("Enerdyne", Charlotte, NC). Loci Controls. Aug. 2019. 2 pages. [Last accessed May 11, 2022].

Response to Office Action filed Aug. 1, 2023 for U.S. Appl. No. 17/959,446.

Response to Office Action filed Jan. 2, 2024 for U.S. Appl. No. 16/927,471.

Response to Office Action filed Jan. 2, 2024 for U.S. Appl. No. 16/927,479.

Response to Office Action filed Nov. 2, 2022 for U.S. Appl. No. 16/927,471.

Response to Office Action filed Nov. 2, 2022 for U.S. Appl. No. 16/927,479.

Response to Office Action filed Nov. 22, 2022 for U.S. Appl. No. 17/152,252.

Xu et al., Impact of changes in barometric pressure on landfill methane emission. AGU Publications. Jul. 10, 2014. 17 pages.

1

DEVICES AND TECHNIQUES RELATING TO LANDFILL GAS EXTRACTION

CROSS-REFERENCE TO RELATED APPLICATIONS

This Application is a continuation of and claims priority under 35 U.S.C. § 120 to U.S. patent application Ser. No. 18/132,753, titled "Devices and Techniques Relating to Landfill Gas Extraction," filed Apr. 10, 2023, which is a continuation of and claims priority under 35 U.S.C. § 120 to U.S. patent application Ser. No. 16/927,482, titled "Devices and Techniques Relating to Landfill Gas Extraction," filed Jul. 13, 2020, which is hereby incorporated by reference herein in its entirety.

FEDERALLY SPONSORED RESEARCH

This invention was made with government support under SBIR Phase II Award No. 1632439 and SBIR Phase 1B Award No. 1520346, awarded by the National Science Foundation. The government has certain rights in the invention.

BACKGROUND

Landfills typically produce landfill gas as a result of decomposition processes occurring in the waste, and methane is often a component of this landfill gas. In order to reduce emissions of methane and other contaminants in landfill gas, the landfill sites are typically capped with a layer of cover material and gas extraction systems are installed to pull landfill gas out before it can penetrate the cover layer and escape. At larger sites, these gas extraction systems can consist of a plurality of vertical and horizontal wells drilled into the landfill, which are connected with piping to one or more vacuum sources. The cover layer prevents gas from freely escaping, while the vacuum in the extraction wells pulls landfill gas into the collection system. A conventional landfill gas extraction well typically has a manual valve that adjusts the localized vacuum pressure in that well, as well as a set of ports for sampling the gas characteristics with a portable gas analyzer. Landfill gas is most often disposed of in a flare, processed for direct use, or used to power electricity generation equipment (such as generators or gas turbines).

SUMMARY

Some embodiments are directed to a method for controlling extraction of landfill gas from a landfill via a gas extraction system, the gas extraction system comprising well piping for coupling a plurality of wells to a gas output, the method comprising: obtaining, at the gas output, a measure of nitrogen concentration of landfill gas collected from at least some of the plurality of wells; determining whether the measure of nitrogen concentration of the landfill gas collected from the at least some of the plurality of wells is outside of a global range for nitrogen concentration; when it is determined that the measure of nitrogen concentration of the landfill gas collected from the at least some of the plurality of wells is outside of the global range for nitrogen concentration: determining whether a measure of methane concentration of landfill gas collected from a first well of the at least some of the plurality of wells is outside of a local range for methane concentration; and when it is determined that the measure of methane concentration of landfill gas collected from the first well is outside of the local range for methane concentration, adjusting a flow rate of landfill gas being extracted from the first well.

Some embodiments are directed to a system for controlling extraction of landfill gas from a landfill via a gas extraction system, the gas extraction system comprising well piping for coupling a plurality of wells to a gas output, the system comprising: at least one controller configured to: obtain, at the gas output, a measure of nitrogen concentration of landfill gas collected from at least some of the plurality of wells; determine whether the measure of nitrogen concentration of the landfill gas collected from the at least some of the plurality of wells is outside of a global range for nitrogen concentration; when it is determined that the measure of nitrogen concentration of the landfill gas collected from the at least some of the plurality of wells is outside of the global range for nitrogen concentration: determine whether a measure of methane concentration of landfill gas collected from a first well of the at least some of the plurality of wells is outside of a local range for methane concentration; and when it is determined that the measure of methane concentration of landfill gas collected from the first well is outside of the local range for methane concentration, adjusting a flow rate of landfill gas being extracted from the first well.

Some embodiments are directed to at least one non-transitory computer-readable storage medium having instructions encoded thereon, that, when executed by at least one controller, cause the at least one controller to perform a method for controlling extraction of landfill gas from a landfill via a gas extraction system, the gas extraction system comprising well piping for coupling a plurality of wells to a gas output, the method comprising: obtaining, at the gas output, a measure of nitrogen concentration of landfill gas collected from at least some of the plurality of wells; determining whether the measure of nitrogen concentration of the landfill gas collected from the at least some of the plurality of wells is outside of a global range for nitrogen concentration; when it is determined that the measure of nitrogen concentration of the landfill gas collected from the at least some of the plurality of wells is outside of the global range for nitrogen concentration: determining whether a measure of methane concentration of landfill gas collected from a first well of the at least some of the plurality of wells is outside of a local range for methane concentration; and when it is determined that the measure of methane concentration of landfill gas collected from the first well is outside of the local range for methane concentration, adjusting a flow rate of landfill gas being extracted from the first well.

BRIEF DESCRIPTION OF THE DRAWINGS

Various aspects and embodiments will be described with reference to the following figures. It should be appreciated that the figures are not necessarily drawn to scale. For purposes of clarity, not every component may be labeled in every drawing. In the drawings.

DETAILED DESCRIPTION

Figure 1:
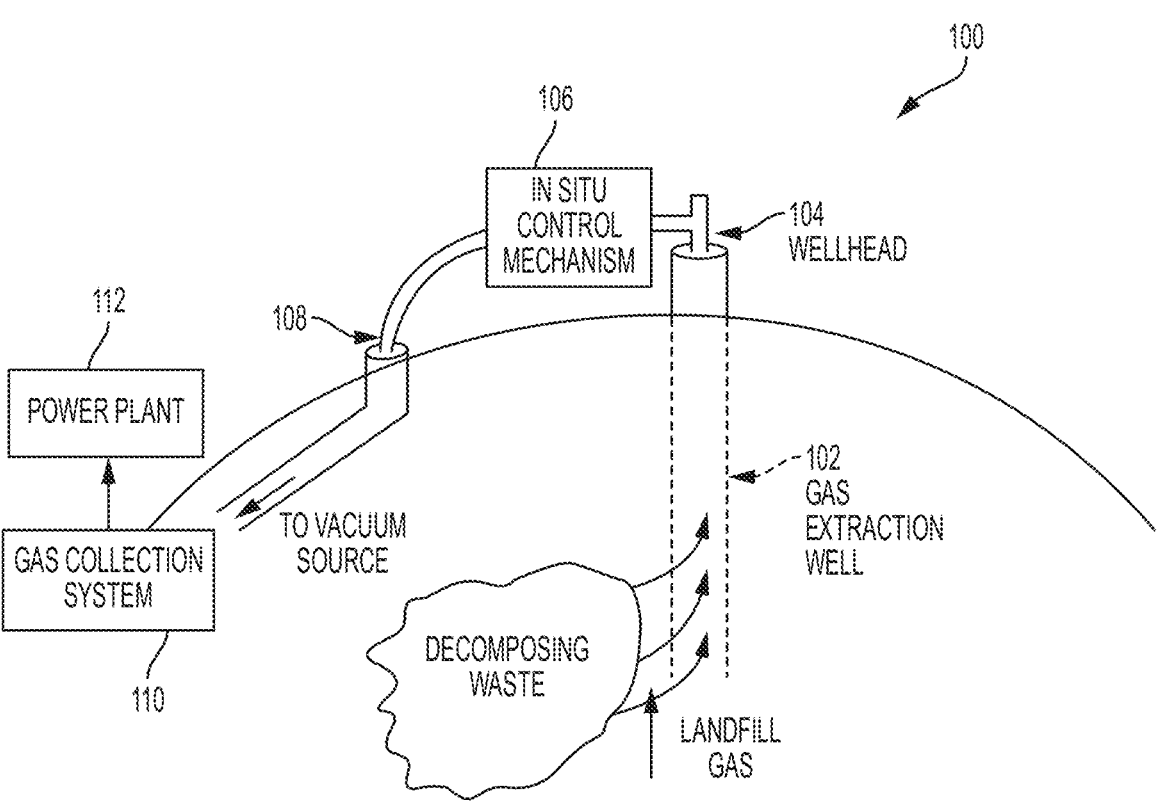
FIG. 1 is a sketch illustrating a landfill gas extraction system, according to some embodiments.

Conventional techniques for controlling extraction of landfill gas are sometimes imprecise and inefficient. When such techniques are used, the gas extracted from a landfill may not have the desired properties (e.g., the energy content of the extracted gas may be lower than a target energy content, the composition of the extracted gas may differ from a target composition, etc.). In some cases, conventional techniques may even be counter-productive (e.g., such techniques may destroy some or all of the bacteria that convert decomposing waste into methane, thereby reducing the energy content of the landfill gas, or may result in emission of high levels of methane into the atmosphere, or worse yet, cause fires to break out deep within the landfill that are near impossible to extinguish).

The inventors have recognized that controlling extraction of landfill gas based on global (landfill site-level) and local (well-level) control schemes may overcome at least some of the deficiencies of conventional landfill gas extraction techniques and result in an overall improvement in landfill management. For example, controlling extraction of landfill gas based on the composition of aggregate landfill gas collected from a plurality of wells may allow for increased flexibility in operation of individual wells (e.g., by permitting one well to compensate for the poor landfill gas quality of another well). In addition, the inventors have recognized that combining site-level (global) control schemes with well-level (local) control schemes allows for concurrent monitoring of aggregate gas quality and fine tuning of individual wells to prevent undesirable conditions from occurring at individual wells (e.g., emission of bad odors, harmful greenhouse gasses and/or creation of underground fires) while optimizing the quality of aggregate gas collected from a plurality of gas extraction wells.

As described above, conventional techniques for controlling extraction of landfill gas may result in extraction of landfill gas having a composition that is different from a target composition. Accordingly, the inventors have developed techniques for controlling extraction of landfill gas such that the concentration of each of one or more constituent gases is in a respective target range. For example, some of the techniques described herein may be used to control extraction of landfill gas so that the concentration of methane in the landfill gas being extracted is within a target range (e.g., within 45-55% by volume).

In some embodiments, techniques for site level control of landfill gas extraction comprise determining whether to adjust a flow rate of one or more wells based on a concentration of a constituent gas in landfill gas collected from multiple wells. When it is determined to adjust the flow rate of one or more wells, the method may determine which individual wells to adjust based on concentrations of a constituent gas in landfill gas collected from respective wells (e.g., by determining to adjust respective wells having a concentration of a constituent gas above or below a threshold). Therefore, the methods for site level control of landfill gas extraction described herein may allow for targeting individual wells determined to have the "best" or "worst" performance, and adjusting those wells accordingly.

Accordingly, in some embodiments, the techniques developed by the inventors for controlling extraction of landfill gas via a gas extraction system having well piping for coupling a plurality of wells to a gas output may comprise: (1) obtaining, at the gas output a measure of concentration of a constituent gas (e.g., oxygen, nitrogen) in landfill gas collected from at least some of the plurality of wells; (2) determining whether the measure of concentration of the constituent gas (e.g., oxygen, nitrogen, methane) in the landfill gas collected from the at least some of the plurality of wells is outside a global range for the constituent gas (e.g., 0-2.5% for oxygen concentration, 0-2.5% for nitrogen concentration, 45-55% for methane concentration); (3) when it is determined that the measure of concentration of the constituent gas in the landfill gas collected from the at least some of the plurality of wells is outside the global range; (4) determining whether a measure of a constituent gas (e.g., oxygen, balance gas, methane) in landfill gas collected from a first well of the at least some of the plurality of wells is outside of a local range for the constituent gas; and (5) when it is determined that the measure of concentration of the constituent gas in landfill gas collected from the first well is outside of the local range for the constituent gas (e.g., 0-5% for oxygen concentration, 0-5% for balance gas concentration, 35%-65% for methane concentration), adjusting a flow rate of landfill gas being extracted from the first well (e.g., by changing a degree to which a valve of the first well is open).

In some embodiments, the techniques further include, when it is determined that the measure of concentration of the constituent gas collected from the at least some of the plurality of wells is outside the global range for the constituent gas: (1) determining whether a measure of a concentration of a constituent gas (e.g., oxygen, balance gas, methane) in landfill gas collected from a second well of the at least some of the plurality of wells is outside of the local range for the constituent gas; and (2) when it is determined that the measure of the constituent gas in landfill gas collected from the second well is outside of the local range for the constituent gas, adjusting a flow rate of landfill gas being extracted from the second well.

In some embodiments, the constituent gas in the landfill gas collected from the plurality of wells is oxygen. In such embodiments, an upper endpoint (e.g., threshold) of the global range may be 0.2% oxygen or less and a lower endpoint (e.g., threshold) of the global range may be 0% oxygen or more. In such embodiments, the constituent gas in landfill gas collected from the first well may be oxygen, an upper endpoint of the local range may be 1% oxygen or less and a lower endpoint of the local range is 0% oxygen or less. In some embodiments, an upper endpoint of the global range is less than an upper endpoint of the local range.

In some embodiments, the constituent gas in the landfill gas collected from the plurality of wells is nitrogen. In such embodiments, an upper endpoint (e.g., threshold) of the global range may be 5% nitrogen or less and a lower endpoint (e.g., threshold) of the global range may be 0% nitrogen or more. In such embodiments, the constituent gas in landfill gas collected from the first well may be balance gas, an upper endpoint of the local range may be 5% balance gas or more, and a lower endpoint of the local range may be 0% balance gas or more. In other embodiments, the constituent gas in landfill gas collected from the first well may be methane, an upper endpoint of the local range may be 65% methane or less, and a lower endpoint of the local range may be 30% methane or more.

In some embodiments, the method further comprises (1) determining a scaling factor by which to proportionally adjust a degree to which a valve of the first well is opened or closed; and (2) adjusting the flow rate of the landfill gas being extracted from the first well according to the scaling factor. In some embodiments, the scaling factor may be based at least in part on a difference between the measure of concentration of the constituent gas in the landfill gas collected from the first well and a target concentration. In some embodiments, the scaling factor may be based at least in part on at least one characteristic of the first well, for example, a sensitivity of the composition of the landfill gas being extracted from the first well to a change in flow rate (e.g., due to a ground cover in a region at least partially encompassing the first well).

In some embodiments, the constituent gas in the landfill gas collected from the first well is oxygen, and determining whether the oxygen concentration is outside of the local range for oxygen concentration comprises (1) determining whether the measure of oxygen concentration is greater than an upper endpoint (e.g., threshold) of the local range or less than a lower endpoint (e.g., threshold) of the local range; (2) decreasing the flow rate of the first well when the measure of oxygen concentration is greater than the upper endpoint; and (3) increasing the flow rate of the first well when the measure of oxygen concentration is less than the lower endpoint.

In some embodiments, the constituent gas in the landfill gas collected from the first well is balance gas, and determining whether the balance gas concentration is outside of the local range for oxygen concentration comprises (1) determining whether the measure of balance gas concentration is greater than an upper endpoint (e.g., threshold) of the local range or less than a lower endpoint (e.g., threshold) of the local range; (2) decreasing the flow rate of the first well when the measure of balance gas concentration is greater than the upper endpoint; and (3) increasing the flow rate of the first well when the measure of balance gas concentration is less than the lower endpoint.

In some embodiments, the constituent gas in the landfill gas collected from the first well is methane, and determining whether the methane concentration is outside of the local range for methane concentration comprises (1) determining whether the measure of methane concentration is greater than an upper endpoint (e.g., threshold) of the local range or less than a lower endpoint (e.g., threshold) of the local range; (2) increasing the flow rate of the first well when the measure of methane concentration is greater than the upper endpoint; and (3) decreasing the flow rate of the first well when the measure of methane concentration is less than the lower endpoint.

In some embodiments, the method further comprises, before increasing the flow rate of landfill gas being extracted from the first well (1) determining whether a measure of a characteristic of the landfill gas collected from the first well (e.g., carbon dioxide concentration, hydrogen sulfide concentration, flow rate) is less than a threshold; and (2) increasing the flow rate of the landfill gas being extracted from the first well when the measure of the characteristic is less than the threshold.

In some embodiments, the method further comprises (1) obtaining, from at least one sensor configured to measure landfill gas pressure in the well piping at a location upstream of a valve of the first well, a measure of landfill gas pressure at the location upstream of the valve; (2) before obtaining the measure of concentration of the constituent gas in the landfill gas collected from the first well, determining whether the measure of landfill gas pressure at the location upstream of the valve is less than a first threshold pressure (e.g., an atmospheric pressure in a region of the landfill having the first well, a negative value relative to atmospheric pressure); and (3) obtaining the measure of the concentration of the constituent gas when it is determined that the measure of landfill gas pressure is less than the first threshold pressure.

In some embodiments, the method further comprises (1) obtaining, from at least one sensor configured to measure landfill gas pressure in the well piping at a location upstream of a valve of the first well, a measure of landfill gas pressure at the location upstream of the valve; (2) before adjusting the flow rate of landfill gas being extracted from the first well, determining whether the measure of landfill gas pressure at the location upstream of the valve is less than a first threshold pressure (e.g., atmospheric pressure, a negative value relative to atmospheric pressure); and (3) when it is determined that the measure of landfill gas pressure at the location upstream of the valve is less than the first threshold pressure, adjusting the flow rate of the landfill gas being extracted from the first well.

In some embodiments, the methods described herein may be performed sequentially. For example, after determining whether the measure of concentration of the constituent gas is outside of the global range, the method may further comprise determining whether measure of a second characteristic of the landfill gas being extracted from the at least some of the plurality of wells is outside of a global range for the second characteristic. For example, in some embodiments, it may first be determined whether a measure of oxygen concentration is outside of a global range for oxygen concentration and it may subsequently be determined whether a measure of nitrogen concentration and/or energy content of the landfill gas collected from the at least some of the plurality of wells is outside of a global range for nitrogen concentration and/or energy content. In some embodiments, it may first be determined whether a measure of nitrogen concentration is outside of a global range for nitrogen concentration and it may subsequently be determined whether a measure of oxygen concentration and/or energy content of the landfill gas collected from the at least some of the plurality of wells is outside of a global range for oxygen concentration and/or energy content.

According to aspects of the technology described herein, methods of performing hybrid control of landfill gas extraction are provided. In some embodiments, a method for controlling extraction of landfill gas from a landfill via a gas extraction system having well piping for coupling a plurality of wells to a gas output comprises: (1) performing a global control method comprising: (a) obtaining, at the gas output, a measure of a concentration of at least one constituent gas (e.g., methane, oxygen, nitrogen) in landfill gas collected from at least some of the plurality of the wells including a first well and a second well; (b) determining, for one or more wells of the at least some of the plurality of wells and including the first well, whether to adjust respective flow rates of landfill gas being extracted from the one or more wells based at least in part on the measure of concentration of the at least one constituent gas (e.g., based on the concentration of the at least one constituent gas, based on an energy content of the landfill gas collected from the at least some of the plurality of wells) (e.g., by determining whether the measure of concentration of the constituent gas is outside of a global range and subsequently whether a measure of concentration of at least one constituent gas in landfill gas collected from the first well is outside of a local range); and (c) when it is determined to adjust the flow rate of landfill gas being extracted from the first well, adjusting the flow rate of the first well; and (2) performing a local control method comprising: (a) obtaining a measure of a concentration of at least one constituent gas (e.g., oxygen, methane, balance gas) in the landfill gas collected from the first well; (b) determining, based on the concentration of the at least one constituent gas in the landfill gas collected from the first well, whether to adjust the flow rate of the first well (e.g., by determining whether the measure of concentration of the constituent gas is outside of a local range, is different from a target concentration, is greater than an upper threshold, is less than a lower threshold); and (c) when it is determined to adjust the flow rate of the first well, adjusting the flow rate of the first well.

In some embodiments, the global control method and the local control method may be performed at first and second frequencies. For example, in some embodiments, the local control method may be performed at least once per hour. In some embodiments, the global control method may be performed no more than once per day. In some embodiments, the local control method is performed more frequently than the global control method.

In some embodiments, the method further comprises performing a second local control method comprising: (a) obtaining a measure of a concentration of the at least one constituent gas in landfill gas collected from the second well; (b) determining, based on the concentration of the at least one constituent gas in landfill gas collected from the second well, whether to adjust the flow rate of the second well; and (c) when it is determined to adjust the flow rate of the second well, adjusting the flow rate of the second well.

In some embodiments, the method further comprises before increasing the flow rate of landfill gas being extracted from the first well (1) determining whether a measure of a characteristic of the landfill gas collected from the first well (e.g., carbon dioxide concentration, hydrogen sulfide concentration, flow rate) is less than a threshold; and (2) increasing the flow rate of the landfill gas being extracted from the first well when the measure of the characteristic is less than the threshold.

In some embodiments, the method further comprises (1) determining a scaling factor by which to adjust a degree to which a valve of the first well is opened or closed; and (2) adjusting the flow rate of the landfill gas being extracted from the first well according to the scaling factor. In some embodiments, the scaling factor may be based at least in part on a difference between the measure of concentration of the constituent gas in the landfill gas collected from the first well and a target concentration. In some embodiments, the scaling factor may be based at least in part on at least one characteristic of the first well, for example, a sensitivity of the composition of the landfill gas being extracted from the first well to a change in flow rate (e.g., due to a ground cover in a region at least partially encompassing the first well).

According to some aspects of the technology, one or more systems may be provided having at least one controller configured to perform one or more of the methods described herein. According to some aspects of the technology, one or more non-transitory computer-readable storage media are provided herein, having executable instructions encoded thereon, that, when executed by at least one controller, cause the at least one controller to perform one or more of the methods described herein.

The aspects and embodiments described above, as well as additional aspects and embodiments, are described further below. These aspects and/or embodiments may be used individually, all together, or in any combination, as the application is not limited in this respect.

Example Systems for Landfill Gas Extraction

Figure 5:
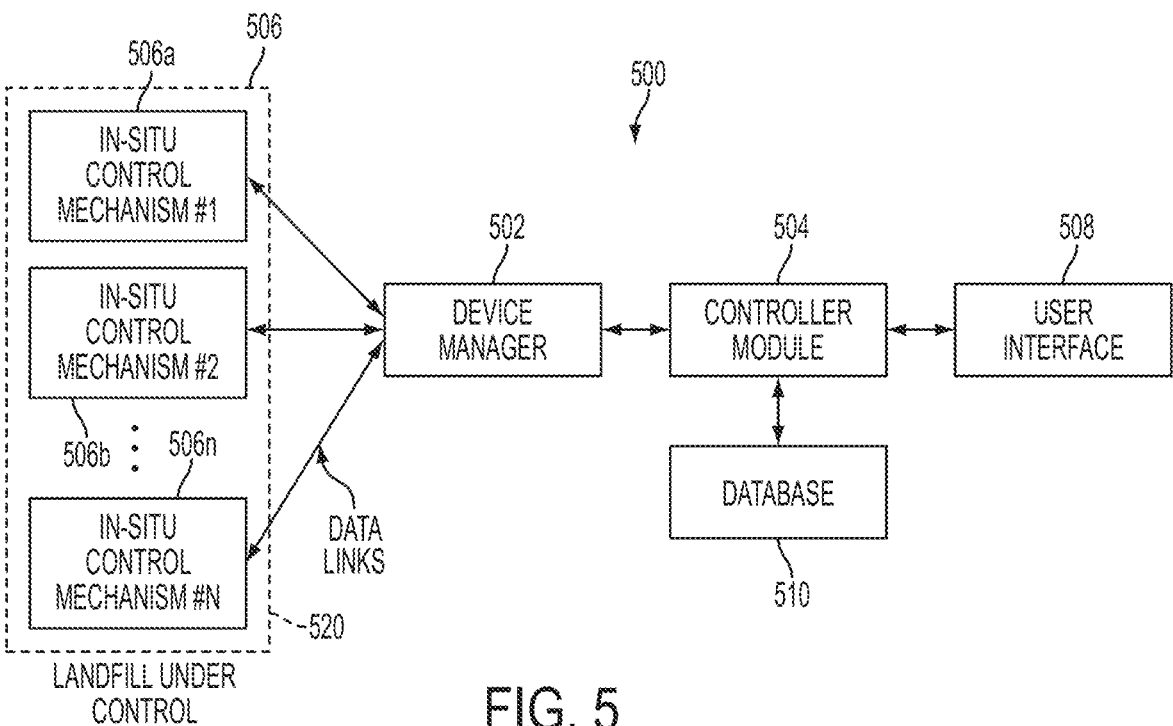
FIG. 5 is a block diagram illustrating an example of a control system for controlling landfill gas extraction, according to some embodiments.

This disclosure describes devices and techniques for controlling landfill gas extraction. FIG. 1 illustrates a landfill gas extraction system 100, according to some embodiments. In some embodiments, a landfill gas extraction system may include one or more gas extraction wells 102 coupled to one or more wellheads 104. In some embodiments, each wellhead may be in fluid communication with a single, corresponding well. In some embodiments, the landfill gas extraction system 100 may include a gas extraction piping system 108 coupling the well(s) 102 to a gas collection system 110, and one or more In Situ Control Mechanisms 106 for controlling extraction of the landfill gas through the well(s) 102 and gas extraction piping system 108 to the gas collection system 110. In some embodiments, gas collection system 110 may supply the extracted landfill gas to a gas output, such as a gas-to-energy power plant 112, which may convert the landfill gas into electrical power (e.g., by burning the landfill gas to turn the rotor of a generator or turbine). In some embodiments, the In Situ Control Mechanism(s) 106 may operate (e.g., individually, in concert with each other, and/or under the control of a controller) to improve gas extraction efficiency and/or to control the extraction process for a variety of desired outcomes including the delivery of the extracted gas into a natural gas pipeline system. In some embodiments the controller may be located remote from the In Situ Control Mechanisms. (Such a remotely located controller is not shown in FIG. 1, but is shown in FIG. 5 and described below.)

It should be appreciated that an In Situ Control Mechanism, as described herein, may control one or more parameters associated with a well, but is not a requirement that all other In Situ Control Mechanism be physically located at that well. The In Situ Control Mechanism(s) may be disposed at any suitable location(s). In some embodiments, each In Situ Control Mechanism may be coupled to a single, corresponding well. In some embodiments, an In Situ Control Mechanism may be coupled to one or more wells. In some embodiments, some or all of the gas extraction wells in a landfill gas extraction system may be outfitted with an In Situ Control Mechanism 106, as depicted in FIG. 1. In some embodiments, an In Situ Control Mechanism 106 may be positioned at or adjacent to one or more junction points in the gas extraction piping system 108 (header junctions, or leachate junctions, or others) to control the performance of an entire section of piping. In some embodiments, an In Situ Control Mechanism 106 may be positioned between the gas extraction well 102 and the gas collection system 110 such that gas coming from the well flows through the In Situ Control Mechanism 106 on its way to the rest of the collection system. The In Situ Control Mechanism 106 may be installed permanently in a suitable location (e.g., in, on, adjacent to, and/or near a well and/or gas extraction piping), or may be moved from location to location (e.g., well to well) over time.

Figure 2:
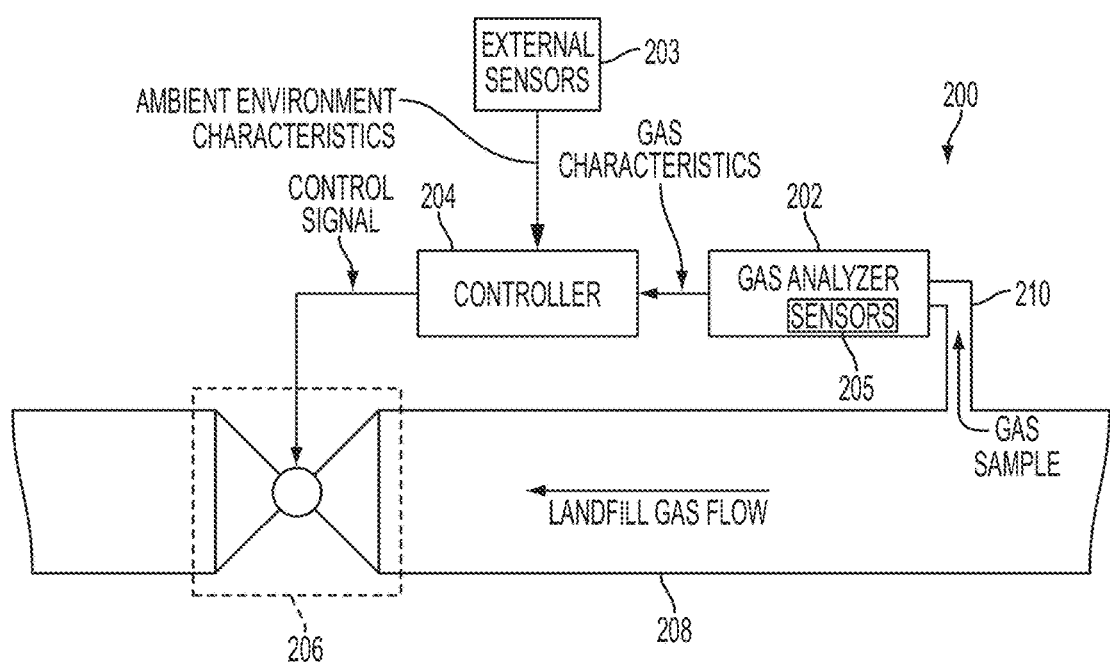
FIG. 2 is a block diagram illustrating an in situ control mechanism for landfill gas extraction, according to some embodiments.

A block diagram of some embodiments of an In Situ Control Mechanism 200 is presented in FIG. 2. In some embodiments, an In Situ Control Mechanism may include one or more mechanisms configured to control the flow of landfill gas from one or more wells to gas collection system 110 through gas extraction piping system 108. Any suitable flow-control mechanism 206 may be used, including, without limitation, a valve (e.g., a solenoid valve, latching solenoid valve, pinch valve, ball valve, butterfly valve, ceramic disc valve, check valves, choke valves, diaphragm valves, gate valves, globe valves, knife valves, needle valves, pinch valve, piston valve, plug valve, poppet valve, spool valve, thermal expansion valve, pressure reducing valve, sampling valve, safety valve) and/or any other suitable type of flow-control mechanism.

In some embodiments, an In Situ Control Mechanism may include one or more actuation devices configured to control operation of the one or more flow-control mechanisms (e.g., to open a flow-control mechanism, close a flow-control mechanism, and/or adjust a setting of a flow-control mechanism). In some embodiments, an In Situ Control Mechanism may include a controller 204 configured to determine the settings to be applied to the one or more flow-control mechanisms (e.g., via the actuation devices), and/or configured to apply the settings to the one or more flow-control mechanisms (e.g., via the actuation devices). In some embodiments, the settings to be applied to the one or more flow-control mechanisms (e.g., via the actuation devices) may be determined remotely and communicated to the In Situ Control Mechanism (e.g., by a remotely located controller) using any suitable communication technique, including, without limitation, wireless communication, wired communication, and/or power line communication.

In some embodiments, an In Situ Control Mechanism may include one or more sensor devices configured to sense one or more attributes associated with the landfill, including, without limitation, attributes of the landfill, attributes of the landfill gas, attributes of an area adjacent to the landfill, and/or attributes of the landfill's gas extraction system. In some embodiments, the In Situ Control Mechanism may include one or more actuation devices configured to control operation of the one or more sensor devices (e.g., to activate a sensor device, deactivate a sensor device, and/or collect data from the sensor device). In some embodiments, an In Situ Control Mechanism may include a controller 204 configured to determine the settings (e.g., control signals) to be applied to the one or more actuation and/or sensor devices, configured to apply the settings to the one or more actuation and/or sensor devices, and/or configured to collect data (e.g., measurements) obtained by the one or more sensor devices. In some embodiments, the settings to be applied to the one or more actuation and/or sensor devices may be determined remotely and communicated to the In Situ Control Mechanism (e.g., by a remotely located controller) using any suitable communication technique, including, without limitation, wireless communication, wired communication, and/or power line communication. In some embodiments, the In Situ Control Mechanism may communicate the one or more sensed attributes associated with the landfill (e.g., to a remotely located controller).

In some embodiments, the one or more sensor devices may include a Gas Analyzer 202. In some embodiments, a Gas Analyzer 202 may collect a sample of landfill gas from the gas extraction piping 208 through an input port 210, determine (e.g., compute, measure and/or sense) one or more characteristics of that gas, and/or report the one or more characteristics of the gas to a controller (e.g., local controller 204 and/or a remotely located controller). In some embodiments, the Gas Analyzer may determine the gas temperature, pressure, flow rate, humidity, energy content (e.g., energy density), gas composition (partial pressure or concentration of methane, oxygen, carbon dioxide, carbon monoxide, hydrogen sulfide, nitrogen and/or any other suitable gas) and/or any other characteristics of the landfill gas coming from the gas extraction well(s) upstream from the location where the In Situ Control Mechanism is installed.

Accordingly, in some embodiments, Gas Analyzer 202 may include sensors 205 configured to make such measurements. Sensors 205 may be of any suitable type. In some embodiments, sensors 205 may include a sensor configured to detect partial pressure and/or concentration of methane in landfill gas, a sensor configured to detect partial pressure and/or concentration of oxygen in landfill gas, a sensor configured to detect partial pressure and/or concentration of carbon dioxide in landfill gas, a sensor configured to detect partial pressure and/or concentration of carbon monoxide in landfill gas, a sensor configured to detect partial pressure and/or concentration of hydrogen sulfide in landfill gas, a sensor configured to detect partial pressure and/or concentration of nitrogen in landfill gas, and/or a sensor to detect partial pressure or concentration of any suitable gas in landfill gas.

In some embodiments, sensors 205 may include one or more non-dispersive infrared (NDIR) sensors, mid infrared optical sensors, catalytic beads, electrochemical sensors, pellistors, photoionization detectors, zirconium oxide sensors, thermal conductivity detectors, and/or any other sensing technology. Gas Analyzer 202 may be configured to measure flow rate by using one or more sensors 205 to determine a pressure differential across a venturi, orifice plate, or other restriction to the flow of gas; by pitot tube, mechanical flow meter, heated wire or thermal mass flow meter, and/or using any other suitable technique. Gas Analyzer 202 may be configured to measure temperature with a thermocouple, a negative or positive temperature coefficient resistor, capacitor, inductor, a semiconducting device, and/or using any other suitable technique.

In some embodiments, one or more external sensors 203 may be used to measure one or more characteristics of the ambient environment outside of Gas Analyzer 202 (e.g., outside of In Situ Control Mechanism 200). The external sensor(s) 203 may provide obtained measurements to In Situ Control Mechanism 200 (e.g., to controller 204) and/or to one or more computing devices located remotely from In Situ Control Mechanism 200 (e.g., by using a wireless link, a wired link, and/or any suitable combination of wireless and wired links). In some embodiments, external sensor(s) 203 may include one or more temperature sensors configured to measure temperature outside the control mechanism 200 (e.g., the ambient atmospheric temperature) and/or any other suitable location. In some embodiments, external sensor(s) 203 may include one or more atmospheric pressure sensor(s) configured to measure atmospheric pressure outside of the control mechanism 200 (e.g., ambient atmospheric pressure) and/or any other suitable location. In some embodiments, sensors 203 may be used to measure one or more characteristics of the ambient environment. Additionally or alternatively, in some embodiments, information about the characteristic(s) of the ambient environment may be obtained from an external data source (e.g., external forecast data, National Oceanic and Atmospheric Administration (NOAA) data for temperature and/or barometric pressure).

In some embodiments, the gas characteristics may be sampled once in each reading, or may be sampled many times and statistics about the distribution of values may be determined. The gas characteristics may be continuously determined, or they may be determined at discrete time intervals. In some embodiments, the Gas Analyzer may analyze gas in the main flow of landfill gas (e.g., within gas extraction piping 208). In some embodiments, the Gas Analyzer may draw a small sample of gas into a separate chamber for analysis. In some embodiments, certain parameters (for example flow rate, pressure, temperature, humidity, and the like) may be measured in the main gas stream (e.g., may be measured by sensors disposed directly within extraction gas piping), and others may be analyzed in a separate chamber.

In order to improve measurement accuracy, measurement resolution, measurement repeatability, sensor lifetime, and/or sensor reliability, a sample of gas from the well may be pre-treated before analysis, which pre-treatment may include heating, cooling, drying, and/or any other suitable pre-treatment processing (e.g., through forced condensation, passing through a desiccant, or any other suitable technique), filtered to remove particles, filtered to remove contaminants or other chemicals, pressurized, de-pressurized, and/or otherwise treated before being analyzed. After analyzing and reporting gas characteristics (e.g., to local controller 204 and/or to a remotely located controller), the Gas Analyzer may purge the gas sample from the chamber and vent it to the atmosphere, or return it to the main gas flow. In some embodiments, the analyzed gas sample may be purged prior to reporting the gas characteristics to a controller.

One embodiment of a Gas Analyzer 300 utilizing pre-treatment mechanisms as described above is illustrated in FIG. 3. In the Gas Analyzer 300 of FIG. 3 and other arrangements not explicitly described here, a small sample of landfill gas may be taken into the Gas Analyzer through input port 310 (e.g., from the main flow of landfill gas in gas extraction piping 308 between the gas extraction well and the gas collection system) and sent through a drying element

312 and a series of one or more flow-control mechanisms (e.g., valves) before entering the gas analysis sample chamber 302. In some embodiments, at the beginning and end of a gas measurement cycle, both valves 316 and 318 are in the closed state. Valve 316 may be opened and the pump 314 may be turned on in order to draw a sample of landfill gas through the drying element 312 and into the gas analysis sample chamber 302 for analysis. At the end of a measurement cycle, the pump 314 may be turned off and valve 316 may be closed to stop the flow of gas into the sample chamber 302. In some embodiments, the gas sample may be purged from sample chamber 302 by opening valve 318. Under typical operating conditions, the gas collection system and gas extraction well(s) may be at negative pressure (i.e., operating under vacuum conditions) relative to atmospheric pressure, such that opening valve 318 may pull ambient air through the Gas Analyzer 300 to purge the sample chamber 302 of landfill gas. In some embodiments, one or more valves of Gas Analyzer 300 may be toggled and a pump (e.g., pump 314) may be activated to force purge sample chamber 302 with ambient air. Forced purging may be beneficial when one or more wells upstream from Gas Analyzer 300 are operating under positive pressure relative to atmospheric pressure (e.g., because the gas extraction system's vacuum is off-line or because the one or more wells are under-extracted). For example, forced purging may be an effective technique for clearing condensate from the Gas Analyzer's tubes and/or for clearing sample gas from sample chamber 302 in cases where the upstream well(s) are operating under positive pressure. (Although not shown, one of ordinary skill in the art would understand that a valve may be placed between pump 314 and input port 310, and that sample chamber 302 may be force purged by closing this valve and by opening valves between pump 314 and atmospheric port 320.) After purging the gas sample from Gas Analyzer 300, valve 318 may be closed to stop atmospheric air from leaking into the gas collection system.

Figure 3:
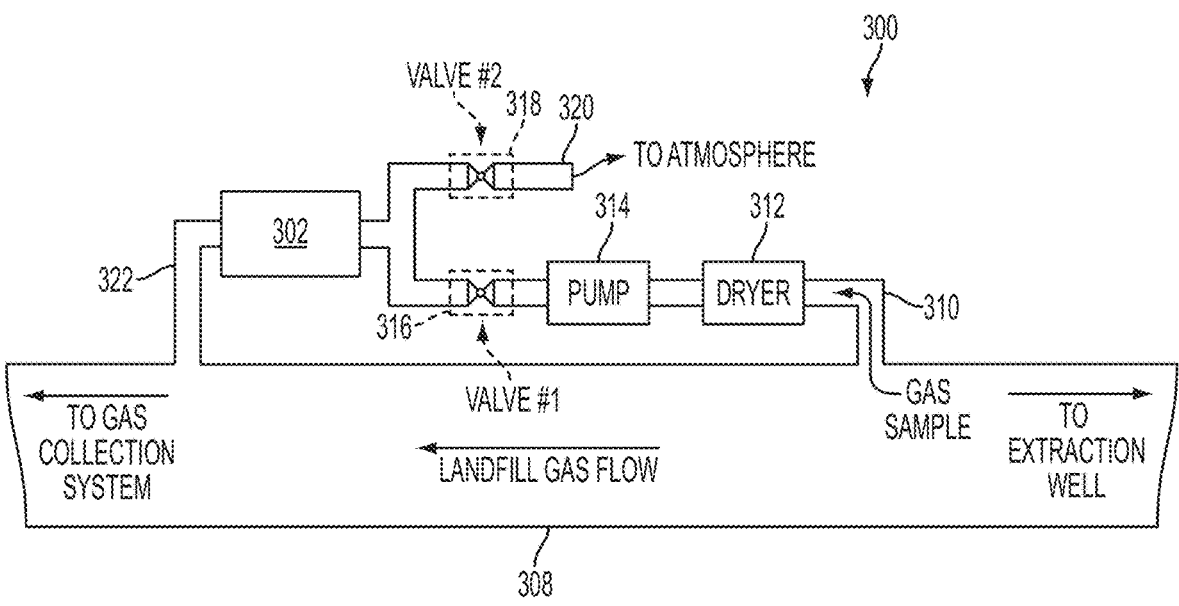
FIG. 3 is a block diagram illustrating a gas analyzer of an in situ control mechanism for landfill gas extraction, according to some embodiments.

Configurations that perform a similar function to the embodiment of FIG. 3 and which, while not described explicitly here, are within the scope of the present disclosure. For example, the pump 314 may be placed after valve 316, or after the gas analyzer sample chamber 302, or the drying element 312 may be moved to a different point in the flow path. Similarly, the functionality provided by valve 316 and the pump 315 may be consolidated by the use of a sealed pump design (e.g., a peristaltic pump). An additional valve may be added after the gas analyzer (e.g., in a port 322 coupling the sample chamber 302 to the gas extraction piping 308), for additional control or to prevent backflow into the sample chamber. Additionally, the Gas Analyzer may be outfitted with additional modules to provide other pre-treatment of the gas in addition to or in alternative to drying (for example, particle filtering, removal or deactivation of hydrogen sulfide or other chemicals, etc.).

In some embodiments, the flow-control mechanism(s) of Gas Analyzer 300 may include solenoid valves, latching solenoid valves, pinch valves, ball valves, butterfly valves, ceramic disc valves, check valves, choke valves, diaphragm valves, gate valves, globe valves, knife valves, needle valves, pinch valves, piston valves, plug valves, poppet valves, spool valves, thermal expansion valves, pressure reducing valves, sampling valves, safety valves, and/or any other type of flow-control mechanism.

In some embodiments, the Gas Analyzer may utilize non-dispersive infrared (NDIR) sensors, catalytic beads, electrochemical sensors, pellistors, photoionization detectors, zirconium oxide sensors, thermal conductivity detectors, and/or any other sensing technology. Flow rate may be measured by a pressure differential across a venturi, orifice plate, or other restriction to the flow of gas; by pitot tube, mechanical flow meter, heated wire or thermal mass flow meter, and/or using any other suitable technique. Temperature may be measured with a thermocouple, a negative or positive temperature coefficient resistor, capacitor, inductor, a semiconducting device, and/or using any other suitable technique. Temperature may be measured inside the well, in the main gas flow from the well to the collection system, inside a sampling chamber, outside of the control mechanism (e.g., ambient atmospheric temperature), and/or at any other suitable point. Atmospheric pressure may be measured outside of the control mechanism (e.g., ambient atmospheric pressure) and/or at any other suitable location. Temperature, pressure, gas composition, and/or other readings from different points within the gas extraction well, the In Situ Control Mechanism, and/or the gas collection system may be used in conjunction with each other to obtain a more complete analysis of the operating state of the landfill gas collection system.

Figure 4:
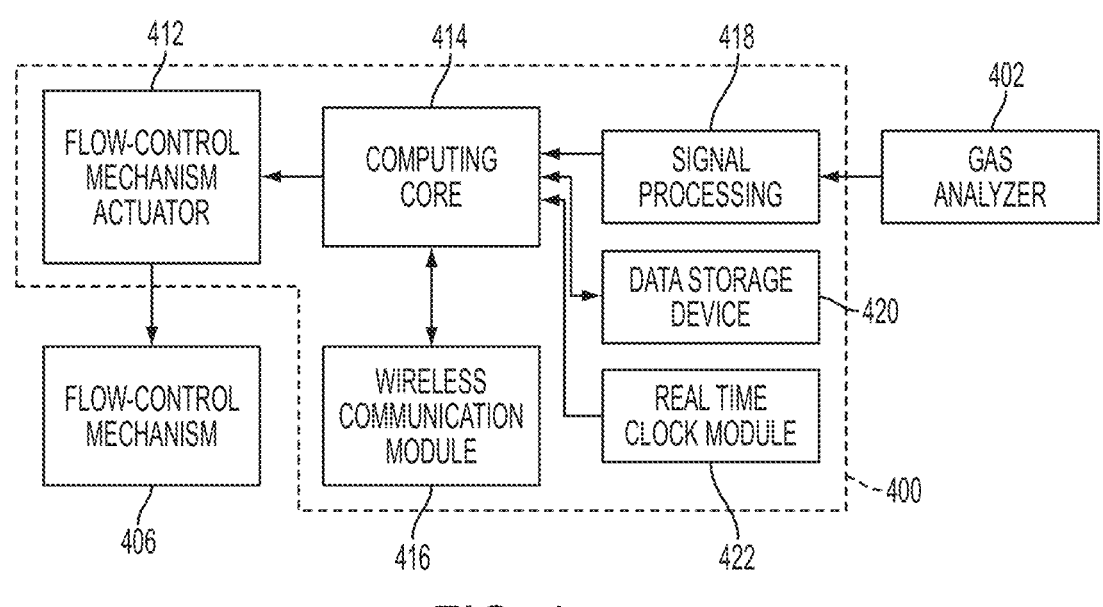
FIG. 4 is a block diagram illustrating a controller of an in situ control mechanism for landfill gas extraction, according to some embodiments.

FIG. 4 shows a controller of an In Situ Control Mechanism, according to some embodiments. In some embodiments, the Controller 400 of an In Situ Control Mechanism may include functional blocks as indicated in FIG. 4. In the embodiment of FIG. 4, the Controller 400 includes a Signal Processing Module 418, a Data Storage Device 420, a Real Time Clock Module 422, a Wireless Communication Module 416, and/or a Flow-Control Mechanism Actuator 412 (e.g., valve drive buffer) for providing a control signal to the Flow-Control Mechanism 406. Other embodiments may use only parts of this implementation, while others may add additional functional modules for supporting functions. For example, in some embodiments, the Controller of an In Situ Control Mechanism may be implemented using a one or more processors as described below.

In some embodiments, the Controller 400 of the In Situ Control Mechanism may use data about environmental conditions in and around the landfill (e.g., in and around the gas extraction well upon which the In Situ Control Mechanism is installed) to determine the settings to be applied to the flow-control mechanism. In some embodiments, a remotely-located controller may use the environmental data to determine the settings to be applied to the flow-control mechanism, and may communicate those settings to the In Situ Control Mechanism. The environmental data may include information about parameters including, but not limited to atmospheric pressure, ambient temperature, wind direction, wind speed, precipitation, humidity, and/or any other suitable environmental parameter. The In Situ Control Mechanism may use information from one or more other sensors placed in or around the gas extraction well, including, without limitation, atmospheric pressure sensor(s) (sometimes termed barometric pressure sensor(s), subsurface temperature probe(s), subsurface moisture probe(s), collection well liquid level measurement sensors, measurements of the chemical and/or biological processes (for example, pH measurements, tests for the presence of other chemicals or biological by-products, etc.) occurring in the section of waste that is in the vicinity of the gas extraction well, and/or any other suitable information. In embodiments, where one or more atmospheric pressure sensors are used, the atmospheric pressure sensors may be of any suitable type, as aspects of the technology described herein are not limited in this respect.

In some embodiments, the Controller 400 of the In Situ Control Mechanism may use the current data about the gas characteristics and/or environmental parameters, and/or it may incorporate historical data about the performance of the gas extraction well to determine the settings to be applied to the Flow-Control Mechanism. In some embodiments, a remotely-located controller may use the gas data, environmental data, and/or historical data to determine the settings to be applied to the flow-control mechanism, and may communicate those settings to the In Situ Control Mechanism. The In Situ Control Mechanism may, in some embodiments, incorporate past and/or present data about gas production into one or more predictive models and may use the predictive model(s) to determine the modulation of the Flow-Control Mechanism state.

In some embodiments, the Signal Processing Module 418 takes gas characteristics data from the Gas Analyzer 402 and converts it into a form that can be interpreted by the Computing Core 414. This may involve a interpreting a serial digital data stream via a serial parsing algorithm, a parallel parsing algorithm, analog signal processing (for example, performing functions on analog signals like filtering, adding or removing gain, frequency shifting, adding or removing offsets, mixing or modulating, and the like), digital signal processing (digital filtering, convolution, frequency shifting, mixing, modulating, and the like), analog-to-digital or digital-to analog conversion, and/or any other suitable signal processing technique that will be recognized by one of ordinary skill in the art.

In some embodiments, the Data Storage Device 420 may include any volatile and/or non-volatile memory element, including but not limited to flash memory, SD card, micro SD card, USB drive, SRAM, DRAM, RDRAM, disk drive, cassette drive, floppy disk, cloud storage backup, and/or any other suitable computer-readable storage medium. The Data Storage Device may serve as a data recovery backup, or it may hold data for temporary intervals during the calculation of control signals. The Data Storage Device may be removable, or it may be fixed.

In some embodiments, the Real Time Clock Module 400 may include any circuit and/or functional module that allows the Computing Core to associate the results of a gas analyzer reading with a date or time (e.g., a unique date or time stamp).

In some embodiments, the Wireless Communication Module 416 may include, but is not limited to: a radio transceiver (AM or FM, or any other type), television, UHF, or VHF transceiver, Wi-Fi and/or other 2.4 GHz communication module, cellular chipset (2G, 3G, 4G, LTE, GSM, CDMA, etc.), GPS transmitter, satellite communication system, and/or any other suitable wireless communication device. The Wireless Communication Module may have an integrated antenna, and/or an external one. The Wireless Communication Module may transmit, receive, and/or have two-way communication with a central source and/or be capable of point-to-point communication with another module. In some embodiments, the Wireless Communication Module may include a 2G chipset that allows the In Situ Control Mechanism to connect to existing telecommunications infrastructure.

In some embodiments, the Computing Core 414 may include, but is not limited to: a microprocessor, a computer, a microcontroller, a field programmable gate array (FPGA), an application specific integrated circuit (ASIC), a digital signal processor (DSP), an analog computer or control system, and/or any other suitable computing device. In some embodiments, the Computing Core may have integrated Analog-to-Digital converters, pulse width modulation detectors, edge detectors, frequency detectors, phase detectors, amplitude detectors, demodulators, RMS-DC converters, rectifiers, and/or other suitable signal processing modules.

In some embodiments, the Flow-Control Mechanism Actuator 412 (e.g., a valve drive buffer) may include any circuit that can translate commands from the Computing Core into an appropriate actuation signal (e.g., driving signal) for the Flow-Control Mechanism 406. In some embodiments, translating commands from the Computing Core may comprise analog signal processing on a voltage (for example, adding/removing gain, offset, filtering, mixing, etc.), analog signal processing on a current control (for example, conversion to a 4-20 mA control loop, increasing output current drive capability), pulse width modulating a digital signal, digital signal processing, digital-to-analog or analog-to-digital conversion, and/or any other suitable techniques.

In some embodiments, the Flow-Control Mechanism 406 of the In Situ Control Mechanism may comprise a solenoid valve, latching solenoid valve, pinch valve, ball valve, butterfly valve, ceramic disc valve, check valve, choke valve, diaphragm valve, gate valve, globe valve, knife valve, needle valve, pinch valve, piston valve, plug valve, poppet valve, spool valve, thermal expansion valve, pressure reducing valve, sampling valve, safety valve, and/or any other suitable type of flow-control mechanism. The Flow-Control Mechanism may have two or more discrete operating states, or it may provide continuous adjustment of the operating state (e.g., valve position) for fine control of operating pressure, temperature, flow, gas characteristics, etc.

In some embodiments, the In-Situ Control Mechanism may modulate the Flow-Control Mechanism to achieve any number of desired outcomes, or it may determine the state of the Flow-Control Mechanism based on an optimization and/or prioritization of multiple output parameters. Some examples of control schemes are further provided herein.

In some embodiments, some or all of the gas extraction wells and/or piping junction points in a landfill may be outfitted with In-Situ Control Mechanisms to form at least a portion of a control system for controlling gas extraction across the entire landfill or a set of wells within the landfill (the "landfill under control"). One embodiment of such a control system is shown in FIG. 5.

FIG. 5 shows a control system 500 for a landfill gas extraction system, according to some embodiments. In some embodiments, control system 500 may include one or more In Situ Control Mechanisms 506 (506a, 506b, . . . 506n) configured to control gas flow in a gas extraction system in a landfill under control 520. In some embodiments, control system 500 may include a controller module 504 for modeling aspects of the landfill under control, for communicating with the In Situ Control Mechanisms, and/or for controlling the operation of the In Situ Control mechanisms. In some embodiments, controller module 504 may be implemented on one or more computers located remotely from the In Situ Control Mechanisms (e.g., on a centralized computer or in a distributed computing environment). In some embodiments, controller module 504 may execute a multitasking program with different tasks configured to control the operation of different In Situ Control Mechanisms and/or to communicate with different In Situ Control Mechanisms. In some embodiments, the functionality described below as being performed by controller module 504 may be performed by one or more In Situ Control Mechanisms 506 individually or in concert. In some embodiments, controller module 504 may communicate with the In Situ Control Mechanisms through a device manager 502. In some embodiments, controller module 504 is in communication with a user interface 508 and/or a database 510.

In some embodiments, some or all of these In-Situ Control Mechanisms 506 may contain wireless communication capability to establish Wireless Data Links to controller module 504 (e.g., through device manager 502). Wireless Data Links may operate in either a unidirectional or a bidirectional manner. The network of Wireless Data Links may be implemented using a mesh network, a star network, point-to-point communication, and/or any other suitable communication technique. In-Situ Control Mechanisms 506 may send information over a communication network to a distributed network (e.g., the "cloud"). Communication may occur through a system including but not limited to a cell phone network (2G, 3G, 4G LTE, GSM, CDMA 1×RTT, etc.), a satellite network, a local area network connected to the Internet, etc. In some embodiments, the In Situ Control Mechanisms 506 may communicate with each other and/or with controller module 504 using wired data links, Wireless Data Links, power line communication, and/or any other suitable communication technique.

Information sent (e.g., over Wireless Data Links) by the In-Situ Control Mechanisms 506 may include but is not limited to sensor data, environmental data, failure notifications, status notifications, calibration notifications, etc. Information received by the In-Situ Control Mechanisms may include but is not limited to: raw or pre-processed data about the current or past operational state of other landfill gas extraction wells in the landfill under control, command and control signals, desired operating states, predictive calculations about the operating state of the well upon which the In-Situ Control Mechanism is installed or other landfill gas extraction wells, failure notifications, status notifications, calibration changes, software and/or firmware updates, flow-control mechanism settings, sensor settings, and/or other information.

In some embodiments, In Situ Control Mechanisms 506 in the landfill under control 520 may communicate with a Device Manager 502, as indicated in FIG. 5, and/or they may communicate directly with each other. The Device Manager 502 may include software operating on a computer in the landfill under control, or operating on a remote server, and/or operating on a distributed computing network ("the cloud") in one or multiple locations. In some embodiments, Device Manager 502 may be implemented using a computing system 1500 as described below. The Device Manager 502 may collect information from alternate sources—including but not limited to environmental data, past history about electrical power demand and/or prices, forecasts about future electrical power demand and/or prices, etc. In some embodiments, the Device Manager 502 may be in constant communication with the In-Situ Control Mechanisms 506, or it may communicate asynchronously with the In-Situ Control Mechanisms. In some embodiments, the Device Manager 502 may hold a queue of commands or other information to be passed to the In Situ Control Mechanism(s) 506 upon the establishment of a data link (e.g., reestablishment of a Wireless Data Link).

In some embodiments, the Device Manager 502 may associate a set of In-Situ Control Mechanisms 506 into a single landfill under control 520, and it may add or remove additional In-Situ Control Mechanisms 506 to that landfill under control 520 to accommodate the addition or removal of In-Situ Control Mechanisms from the site. The Device Manager 502 may contain or perform authentication or encryption procedures upon establishing a data link (e.g., a Wireless Data Link) with an In-Situ Control Mechanism.

Security protocols implemented by the Device Manager may include, but are not limited to: internet key exchange, IPsec, Kerberos, point to point protocols, transport layer security (TLS), HTTPS, SSH, SHTP, etc.

In some embodiments, the Device Manager 502 may communicate with a controller module 504. The controller module 504 may include one or more applications running on a distributed computational platform (e.g., a "cloud server"), a traditional server infrastructure, a computing system 1500 as described below with respect to FIG. 15, and/or other suitable computer architecture recognized by those of ordinary skill in the art. It should be appreciated, however, that control functions as described herein may be distributed across device manager 502, controller module 504 and/or any other computing components in any suitable way. Similarly, control functions may be distributed across processors (e.g., controllers) associated with one or more In Situ Control Mechanisms.

In some embodiments, control system 500 may be configured to predict future states of the landfill under control, and/or may be configured to use such predictions to control the operation of a gas extraction system associated with the landfill under control. In some embodiments, using one or more predictions regarding the future state(s) of the landfill under control to control the operation of the gas extraction system may improve the performance (e.g., efficiency) of the gas extraction system, relative to the performance of conventional gas extraction systems.

Aggregate Level Landfill Gas Extraction Control

As described herein, aspects of the present disclosure provide for site-level control of landfill gas extraction. For example, in some embodiments, the extraction of landfill gas from a respective well may be based at least in part on aggregate landfill gas quality (e.g., composition) of landfill gas collected from a plurality of wells.

Site-Level Landfill Gas Extraction Control Systems

Figure 6:
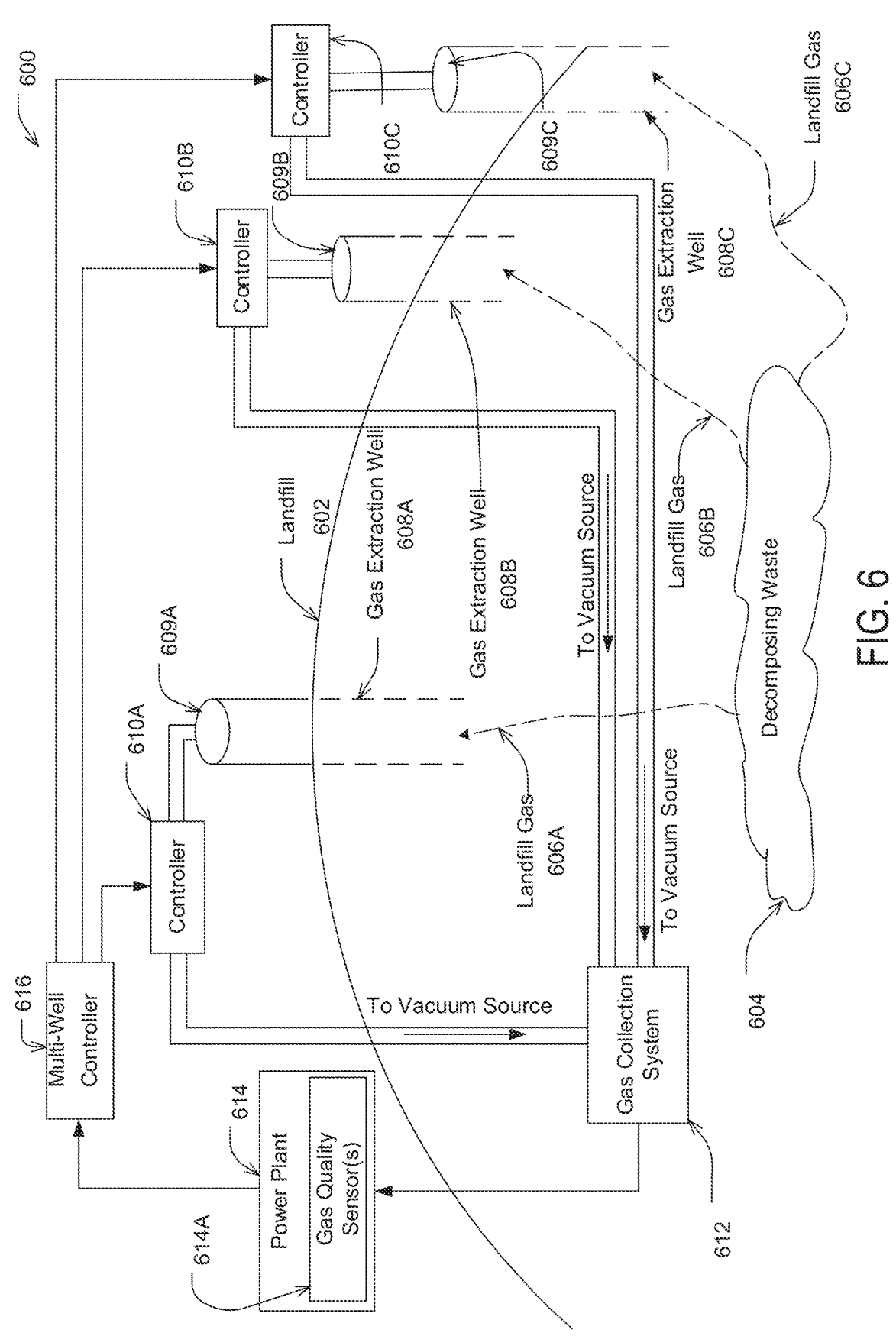
FIG. 6 is an example of a landfill gas extraction system, according to some embodiments.

Example systems for site-level control of landfill gas extraction are further provided herein. As shown in FIG. 6, landfill gas collected from multiple different extraction wells in a landfill may be aggregated at a gas output. For example, the gas output may be a power plant that uses the aggregated landfill gas to generate electricity. In another example, the gas output may be a processing plant where landfill gas collected from the extraction wells undergoes treatment. The inventors have recognized that the power plant may require the aggregated landfill gas to have a certain gas quality (e.g., a certain energy content, a certain gas composition) in order to process the aggregate landfill gas instead of flaring it. Accordingly, the inventors have developed a control system that concurrently controls extraction of landfill gas from multiple wells based on one or more target parameters for the gas output (e.g., a collection point for extracted landfill gas from a plurality of wells such as a power plant or a treatment plant). The multiple wells may each have a valve disposed in well piping coupled to the well that modulates a flow rate of landfill gas being extracted from the well. In some embodiments, the control system may obtain a value indicating a characteristic of the landfill gas collected at the gas output (e.g., an energy content of the landfill gas, a concentration of a constituent gas in the landfill gas), and determine whether the characteristic is outside of a target range (e.g., greater than an upper endpoint and/or less than a lower endpoint). In some embodiments, the control system may determine whether the characteristic is different than a target value for the characteristic. In response to determining that the measured characteristic is outside of the target range, for example, the control system may control the valves disposed in the well piping to control flow rates of landfill gas being extracted from the multiple wells. The controller may change the degree to which one or more of the valves is open to change the flow rates of one or more of the multiple gas extraction wells.

The inventors have recognized that the quality of landfill gas extracted from a gas extraction well is affected by a variety of different factors. By way of example and not limitation, such factors may include changes in barometric/ambient pressure, changes in ambient temperature, precipitation, and changes in pressure of a vacuum source. Furthermore, extraction from an individual well may have to be adjusted such that landfill gas aggregated from multiple wells meets certain standards (e.g., energy content standards, balance gas limits, etc.). Accordingly, the inventors have developed a system for controlling extraction of landfill gas from a gas extraction well based on multiple factors. In some embodiments, the system has a controller that determines one or more control variables based on measurements of change in pressure of a vacuum source, change in barometric pressure outside of the landfill, change in ambient temperature outside of the landfill, and/or a quality of aggregated landfill gas from multiple wells. The system then controls a flow control mechanism (e.g., a valve) to adjust a flow rate of landfill gas being extracted from the gas extraction well based on the control variable(s).

FIG. 6 illustrates an example environment 600 in which aspects of the technology described herein may be implemented. The environment 600 includes a landfill 602, which holds decomposing waste 604. The decomposing waste 604 produces landfill gas (LFG) 606A-C which flows out from the landfill 602 through gas extraction wells 608A-C. A gas extraction well may also be referred to herein as a "well." The gas extraction wells 608A-C include respective wellheads 609A-C. Each of the gas extraction wells 608A-C is coupled to a respective one of the controllers 610A-C through the wellhead of the gas extraction well. Each of the controllers 610A-C may be configured to locally control extraction of gas from the gas extraction well that the controller is coupled to. A controller coupled to a particular well may be referred to herein as a "local controller." A gas collection system 612 collects the landfill gas extracted from the wells 608A-C. The gas collection system 612 supplies the extracted landfill gas to a power plant 614. The power plant 614 may be communicatively coupled to a multi-well controller 616. The multi-well controller 616 is communicatively coupled to the controllers 610A-C associated with wells 608A-C. The multi-well controller 616 receives, from the power plant 614, information indicating gas quality of landfill gas aggregated from the wells 608A-C. The multi-well controller 616 uses the information to feed control inputs to the local controllers 610A-C to globally control extraction of landfill gas at the wells 608A-C. It should be appreciated that although three wells are shown in FIG. 6, this is by way of example and not limitation, as a site may include any suitable number of wells (e.g., at least 10, at least 50, at least 100, at least 250, between 50 and 1000 wells).

In some embodiments, the gas collection system 612 includes a vacuum source. The vacuum source generates a negative pressure differential between the gas collection system 612 and the landfill 602. The negative pressure differential causes the landfill gas 606A-C to flow from the landfill 602 to the gas collection system 612 through the wells 608A-C. In some embodiments, the gas collection system 612 may comprise an additional location where extracted landfill gas is stored, and/or where the extracted landfill gas may be treated (e.g., by removing impurities) before being supplied to the power plant 614. In some embodiments, the gas collection system 612 may include a processing plant where the collected landfill gas is treated. The landfill gas may be treated to modify concentration(s) of one or more of the gases that make up the landfill gas. In some embodiments, the processing plant may be configured to treat the landfill gas to increase an energy content of the landfill gas. For example, the landfill gas may include methane, oxygen, carbon dioxide, hydrogen sulfide, nitrogen, and other gases. The processing plant may reduce the concentration(s) of one or more non-methane gases to increase energy content (e.g., energy density) of the collected landfill gas. The power plant 614 may be configured to generate electricity using the extracted landfill gas. For example, the power plant 614 may burn the extracted landfill gas to turn a rotor of an electricity generator or a turbine. Although the gas collection system 612 and the power plant 614 are shown separately in FIG. 6, in some embodiments, the gas collection system 612 and the power plant 614 may be components of a single system.

The power plant 614 includes one or more sensors 614A which the power plant may use to determine one or more measures of quality of extracted landfill gas. The landfill gas may be collected from multiple wells at the landfill 602, such as wells 608A-C. In some embodiments, the sensor(s) 614A may be configured to measure an energy content (e.g., energy density) of collected landfill gas. For example, the sensor(s) 614A may include a gas chromatograph that measures concentrations of one or more of the gases that make up the collected landfill gas (one or more of oxygen, nitrogen, methane, carbon dioxide, hydrogen sulfide, for example), and the multi-well controller 616 may use the concentration(s) to determine whether to adjust the flow rate of one or more of the gas extraction wells 608A-C. For example, the multi-well controller 616 may receive a measure of a concentration of a constituent gas in the landfill gas collected from the gas extraction wells 608A-C obtained by the gas quality sensor(s) 614 and use the measure of the concentration of the constituent gas to determine whether the concentration of landfill gas collected from the gas extraction wells 608A-C is outside of a target range and/or different from a target concentration.

In some embodiments, each of the local controllers 610A-C controls extraction of landfill gas locally at a respective one of the gas extraction wells 608A-C. Each of the local controllers 610A-C may be configured to operate to control extraction of landfill gas according to a local control method, for example, to achieve a target of energy content of extracted landfill gas, composition of extracted landfill gas, flow rate of gas extraction, regulatory requirements, and/or other parameters. In some embodiments, the controller may be configured to control a flow rate of landfill gas being extracted from the well. For example, the controller may be configured to control a position of a valve disposed in well-piping of the well which in turn modulates a flow rate of landfill gas being extracted from the well. Example operation of a controller is described above with reference to FIGS. 1-3. A local controller may also be referred to herein as an "in-situ control mechanism."

In some embodiments, the multi-well controller 616 controls extraction of landfill gas globally across multiple gas extraction wells, including the gas extraction wells 608A-C. In some embodiments, the multi-well controller 616 may be configured to concurrently control extraction of landfill gas from multiple wells. Concurrently controlling extraction of landfill gas from multiple wells may involve causing an adjustment in a valve at a first well during a first time period, and in a valve at a second well during a second time period that at least partially overlaps with the first time period. In some embodiments, the multi-well controller 616 may be configured to concurrently control extraction of landfill gas from multiple wells while a respective local controller 610A-C controls extraction of landfill gas from a respective gas extraction well according to a local control method.

In some embodiments, each of the controllers 610A-C may include a valve whose position controls a flow rate of landfill gas being extracted from a respective well. The multi-well controller 616 may control the positions of the valves of the controllers 610A-C to control, globally, flow rates of landfill gas being extracted from the wells 608A-C. In some embodiments, the multi-well controller 616 may be configured to control the positions of the valves of the controllers 610A-C by transmitting a control variable to each of the controllers 610A-C. Each of the controllers 610A-C uses the control variable to determine an adjustment to make to the degree that the valve being controlled by the controller is open. In some embodiments, the multi-well controller 616 may transmit a valve position adjustment to each of the controllers 610A-C. The controllers 610A-C may be configured to apply the received adjustment to the respective valves.

In some embodiments, the multi-well controller 616 may comprise at least one computer. The at least one computer may communicate with the controllers 610A-C. In some embodiments, the multi-well controller 616 may be configured to periodically transmit one or more control inputs to the controllers 610A-C. In some embodiments, the multi-well controller 616 may wirelessly transmit the control input(s) to the controllers 610A-C. In some embodiments, the multi-well controller 616 may communicate with the controllers 610A-C over wired connections.

Site-Level Landfill Gas Extraction Control Methods

As described herein, a multi-well controller may be configured to implement one or more site-level control techniques for controlling extraction of landfill gas based at least in part on aggregate gas quality of landfill gas collected from a plurality of wells. Examples of such techniques are further described herein.

Figure 7:
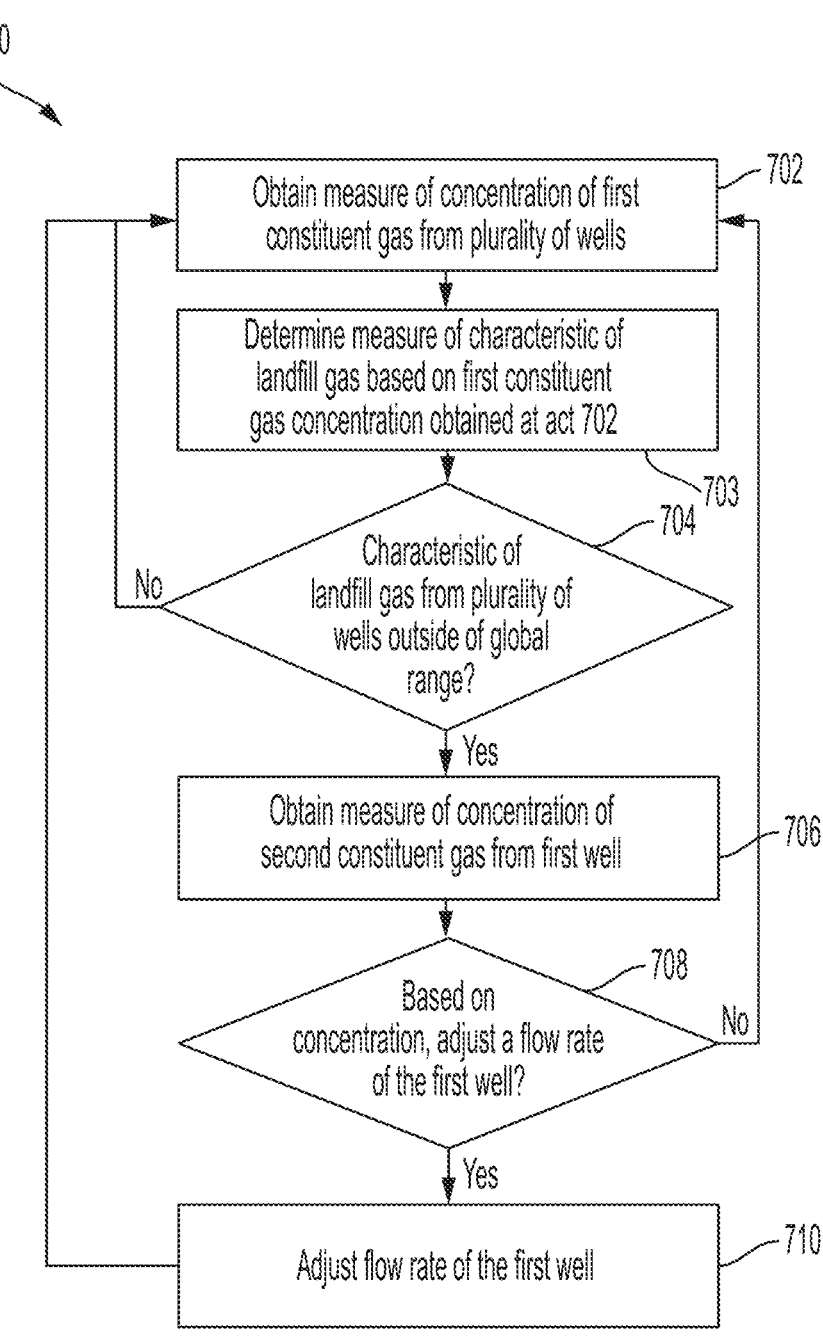
FIG. 7 is a flowchart of an illustrative process for controlling extraction of landfill gas through a gas extraction system, according to some embodiments.

FIG. 7 is a flowchart of an illustrative process for controlling extraction of landfill gas through a gas extraction system, according to some embodiments. In some embodiments, process 700 may be performed using at least one site-level controller (e.g., multi-well controller 616) and/or one or more local controllers (e.g., controllers 610A-C described above with reference to FIG. 6), as described herein.

Process 700 begins with act 702, where a measure of a concentration of a first constituent gas in landfill gas collected from a plurality of wells is obtained. For example, the concentration of the first constituent gas may be obtained by the gas quality sensor(s) 614 at the gas output. In some embodiments, act 702 comprises operating, for example, with the multi-well controller 616, a gas quality sensor, such as a gas chromatograph, to obtain the measure of concentration of the first constituent gas. In some embodiments, act 702 comprises receiving the measure of concentration of the first constituent gas from a gas quality sensor.

In some embodiments, the first constituent gas comprises at least one of oxygen, nitrogen, methane, and/or any other component of landfill gas. In some embodiments, the first constituent gas may be measured directly using a measurement from a gas quality sensor configured to obtain a concentration of the first constituent gas (such as by using an oxygen sensor, for example). In some embodiments, the concentration of the first constituent gas may be measured indirectly, for example, by suing measurements from a gas quality sensor of one or more other constituent gasses in the landfill gas collected from the plurality of wells and calculating a balance.

At act 703, the multi-well controller determines a measure of a characteristic of the landfill gas extracted from the plurality of wells based on the measure of concentration of the first constituent gas obtained at act 702. The characteristic of the landfill gas collected from the plurality of wells may be any characteristic of landfill gas for which it is desired to base control of landfill gas extraction from the plurality of wells on. For example, determining whether one or more of the plurality of wells should be adjusted may be based on the characteristic of the landfill gas collected from the plurality of wells. As such, the characteristic may be referred to as a top level parameter for controlling landfill gas extraction. In some embodiments, the characteristic comprises the measure of concentration of the first constituent gas itself, such as oxygen concentration, nitrogen concentration, or methane concentration, among others, for example.

In some embodiments, the characteristic of the landfill gas collected from the plurality of wells comprises a quality of landfill gas calculated using the measure of concentration of the first constituent gas, for example, an energy content of the landfill gas collected from the plurality of wells. In some embodiments, energy content of landfill gas or other fuel may indicate an amount of energy per unit of volume or mass of the landfill gas or other fuel. When energy content of landfill gas or other fuel indicates an amount of energy per unit volume of the gas or fuel, the energy content may be referred to as "energy density". As described herein, some embodiments of the technology described herein involve controlling gas extraction using energy content (e.g., based on measured and target energy content), which encompasses controlling gas extraction using energy content per unit volume (energy density), energy content per unit of mass, or any other suitable measure of energy content.

At act 704 it is determined, using the multi-well controller 616, for example, whether the characteristic of the landfill gas collected from the plurality of wells is outside of a global range. For example, the measure of the characteristic may be compared to upper and lower thresholds of the global range to determine whether the characteristic is greater than an upper threshold of the global range (e.g., a highest value of the global range) or less than a lower threshold of the global range (e.g., a lowest value of the global range). For example, in an embodiment where the characteristic comprises oxygen concentration, a global range for oxygen concentration may comprise 1-5% oxygen concentration and determining whether the characteristic is outside of the global range comprises determining whether the measure of oxygen concentration is less than 1% or greater than 5%. Further examples are provided in FIGS. 8A-10B

Although not shown in the illustrated embodiment, in some embodiments, the characteristic of the landfill gas collected from the plurality of wells may be compared to a target value for the characteristic to determine whether a measure of the characteristic differs from the target characteristic. In some embodiments, the characteristic of the landfill gas collected from the plurality of wells be compared to one of an upper or lower threshold to determine whether the measure of the characteristic is greater than an upper threshold or less than a lower threshold for the characteristic.

When, at act 704, the multi-well controller 616 determines that the characteristic of the landfill gas collected from the plurality of wells is not outside of the global range, then the process returns through the no branch to act 702 where another measure of concentration of the first constituent gas is obtained. Alternatively, in some embodiments, the process may end.

When, at act 704, the multi-well controller 616 determines that the characteristic of the landfill gas collected from the plurality of well is outside of the global range, the determination may indicate that the landfill gas collected from the plurality of wells is not of sufficient quality (e.g., the landfill gas collected from the plurality of wells does not comprise the necessary composition to process the aggregate landfill gas instead of flaring it) and that one or more adjustments should be made to one or more individual gas extraction wells. In that case, the method proceeds through the yes branch to act 706 to determine which of the plurality of wells to adjust. Although acts 708-710 are described with reference to a first well of the plurality of wells, it should be appreciated that the method may be performed for any number of the plurality of wells (e.g., each of the plurality of wells, a subset of the plurality of wells, including a second well).

At act 708, a local controller (e.g., one of local controllers 610A-C) determines, based on the concentration of a second constituent gas in landfill gas collected from the first well of the plurality of wells, whether to adjust a flow rate of the first well. For example, as described further herein, a measure of the concentration of the second constituent gas may be compared to a target range to determine whether the measure of the concentration of the second constituent gas is outside of the target range. For example, where the second constituent gas is oxygen, a measure of oxygen concentration of the landfill gas collected from the first well may be compared to a local range (e.g., 1-5% oxygen) to determine whether the measure of oxygen concentration is either less than 1% oxygen or greater than 5% oxygen. When it is determined that the measure of oxygen concentration is outside of the local range, the local controller may adjust the flow rate of the landfill gas being extracted from the landfill accordingly. Further examples are described herein, for example with respect to FIGS. 8A-10B.

In some embodiments, the measure of the concentration of the second constituent gas may be compared to a target value to determine whether the measure of the concentration of the second constituent gas is different than the target value. In some embodiments, the measure of the concentration of the second constituent gas may be compared to an upper and/or lower threshold to determine whether the measure of the concentration of the second constituent gas is greater than an upper threshold and/or less than lower threshold.

The second constituent gas may be any component of landfill gas for which it is desired to base the determination of which individual wells to adjust on. As such, the second constituent gas may be referred to as a secondary parameter for controlling landfill gas extraction. For example, where the second constituent gas comprises oxygen, determining which of the plurality of wells to adjust in response to a determination that one or more of the plurality of wells should be adjusted is based on the oxygen concentration of the individual wells. In some embodiments, the second constituent gas comprises at least one of oxygen, balance gas, methane, and/or any other component of landfill gas. In some embodiments, the first and second constituent gasses may be the same, while in other embodiments, the first and second constituent gasses may be different. In some embodiments, the first constituent gas may be measured directly using a sensor configured to obtain a concentration of the first constituent gas (such as by using an oxygen sensor, for example). In some embodiments, the concentration of the first constituent gas may be measured indirectly (e.g., for balance gas), for example, by measuring one or more other constituent gasses in the landfill gas collected from the plurality of wells and calculating a balance.

When, at act 708, it is determined that flow rate of landfill gas being extracted from the first well need not be adjusted, then the process returns through the no branch to act 702 where another measure of concentration of the first constituent gas may be obtained. Alternatively, in some embodiments, the process may end.

When, at act 708 it is determined that the flow rate of landfill gas being extracted from the first well should be adjusted, the process proceeds through the yes branch to act 710 where the flow rate of landfill gas being extracted from the first well is adjusted. For example, adjusting the flow rate of the first well may comprise decreasing or increasing the flow rate by adjusting a degree to which a valve of the first well is open. After adjusting the flow rate of the first well at act 710, the process may return to act 702 to obtain another measure of concentration of the first constituent gas, or, alternatively, the process may end.

Thus, process 700 provides for adjusting one or more wells when the quality of the aggregate landfill gas collected from the plurality of wells is inadequate (e.g., outside of a target range, different than a target value). The process 700 may improve aggregate gas quality by making adjustments to one or more of the plurality of wells. The process 700 provides for making adjustments to the selected individual wells (e.g., the "worst" or "best" quality gas extraction wells) to improve the quality of aggregate landfill gas in an efficient manner. In some embodiments, determining whether to adjust one or more wells of a plurality of wells may be determined based on a characteristic of aggregate landfill gas collected from the plurality of wells (e.g., a top level parameter) while determining which of the plurality of wells to adjust may be based on a characteristic of landfill gas collected from individual gas extraction wells (e.g., a secondary parameter).

As described herein, the techniques for site-level control of landfill gas extraction may be based on selecting a constituent gas and/or characteristic of landfill gas (e.g., energy content) as top level and secondary parameters governing the control of landfill gas extraction. Now described herein are example methods for site-level control having different examples of top level and secondary parameters.

Figure 8A:
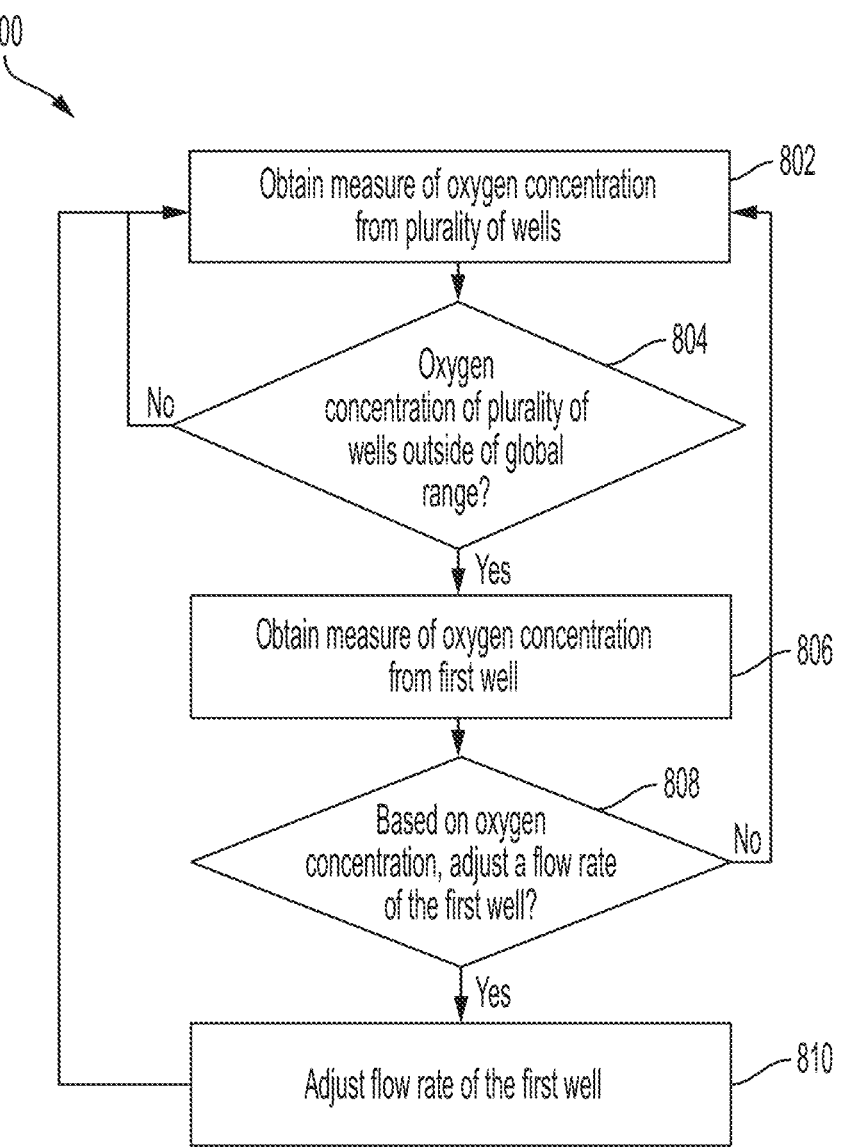
FIG. 8A is a flowchart of another illustrative process for controlling extraction of landfill gas through a gas extraction system, according to some embodiments.

FIG. 8A is a flowchart of another illustrative process for controlling extraction of landfill gas through a gas extraction system, according to some embodiments. In particular, FIG. 8A illustrates an example process 800 for site-level control of landfill gas extraction using oxygen concentration as a top level and secondary control parameter. Process 800 may be performed at least in part by using multi-well controller 616 and multiple local controllers 610A-C described above with reference to FIG. 6.

As shown in FIG. 8A, process 800 begins with act 802, where a measure of oxygen concentration of landfill gas collected from a plurality of wells is obtained, for example, by a multi-well controller. At act 804, the multi-well controller determines whether the concentration of oxygen in the landfill gas collected from the plurality of wells is outside of a global range (e.g., 0%-5% by volume, 0%-1% by volume, 0%-0.2% by volume, and/or any other suitable target range within these ranges). This may be done in any suitable way, for example, by determining whether the concentration of oxygen in the landfill gas collected from the plurality of wells is greater than an upper endpoint of the global range or less than a lower endpoint of the global range. The concentration of oxygen in the landfill gas is inversely proportional to methane concentration of the landfill gas (which is proportional to energy content). Therefore, it may be advantageous to control extraction of landfill gas from the plurality of wells using oxygen concentration as a basis for determining whether to adjust flow rates of landfill gas extraction in order to ensure the quality of landfill gas being extracted from the plurality of wells is of sufficient quality.

Although in the illustrated embodiment, the measure of oxygen concentration of landfill gas collected from the plurality of wells is compared to a global range to determine whether the measure of oxygen concentration is outside of the global range, it should be appreciated that the measure of oxygen concentration may be assessed in one or more other ways, such as by comparing the measure of oxygen concentration to a target value to determine whether the measure of oxygen concentration is different than the target value or comparing the measure of oxygen concentration to an upper and/or lower threshold to determine whether the measure of oxygen concentration is greater than an upper threshold or less than a lower threshold.

When, at act 804, the multi-well controller determines that the measure of oxygen concentration of the landfill gas collected from the plurality of wells is not outside of the global range, the process 800 returns through the no branch back to act 802 where another measure of oxygen concentration of the landfill gas collected from the plurality of wells is obtained. Alternatively, the process may end.

When, at act 804, the multi-well controller determines that the measure of oxygen concentration of the landfill gas collected from the plurality of wells is outside of the global range, the determination may indicate that the landfill gas collected from the plurality of wells is of insufficient quality, and that one or more of the plurality of wells should be adjusted. The process 800 therefore proceeds to act 808 where a local level controller determines whether to adjust a first well of the plurality of wells. Although acts 806-810 are described with reference to a first well of the plurality of wells, it should be appreciated that the method may be performed for any number of the plurality of wells (e.g., each of the plurality of wells, a subset of the plurality of wells).

At act 806, a measure of oxygen concentration of landfill gas collected from the first well is obtained by a local level controller. In some embodiments, act 806 may comprise operating a sensor to obtain a measure of oxygen concentration of landfill gas collected from the first well. In some embodiments, act 806 may comprise obtaining the measure of oxygen concentration of landfill gas collected from the first well from a sensor. In some embodiments, the measure of oxygen concentration of the landfill gas collected from the first well may be a measurement obtained at a previous time, for example, before one or more of acts 802-804.

At act 808 the local level controller determines whether to adjust a flow rate of landfill gas being extracted from the first well based on the measure of oxygen concentration of landfill gas collected from the first well. In some embodiments, act 808 may comprise determining whether the measure of oxygen concentration of landfill gas collected from the first well is outside of a local range for oxygen concentration (e.g., 0%-5% by volume, 0%-1% by volume, 0%-0.2% by volume, and/or any other suitable target range within these ranges). In some embodiments, the local range may be the same as the global range. In some embodiments, the local range may differ from the global range and further. In some embodiments, an upper endpoint of the local range may be greater than an upper endpoint of the global range. In other embodiments, act 808 may comprise determining whether the measure of oxygen concentration of landfill gas collected from the first well is different than a target value, greater than an upper threshold, and/or less than a lower threshold.

When, at act 808, the local level controller determines that the measure of oxygen concentration of the landfill gas collected from the first well is not outside of the local range, the process 800 returns through the no branch back to act 802 where another measure of oxygen concentration of the landfill gas collected from the plurality of wells is obtained. Alternatively, the process may end.

When, at act 808, the local level controller determines that the measure of oxygen concentration of the landfill gas collected from the first well is outside of the local range, the determination may indicate that the landfill gas collected from the first well should be adjusted, and the process proceeds through the yes branch to act 810 where the flow rate of landfill gas being extracted from the first well is adjusted. After adjusting the flow rate of the first well at act 810, the process returns to act 802 to obtain another measure of concentration of the oxygen concentration of landfill gas collected from the plurality of wells, or, alternatively, the process may end.

Figure 8B:
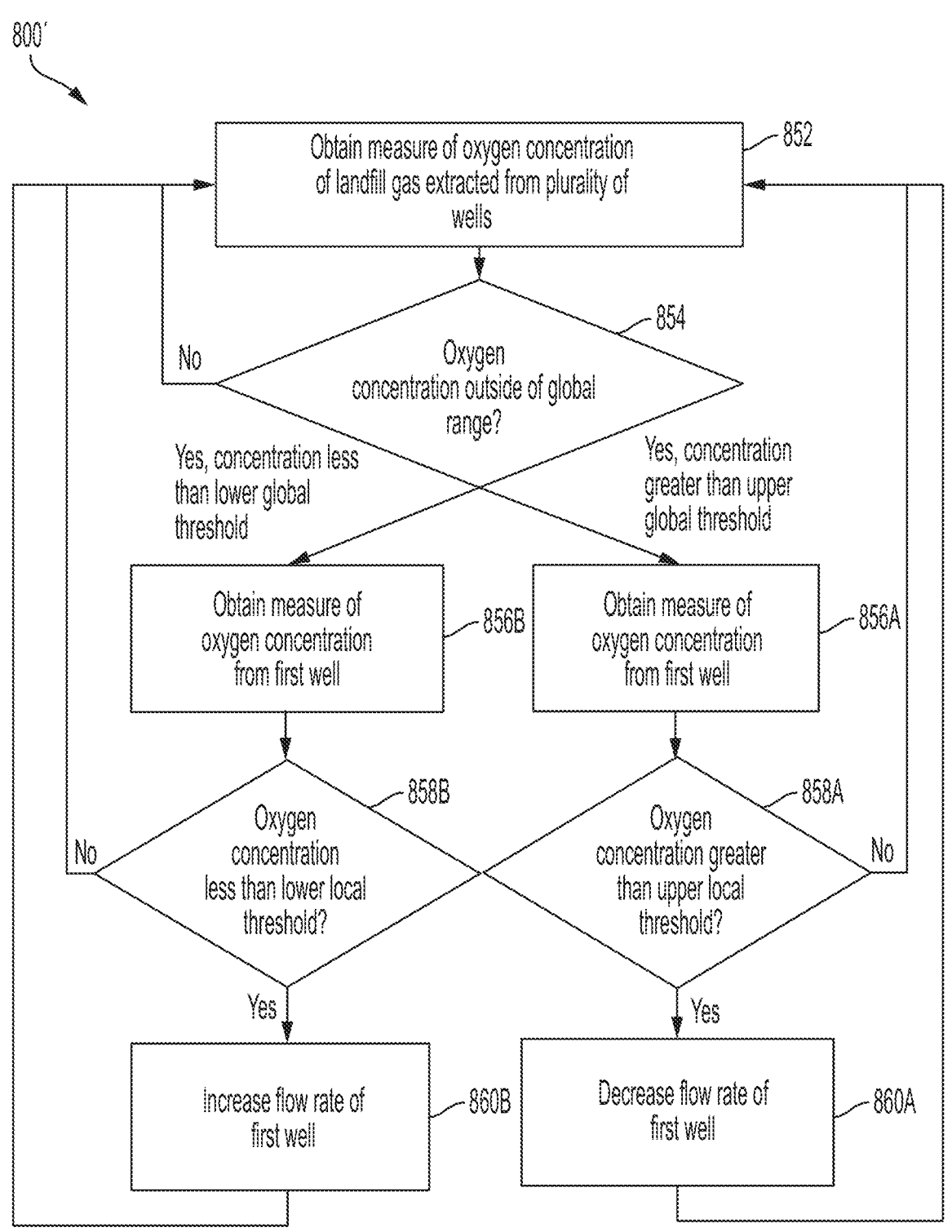
FIG. 8B is a flowchart of another illustrative process for controlling extraction of landfill gas through a gas extraction system, according to some embodiments.

FIG. 8B is a flowchart of another illustrative process for controlling extraction of landfill gas through a gas extraction system, according to some embodiments. In particular, FIG. 8B further illustrates how adjustments may be made to the first well according to process 800. Process 800' may be performed at least in part by using multi-well controller 616 and multiple local controllers 610A-C described above with reference to FIG. 6.

Process 800' begins at act 852 where a measure of oxygen concentration of landfill gas collected from a plurality of wells is obtained by a multi-level controller. At act 854, the multi-well controller determines whether the measure of oxygen concentration obtained at act 852 is outside of a global range for oxygen concentration. When, at act 854, the multi-well controller determines that the measure of oxygen concentration obtained at act 854 is not outside of the global range, the process proceeds through the no branch to return to act 852, or alternatively, to end. When, at act 854, the multi-well controller determines that the measure of oxygen concentration obtained at act 854 is outside of the global range, the process proceeds to one of acts 856A-B depending on whether the oxygen concentration is greater than an upper endpoint of the global range (i.e. oxygen concentration is too high) or less than a lower endpoint of the global range (i.e. oxygen concentration is too low).

When the multi-well controller determines that the measure of oxygen concentration obtained at act 854 is outside of the global range because it is greater than the global range (e.g., greater than an upper endpoint of the global range), the determination may indicate that the oxygen concentration of the landfill gas collected from the plurality of wells is too high and should be decreased by adjusting the flow rate of one or more of the plurality of wells. In that case, the process 800' proceeds to act 856A where a local level controller determines which of the one or more wells to adjust. Limiting the amount of oxygen in the extracted landfill gas may be helpful because high amounts of oxygen may negatively influence how generators run, for example, by causing engine problems or contributing to fires deep within the landfill. Limits on the concentration of oxygen may be imposed by landfill operators, power utility operators, local regulations, state regulations, and/or federal regulations.

In some embodiments, when oxygen concentration of aggregate landfill gas is determined to be too high, it may be most efficient to adjust flow rates of the gas extraction wells having the highest oxygen concentration by decreasing a flow rate of the one or more wells with the highest oxygen concentration. Decreasing the flow rate of landfill gas being extracted from a well causes the landfill to pull less oxygen from the atmosphere into the landfill gas stream. The decreased amounts of oxygen in the landfill gas stream result in increased methane concentration levels, with methane concentration being inversely proportional to oxygen concentration. Decreasing flow rates of gas extraction wells having the highest oxygen concentration may allow for efficiently decreasing oxygen concentration and increasing aggregate landfill gas quality.

In some embodiments, determining which gas extraction wells have the highest oxygen concentration may comprise determining whether one or more wells of the plurality of wells have an oxygen concentration greater than an upper local threshold. Thus, in the illustrated embodiment, process 800' proceeds to act 856A where a measure of oxygen concentration of landfill gas collected from a first well is obtained by a local level controller. Although acts 856A-858A are described with reference to a first well of the plurality of wells, it should be appreciated that the method may be performed for any number of the plurality of wells (e.g., each of the plurality of wells, a subset of the plurality of wells including a second well).

At act 858A, the local level controller determines whether the measure oxygen concentration obtained at act 856A is greater than an upper local threshold for oxygen concentration. When the local level controller determines that the measure of oxygen concentration obtained at act 856A is greater than the upper local threshold, the determination may indicate that a flow rate of the landfill gas being extracted from the first well should be adjusted, and the process proceeds through the yes branch to act 860A to decrease the flow rate of the first well. When the local level controller determines that the measure of oxygen concentration obtained at act 856A is not greater than the upper local threshold, the process returns through the no branch to act 852, or alternatively, may end.

When the multi-level controller determines that the measure of oxygen concentration obtained at act 854 is outside of the global range because it is less than the global range (e.g., less than a lower endpoint of the global range), the determination may indicate that the oxygen concentration of the landfill gas collected from the plurality of wells is too low and should be increased by adjusting the flow rate of one or more of the plurality of wells. In that case the process 800' proceeds to act 856B to determine which of the one or more wells to adjust. In some embodiments, when oxygen concentration of aggregate landfill gas is determined to be too low, it may be most efficient to adjust flow rates of the gas extraction wells having the lowest oxygen concentration by increasing a flow rate of the one or more wells with the lowest oxygen concentration. Increasing the flow rate of landfill gas being extracted from a well causes the landfill to pull more oxygen from the atmosphere into the landfill gas stream. The increased amounts of oxygen in the landfill gas stream result in decreased methane concentration levels, with methane concentration of the landfill gas being inversely proportional to oxygen concentration. Increasing flow rates of gas extraction wells having the highest oxygen concentration may allow for efficiently increasing oxygen concentration without sacrificing aggregate landfill gas quality.

In some embodiments, determining which gas extraction wells have the lowest oxygen concentration may comprise determining whether one or more wells of the plurality of wells have an oxygen concentration less than a lower local threshold. Thus, in the illustrated embodiment, process 800' proceeds to act 856B where a measure of oxygen concentration of landfill gas collected from a first well is obtained. Although acts 856B-858B are described with reference to a first well of the plurality of wells, it should be appreciated that the method may be performed for any number of the plurality of wells (e.g., each of the plurality of wells, a subset of the plurality of wells including a second well).

At act 858B, the local level controller determines whether the measure oxygen concentration obtained at act 856B is greater than an upper local threshold for oxygen concentration. When the local level controller determines that the measure of oxygen concentration obtained at act 856B is less than the lower local threshold, the determination may indicate that a flow rate of the landfill gas being extracted from the first well should be adjusted, and the process proceeds through the yes branch to act 860B to decrease the flow rate of the first well. When the local level controller determines that the measure of oxygen concentration obtained at act 856B is not less than the lower local threshold, the process returns through the no branch to act 852, or alternatively, may end.

Figure 9A:
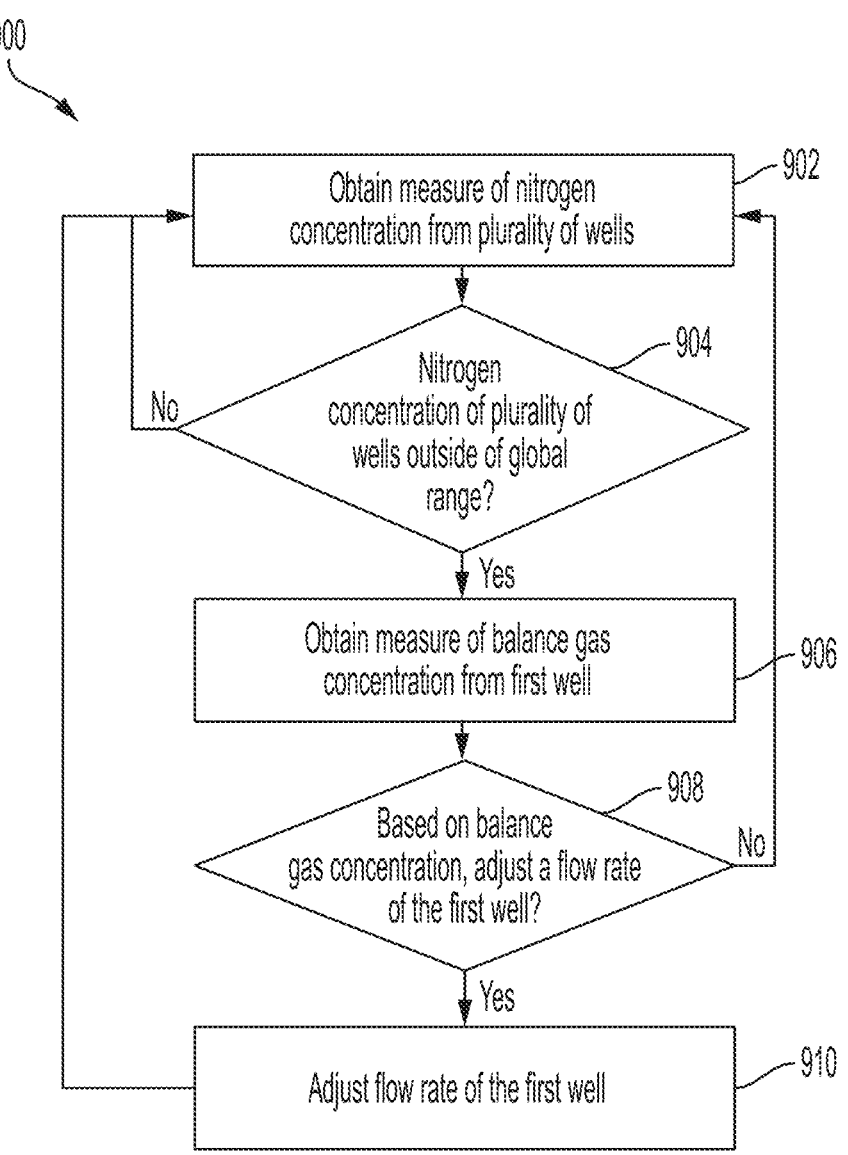
FIG. 9A is a flowchart of another illustrative process for controlling extraction of landfill gas through a gas extraction system, according to some embodiments.

FIG. 9A is a flowchart of another illustrative process for controlling extraction of landfill gas through a gas extraction system, according to some embodiments. In particular, FIG. 9A illustrates an example process 900 for site-level control of landfill gas extraction using nitrogen concentration as a top level parameter and balance gas concentration as a secondary parameter. Process 900 may be performed at least in part by using multi-well controller 616 and multiple local controllers 610A-C described above with reference to FIG. 6.

As shown in FIG. 9A, process 900 begins with act 902, where a measure of nitrogen concentration of landfill gas collected from a plurality of wells is obtained by a multi-well controller. At act 904, the multi-well controller determines whether the nitrogen concentration of the landfill gas collected from the plurality of wells is outside of a global range (e.g., 0%-5% by volume, 0%-2.5% by volume, 0%-1% by volume, and/or any other suitable target range within these ranges), for example, by determining whether the nitrogen concentration of the landfill gas collected from the plurality of wells is greater than an upper endpoint of the global range or less than a lower endpoint of the global range. The nitrogen concentration of the landfill gas is inversely proportional to methane concentration of the landfill gas (which is proportional to energy content). Therefore, it may be advantageous to control extraction of landfill gas from the plurality of wells using nitrogen concentration as a basis for determining whether to adjust flow rates of landfill gas being extraction from the plurality of wells in order to ensure the quality of landfill gas being extracted from the plurality of wells is of sufficient quality.

Although in the illustrated embodiment, the measure of nitrogen concentration of landfill gas collected from the plurality of wells is compared to a global range to determine whether the measure of nitrogen concentration is outside of the global range, it should be appreciated that the measure of nitrogen concentration may be assessed in one or more other manners, such as by comparing the measure of nitrogen concentration to a target value to determine whether the measure of nitrogen concentration is different than the target value or comparing the measure of nitrogen concentration to an upper and/or lower threshold to determine whether the measure of nitrogen concentration is greater than an upper threshold or less than a lower threshold.

When, at act 904, the multi-well controller determines that the measure of nitrogen concentration of the landfill gas collected from the plurality of wells is not outside of the global range, the process 900 returns through the no branch back to act 902 where another measure of nitrogen concentration of the landfill gas collected from the plurality of wells is obtained. Alternatively, the process may end.

When, at act 904, the multi-well controller determines that the measure of nitrogen concentration of the landfill gas collected from the plurality of wells is outside of the global range, the determination may indicate that the landfill gas collected from the plurality of wells is of insufficient quality, and that one or more of the plurality of wells should be adjusted. The process 900 therefore proceeds to act 908 to determine whether to adjust a first well of the plurality of wells. Although acts 906-910 are described with reference to a first well of the plurality of wells, it should be appreciated that the method may be performed for any number of the plurality of wells (e.g., each of the plurality of wells, a subset of the plurality of wells).

At act 906, a measure of balance gas concentration of landfill gas collected from the first well is obtained by a local level controller. In some embodiments, act 906 may comprise receiving a measure of balance gas concentration obtained indirectly (e.g., by measuring concentrations of other constituent gasses in landfill gas such as methane, oxygen, and carbon dioxide and estimating the remaining concentration as the balance gas, for example, by estimating the concentration of the balance gas as 100%−concentration of methane−concentration of oxygen−concentration of carbon dioxide). In some embodiments, the measure of balance gas concentration of the landfill gas collected from the first well may be a measurement obtained at a previous time, for example, before one or more of acts 902-904.

At act 908 the local level controller determines whether to adjust a flow rate of landfill gas being extracted from the first well based on the measure of balance gas concentration of landfill gas collected from the first well. In some embodiments, act 908 may comprise determining whether the measure of balance gas concentration of landfill gas collected from the first well is outside of a local range for balance gas concentration (e.g., 0%-5% by volume, 0%-2.5% by volume, 0%-1% by volume, and/or any other suitable target range within these ranges). In other embodiments, act 908 may comprise determining whether the measure of balance gas concentration of landfill gas collected from the first well is different than a target value, greater than an upper threshold, and/or less than a lower threshold.

When, at act 908, the local level controller that the measure of balance gas concentration of the landfill gas collected from the first well is not outside of the local range, the process 900 returns through the no branch back to act 902 where another measure of nitrogen concentration of the landfill gas collected from the plurality of wells is obtained. Alternatively, the process may end.

When, at act 908, the local level controller determines that the measure of balance gas concentration of the landfill gas collected from the first well is outside of the local range, the determination may indicate that the landfill gas collected from the first well should be adjusted, and the process proceeds through the yes branch to act 910 where the flow rate of landfill gas being extracted from the first well may be adjusted. After adjusting the flow rate of the first well at act 910, the process returns to act 902 to obtain another measure of concentration of the nitrogen concentration of landfill gas collected from the plurality of wells, or, alternatively, the process may end.

Figure 9B:
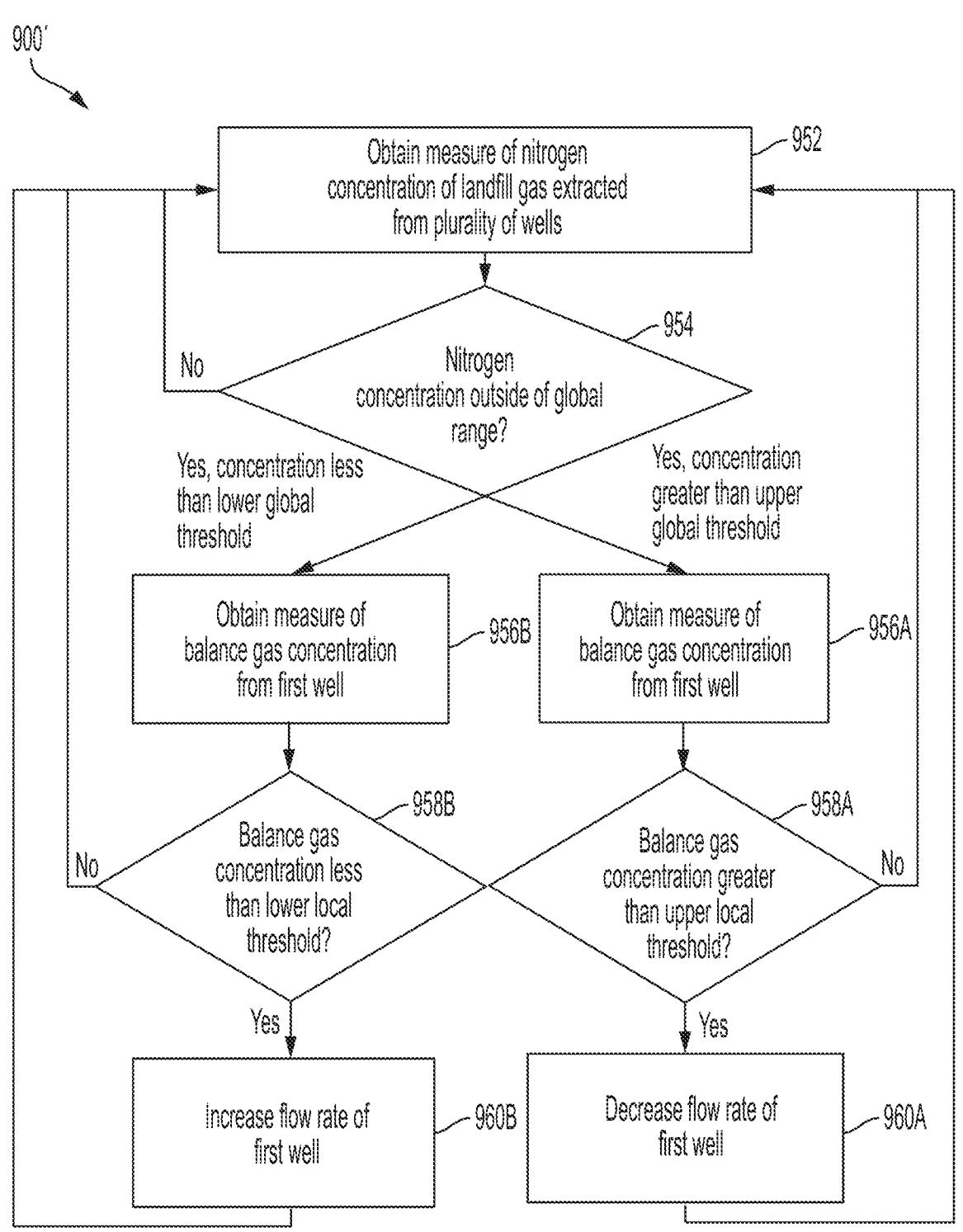
FIG. 9B is a flowchart of another illustrative process for controlling extraction of landfill gas through a gas extraction system, according to some embodiments.

FIG. 9B is a flowchart of another illustrative process for controlling extraction of landfill gas through a gas extraction system, according to some embodiments. In particular, FIG. 9B further illustrates how adjustments may be made to the first well according to process 900. Process 900' may be performed at least in part by using multi-well controller 616 and multiple local controllers 610A-C described above with reference to FIG. 6.

Process 900' begins at act 952 where a measure of nitrogen concentration of landfill gas collected from a plurality of wells is obtained by a multi-well controller. At act 954, the multi-well controller determines whether the measure of nitrogen concentration obtained at act 952 is outside of a global range for nitrogen concentration. When, at act 954, the multi-well controller determines that the measure of nitrogen concentration obtained at act 954 is not outside of the global range, the process proceeds through the no branch to return to act 952, or alternatively, to end. When, at act 954, the multi-well controller determines that the measure of nitrogen concentration obtained at act 954 is outside of the global range, the process proceeds to one of acts 956A-B depending on whether the nitrogen concentration is greater than an upper endpoint of the global range (i.e. nitrogen concentration is too high) or less than a lower endpoint of the global range (i.e. nitrogen concentration is too low).

When the multi-well controller determines that the measure of nitrogen concentration obtained at act 954 is outside of the global range because it is greater than the global range (e.g., greater than an upper endpoint of the global range), the determination may indicate that the nitrogen concentration of the landfill gas collected from the plurality of wells is too high and should be decreased by adjusting the flow rate of one or more of the plurality of wells. In that case the process 900' proceeds to act 956A where a local level controller determines which of the one or more wells to adjust. In some embodiments, when the multi-well controller determines nitrogen concentration of aggregate landfill gas to be too high, it may be most efficient to adjust flow rates of the gas extraction wells having the highest balance gas concentration, balance gas concentration being proportional to nitrogen concentration, by decreasing a flow rate of the one or more wells with the highest balance gas concentration. Decreasing the flow rate of landfill gas being extracted from a well causes the nitrogen concentration of the landfill gas stream to decrease as described herein.

In some embodiments, determining which gas extraction wells have the highest balance gas concentration may comprise determining whether one or more wells of the plurality of wells have a balance gas concentration greater than an upper local threshold. Thus, process 900' may proceed to act 956A where a measure of balance gas concentration of landfill gas collected from a first well is obtained. Although acts 956A-958A are described with reference to a first well of the plurality of wells, it should be appreciated that the method may be performed for any number of the plurality of wells (e.g., each of the plurality of wells, a subset of the plurality of wells including a second well).

At act 958A, the local level controller determines whether the measure of balance gas concentration obtained at act 956A is greater than an upper local threshold for balance gas concentration. When the local level controller determines that the measure of balance gas concentration obtained at act 956A is greater than the upper local threshold, the determination may indicate that a flow rate of the landfill gas being extracted from the first well should be adjusted. Thus, in the illustrated embodiment, the process proceeds through the yes branch to act 960A where the local level controller decreases the flow rate of the first well. When the local level controller determines that the measure of balance gas concentration obtained at act 956A is not greater than the upper local threshold, the process returns through the no branch to act 952, or alternatively, may end.

When the local level controller determines that the measure of nitrogen concentration obtained at act 954 is outside of the global range because it is less than the global range (e.g., less than a lower endpoint of the global range), the determination may indicate that the nitrogen concentration of the landfill gas collected from the plurality of wells is too low and should be increased by adjusting the flow rate of one or more of the plurality of wells. In that case, the process 900' proceeds to act 956B where the local level controller determines which of the one or more wells to adjust. In some embodiments, when nitrogen concentration of aggregate landfill gas is determined to be too low, it may be most efficient to adjust flow rates of the gas extraction wells having the lowest balance gas concentration by increasing a flow rate of the one or more wells with the lowest balance gas concentration. Increasing the flow rate of landfill gas being extracted from a well causes the nitrogen concentration of the landfill gas stream to increase as described herein.

In some embodiments, determining which gas extraction wells have the lowest nitrogen concentration may comprise determining whether one or more wells of the plurality of wells have a balance gas concentration less than a lower local threshold. Thus, in the illustrated embodiment, process 900' proceeds to act 956B where a measure of balance gas concentration of landfill gas collected from a first well is obtained by the local level controller. Although acts 956B-958B are described with reference to a first well of the plurality of wells, it should be appreciated that the method may be performed for any number of the plurality of wells (e.g., each of the plurality of wells, a subset of the plurality of wells including a second well).

At act 958B, the local level controller determines whether the measure balance gas concentration obtained at act 956B is greater than an upper local threshold for balance gas concentration. When the local level controller determines that the measure of balance gas concentration obtained at act 956B is less than the lower local threshold, the determination may indicate that a flow rate of the landfill gas being extracted from the first well should be adjusted, and the process therefore proceeds through the yes branch to act 960B where the local level controller decreases the flow rate of the first well. When the local level controller determines that the measure of balance gas concentration obtained at act 956B is not less than the lower local threshold, the process returns through the no branch to act 952, or alternatively, may end.

Figure 10A:
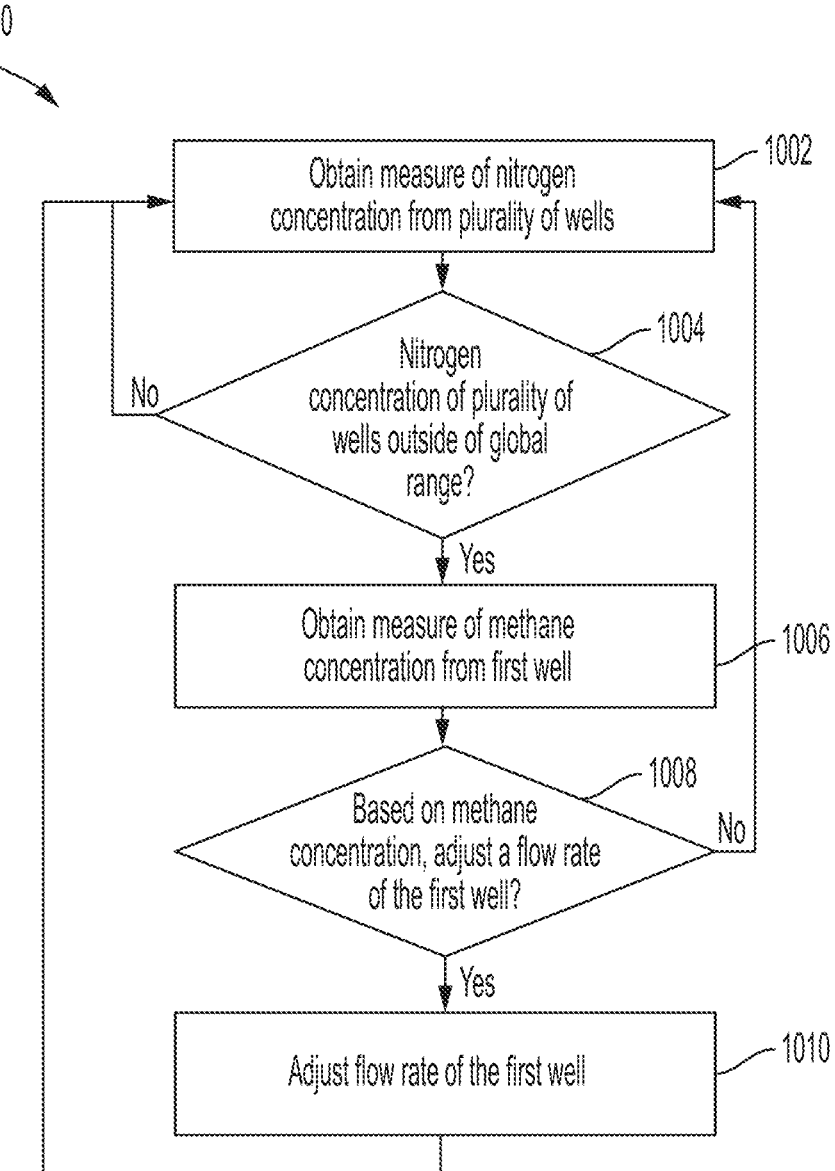
FIG. 10A is a flowchart of another illustrative process for controlling extraction of landfill gas through a gas extraction system, according to some embodiments.

FIG. 10A is a flowchart of another illustrative process for controlling extraction of landfill gas through a gas extraction system, according to some embodiments. In particular, FIG. 10A illustrates an example process 1000 for site-level control of landfill gas extraction using nitrogen concentration as a top level parameter and methane concentration as a secondary parameter. Process 1000 may be performed at least in part by using multi-well controller 616 and multiple local controllers 610A-C described above with reference to FIG. 6.

As shown in FIG. 10A, process 1000 begins with act 1002, where a measure of nitrogen concentration of landfill gas collected from a plurality of wells is obtained by a multi-well controller. At act 1004, the multi-well controller determines whether the nitrogen concentration of the landfill gas collected from the plurality of wells is outside of a global range (e.g., 0%-5% by volume, 0%-2.5% by volume, 0%-1% by volume, and/or any other suitable target range within these ranges), for example, by determining whether the nitrogen concentration of the landfill gas collected from the plurality of wells is greater than an upper endpoint of the global range or less than a lower endpoint of the global range.

Although in the illustrated embodiment, the measure of nitrogen concentration of landfill gas collected from the plurality of wells is compared to a global range to determine whether the measure of nitrogen concentration is outside of the global range, it should be appreciated that the measure of nitrogen concentration may be assessed in one or more other manners, such as by comparing the measure of nitrogen concentration to a target value to determine whether the measure of nitrogen concentration is different than the target value or comparing the measure of nitrogen concentration to an upper and/or lower threshold to determine whether the measure of nitrogen concentration is greater than an upper threshold or less than a lower threshold.

When, at act 1004, the multi-well controller determines that the measure of nitrogen concentration of the landfill gas collected from the plurality of wells is not outside of the global range, the process 1000 returns through the no branch back to act 1002 where another measure of nitrogen concentration of the landfill gas collected from the plurality of wells is obtained. Alternatively, the process may end.

When, at act 1004, the multi-well controller determines that the measure of nitrogen concentration of the landfill gas collected from the plurality of wells is outside of the global range, the determination may indicate that the landfill gas collected from the plurality of wells is of insufficient quality, and that one or more of the plurality of wells should be adjusted. The process 1000 therefore proceeds to act 1008 where a local level controller determines whether to adjust a first well of the plurality of wells. Although acts 1006-1010 are described with reference to a first well of the plurality of wells, it should be appreciated that the method may be performed for any number of the plurality of wells (e.g., each of the plurality of wells, a subset of the plurality of wells).

At act 1006, a measure of methane concentration of landfill gas collected from the first well is obtained by the local level controller. In some embodiments, act 1006 may comprise operating a sensor to obtain a measure of methane concentration of landfill gas collected from the first well. In some embodiments, act 1006 may comprise obtaining the measure of methane concentration of landfill gas collected from the first well from a sensor. In some embodiments, the measure of methane concentration of the landfill gas collected from the first well may be a measurement obtained at a previous time, for example, before one or more of acts 1002-1004.

At act 1008 the local level controller determines whether to adjust a flow rate of landfill gas being extracted from the first well based on the measure of methane concentration of landfill gas collected from the first well. In some embodiments, act 1008 may comprise determining whether the measure of methane concentration of landfill gas collected from the first well is outside of a local range for methane concentration ((e.g., 30%-65% by volume, 40%-60% by volume, 45-55% by volume, and/or any other suitable target range within these ranges). In other embodiments, act 1008 may comprise determining whether the measure of methane concentration of landfill gas collected from the first well is different than a target value, greater than an upper threshold, and/or less than a lower threshold.

When, at act 1008, the local level controller determines that the measure of methane concentration of the landfill gas collected from the first well is not outside of the local range, the process 1000 returns through the no branch back to act 1002 where another measure of nitrogen concentration of the landfill gas collected from the plurality of wells is obtained. Alternatively, the process may end.

When, at act 1008, the local level controller determines that the measure of methane concentration of the landfill gas collected from the first well is outside of the local range, the determination may indicate that the landfill gas collected from the first well should be adjusted, and the process therefore proceeds through the yes branch to act 1010 where the flow rate of landfill gas being extracted from the first well is adjusted by the local level controller. After adjusting the flow rate of the first well at act 1010, the process returns to act 1002 to obtain another measure of concentration of the nitrogen concentration of landfill gas collected from the plurality of wells, or, alternatively, the process may end.

Figure 10B:
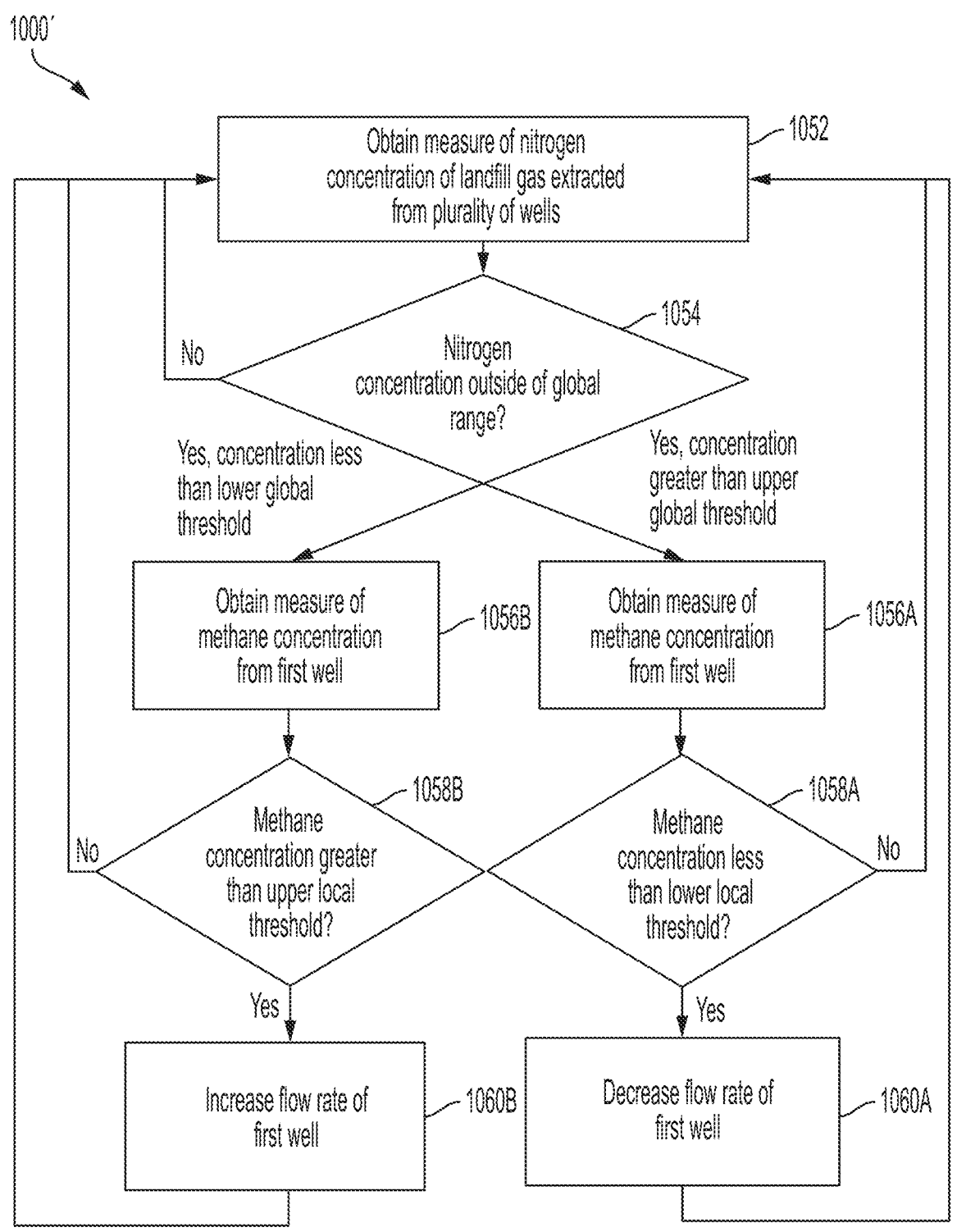
FIG. 10B is a flowchart of another illustrative process for controlling extraction of landfill gas through a gas extraction system, according to some embodiments.

FIG. 10B is a flowchart of another illustrative process for controlling extraction of landfill gas through a gas extraction system, according to some embodiments. In particular, FIG. 10B further illustrates how adjustments may be made to the first well according to process 1000. Process 1000' may be performed at least in part by using multi-well controller 616 and multiple local controllers 610A-C described above with reference to FIG. 6.

Process 1000' begins at act 1052 where a measure of nitrogen concentration of landfill gas collected from a plurality of wells is obtained by a multi-well controller. At act 1054, the multi-well controller determines whether the measure of nitrogen concentration obtained at act 1052 is outside of a global range for nitrogen concentration. When, at act 1054, the multi-well controller determines that the measure of nitrogen concentration obtained at act 1054 is not outside of the global range, the process proceeds through the no branch to return to act 1052, or alternatively, to end. When, at act 1054, the multi-well controller determines that the measure of nitrogen concentration obtained at act 1054 is outside of the global range, the process proceeds to one of acts 1056A-B depending on whether the nitrogen concentration is greater than an upper endpoint of the global range (i.e. nitrogen concentration is too high) or less than a lower endpoint of the global range (i.e. nitrogen concentration is too low).

When the multi-well controller determines that the measure of nitrogen concentration obtained at act 1054 is outside of the global range because it is greater than the global range (e.g., greater than an upper endpoint of the global range), the determination may indicate that the nitrogen concentration of the landfill gas collected from the plurality of wells is too high and should be decreased by adjusting the flow rate of one or more of the plurality of wells. In that case the process 1000' proceeds to act 1056A where a local level controller determines which of the one or more wells to adjust. In some embodiments, when nitrogen concentration of aggregate landfill gas is determined to be too high, it may be most efficient to adjust flow rates of the gas extraction wells having the lowest methane concentration by decreasing a flow rate of the one or more wells with the lowest methane concentration. Decreasing the flow rate of landfill gas being extracted from a well causes the nitrogen concentration of the landfill gas stream to decrease and methane concentration to increase.

In some embodiments, determining which gas extraction wells have the lowest methane concentration may comprise determining whether one or more wells of the plurality of wells have a methane concentration less than a local threshold. Thus, in the illustrated embodiment, the method 1000' proceeds to act 1056A where a measure of methane concentration of landfill gas collected from a first well is obtained by the local level controller. Although acts 1056A-1058A are described with reference to a first well of the plurality of wells, it should be appreciated that the method may be performed for any number of the plurality of wells (e.g., each of the plurality of wells, a subset of the plurality of wells including a second well).

At act 1058A, the local level controller determines whether the measure methane concentration obtained at act 1056A is less than a lower local threshold for methane concentration. When the local level controller determines that the measure of methane concentration obtained at act 1056A is less than the lower local threshold, the determination may indicate that a flow rate of the landfill gas being extracted from the first well should be adjusted. In the illustrated embodiment, the process proceeds through the yes branch to act 1060A where the local level controller decreases the flow rate of the first well. When the local level controller determines that the measure of methane concentration obtained at act 1056A is not less than the lower local threshold, the process returns through the no branch to act 1052, or alternatively, may end.

When the multi-well controller determines that the measure of nitrogen concentration obtained at act 1054 is outside of the global range because it is less than the global range (e.g., less than a lower endpoint of the global range), the determination may indicate that the nitrogen concentration of the landfill gas collected from the plurality of wells is too low and should be increased by adjusting the flow rate of one or more of the plurality of wells. In that case the process 1000' proceeds to act 1056B where a local level controller determines which of the one or more wells to adjust. In some embodiments, when nitrogen concentration of aggregate landfill gas is determined to be too low, it may be most efficient to adjust flow rates of the gas extraction wells having the highest methane concentration by increasing a flow rate of the one or more wells with the highest methane concentration. Increasing the flow rate of landfill gas being extracted from a well causes the nitrogen concentration of the landfill gas stream to increase and the methane concentration to decrease.

In some embodiments, determining which gas extraction wells have the highest methane concentration may comprise determining whether one or more wells of the plurality of wells have a methane concentration greater than an upper local threshold. Thus, in the illustrated embodiment, process 1000' proceeds to act 1056B where a measure of methane concentration of landfill gas collected from a first well is obtained by the local level controller. Although acts 1056B-1058B are described with reference to a first well of the plurality of wells, it should be appreciated that the method may be performed for any number of the plurality of wells (e.g., each of the plurality of wells, a subset of the plurality of wells including a second well).

At act 1058B, the local level controller determines whether the measure of methane concentration obtained at act 1056B is greater than an upper local threshold for methane concentration. When the local level controller determines that the measure of methane concentration obtained at act 1056B is greater than the upper local threshold, the determination may indicate that a flow rate of the landfill gas being extracted from the first well should be adjusted, and the process therefore proceeds through the yes branch to act 1060B where the local level controller increases the flow rate of the first well. When the local level controller determines that the measure of methane concentration obtained at act 1056B is not greater than the upper local threshold, the process returns through the no branch to act 1052, or alternatively, may end.

Thus, FIGS. 7A-10B provide embodiments of site-level control methods using various characteristics of landfill gas to determine whether to adjust flow rates of a plurality of wells (as a top level parameter) and which of the plurality of wells to adjust (as a secondary parameter). However, it should be appreciated that any suitable characteristic may be used as a top level and/or secondary parameters for aggregate control of landfill gas extraction (e.g., methane concentration, energy content, oxygen concentration, nitrogen concentration, flow rate).

Figure 12:
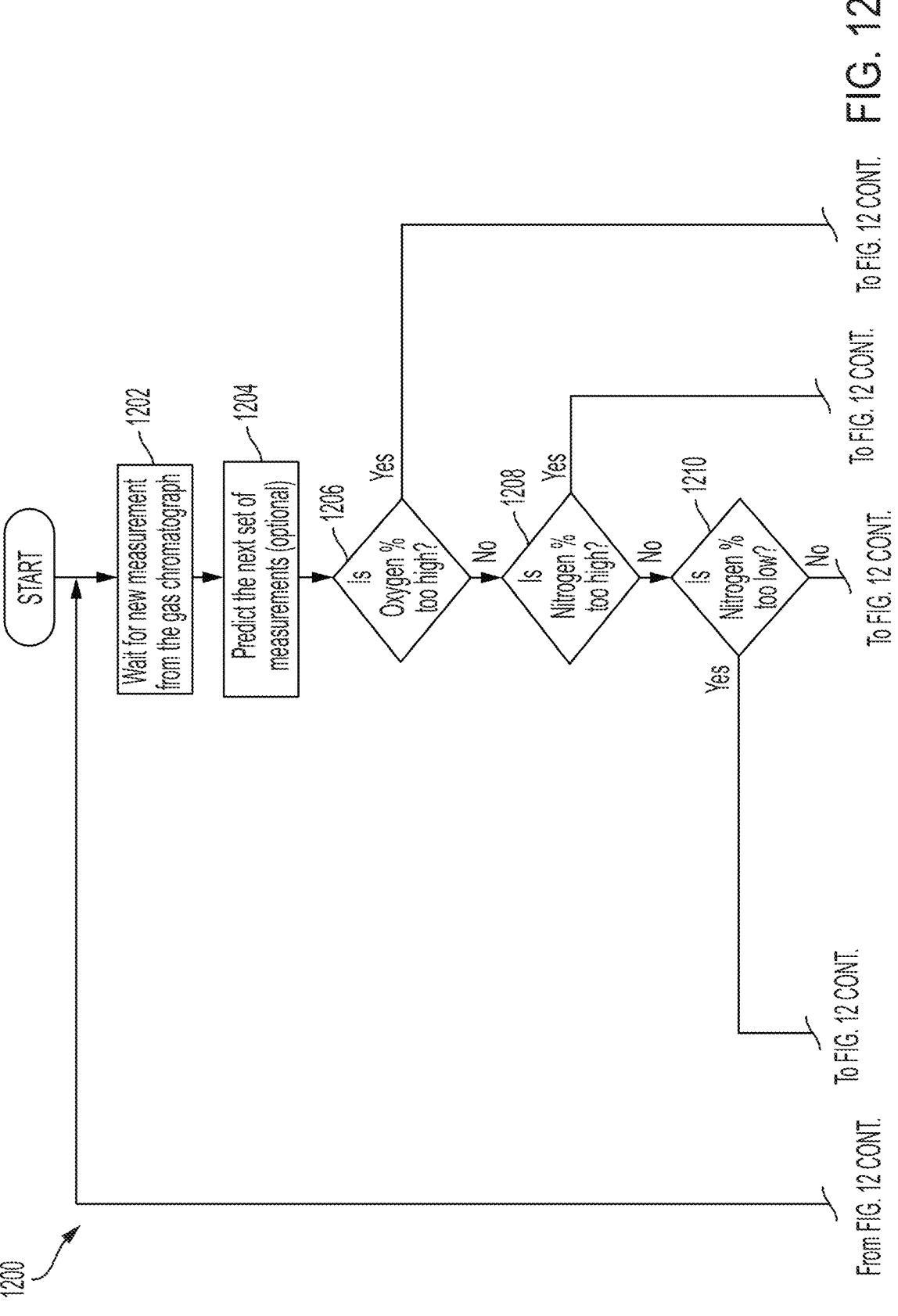
FIG. 12 is a flowchart of another illustrative process for controlling extraction of landfill gas through a gas extraction system, according to some embodiments.
Figure 12:
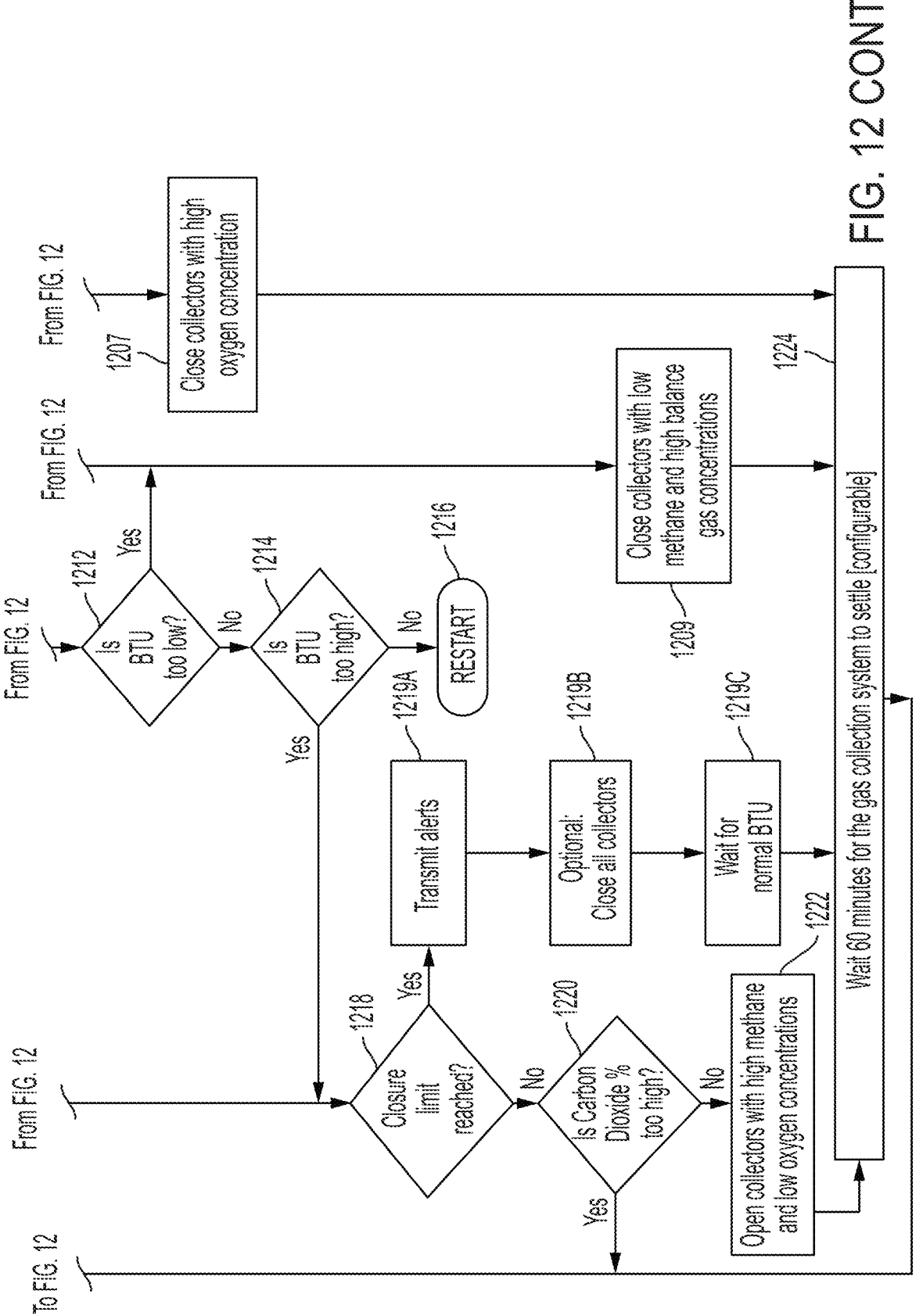

In some embodiments, methods for site-level control may provide for multiple aggregate control methods performed sequentially. For example, FIG. 12 is a flowchart of another illustrative process for controlling extraction of landfill gas through a gas extraction system illustrating the use of multiple characteristics of aggregate landfill gas to control landfill gas extraction.

Process 1200 begins at act 1202 where one or more measurements from a sensor, such as a gas chromatograph are received, for example, using a multi-well controller. In some embodiments, the one or more measurements may be measures of concentrations of constituent gasses in landfill gas collected from a plurality of wells such as oxygen, methane, nitrogen, carbon dioxide, and/or hydrogen sulfide, for example.

At act 1204, the process may optionally include predicting a next set of measurements. For example, in some embodiments, control system 500 may be configured to predict future states of the landfill under control, and/or may be configured to use such predictions to control the operation of a gas extraction system associated with the landfill under control. In some embodiments, using one or more predictions regarding the future state(s) of the landfill under control to control the operation of the gas extraction system may improve the performance (e.g., efficiency) of the gas extraction system, relative to the performance of conventional gas extraction systems. Further aspects of predictive control methods are described in U.S. Pat. No. 10,029,290, titled "DEVICES AND TECHNIQUES RELATING TO LANDFILL GAS EXTRACTION," filed on Nov. 4, 2014, which is hereby incorporated by reference in its entirety herein.

At act 1206, the multi-well controller uses a measure of oxygen concentration of the landfill gas collected from the plurality of wells obtained at act 1202 to determine whether the oxygen concentration of the landfill gas collected from the plurality of wells is too high, for example, by comparing the measure of oxygen concentration to a global range, a global target value, and/or a global upper threshold. When the multi-well controller determines, at act 1206, that the oxygen concentration of the landfill gas collected from the plurality of wells is too high, the process proceeds through the yes branch to act 1207 where the multi-well controller and/or one or more local level controllers close (e.g., decreasing flow rate of) gas extraction wells with high oxygen concentrations (e.g., gas extraction wells with oxygen concentrations above a local threshold, gas extraction wells having the relative highest oxygen concentration of the plurality of wells). Otherwise, the process proceeds through the no branch to act 1208. Although not shown in FIG. 12, process 1200 may further include determining whether the oxygen concentration of the landfill gas collected from the plurality of wells is too low, for example by comparing the measure of oxygen concentration obtained at act 1200 to a global range, a global target value, and/or a global lower threshold.

At act 1208, the multi-well controller uses a measure of nitrogen concentration of the landfill gas collected from the plurality of wells obtained at act 1202 to determine whether the nitrogen concentration of the landfill gas collected from the plurality of wells is too high, for example, by comparing the measure of nitrogen concentration to a global range, a global target value, and/or a global upper threshold. When the multi-well controller determines, at act 1208, that the nitrogen concentration of the landfill gas collected from the plurality of wells is too high, the process may proceed through the yes branch to act 1209. At act 1209, the multi-well controller and/or one or more local level controllers adjust the flow rate of one or more gas extraction wells. In some embodiments, gas extraction wells having the highest balance gas concentration may be adjusted (e.g., gas extraction wells with balance gas concentrations greater than a local threshold, gas extraction wells having the relative highest balance gas concentration) by decreasing a flow rate of such wells. In some embodiments, gas extraction wells having the lowest methane concentration may be adjusted (e.g., gas extraction wells with methane concentrations less than a local threshold, gas extraction wells having the relative lowest methane concentration) by decreasing a flow rate of such wells. Otherwise, the process proceeds through the no branch to act 1210.

At act 1210, the multi-well controller uses a measure of nitrogen concentration of the landfill gas collected from the plurality of wells obtained at act 1202 to determine whether the nitrogen concentration of the landfill gas collected from the plurality of wells is too low, for example, by comparing the measure of nitrogen concentration to a global range, a global target value, and/or a global lower threshold. When the multi-well controller determines, at act 1210, that the nitrogen concentration of the landfill gas collected from the plurality of wells is too low, the process may proceed through the yes branch to act 1222. At act 1222, the flow rate of one or more gas extraction wells may is adjusted by the multi-well controller and/or one or more local level controllers. In some embodiments, gas extraction wells having the lowest balance gas concentration may be adjusted (e.g., gas extraction wells with balance gas concentrations less than a local threshold, gas extraction wells having the relative lowest balance gas concentration) by increasing a flow rate of such wells. In some embodiments, gas extraction wells having the highest methane concentration may be adjusted (e.g., gas extraction wells with methane concentrations greater than a local threshold, gas extraction wells having the relative highest methane concentration) by increasing a flow rate of such wells. Otherwise, the process proceeds through the no branch to act 1212.

In some embodiments, before increasing a flow rate of landfill gas being extracted from one or more of the plurality of wells, the process may proceed to act 1218 where a multi-well controller and/or one or more local level controllers determine whether a closure limit of a valve of one or more gas extraction wells has been reached. If a closure limit has been reach but landfill gas quality is still inadequate, the system may require additional action be taken before continuing to extract landfill gas according to the aggregate control process. When, at act 1218, it is determined that a closure limit of a valve of one or more gas extraction wells has been reached, the process may proceed to one or more of acts 1219A-C to transmit one or more alerts that a closure limit has been reached, close all landfill gas extraction wells of the landfill, and/or to wait for a measure of energy content which is deemed to be normal (e.g., within a target range, below or above a target threshold, equal to a target value).

In some embodiments, before increasing a flow rate of landfill gas being extracted from one or more of the plurality of wells, the process may proceed to act 1220 where the multi-well controller and/or one or more local level controllers determine whether a characteristic of the landfill gas collected from the plurality of wells is too high (e.g., by comparing the characteristic to a target range, a target value, an upper threshold). For example, the process 1200 may prevent (e.g., using the multi-well controller and/or one or more local level controllers) increasing a flow rate of landfill gas being extracted from the plurality of wells when the carbon dioxide concentration of the landfill gas collected from the plurality of wells is too high to prevent further increasing the carbon dioxide concentration. In some embodiments, the characteristic may comprise nitrogen concentration, hydrogen sulfide concentration, oxygen concentration, and/or a flow rate of the landfill gas being extracted from the plurality of wells. When it is determined, at act 1220, that a characteristic of the landfill gas collected from the plurality of wells is too high, the process returns through the yes branch to act 1202.

The inventors have appreciated that the product of the flow rate of extracted landfill gas and the concentration of methane in the extracted landfill gas, which may indicate the rate of methane extraction, provides a good estimate of the energy content in the extracted landfill gas, as methane is a major source of energy extracted from landfills (e.g., energy may be generated by burning methane). Accordingly, some of the techniques developed by the inventors seek to regulate a product of methane concentration and flow rate. At act 1212, the multi-well controller uses a measure of energy content (BTU) of the landfill gas collected from the plurality of wells obtained at act 1202 to determine whether the energy content of the landfill gas collected from the plurality of wells is too low, for example, by comparing the measure of energy content to a global range, a global target value, and/or a global lower threshold. When the multi-well controller determines, at act 1212, that the energy content of the landfill gas collected from the plurality of wells is too low, the process may proceed through the yes branch to act 1209. At act 1209, the flow rate of one or more gas extraction wells is adjusted by the multi-well controller and/or one or more local level controllers. In some embodiments, gas extraction wells having the highest balance gas concentration may be adjusted (e.g., gas extraction wells with balance gas concentrations greater than a local threshold, gas extraction wells having the relative highest balance gas concentration) by decreasing a flow rate of such wells. In some embodiments, gas extraction wells having the lowest methane concentration may be adjusted (e.g., gas extraction wells with methane concentrations less than a local threshold, gas extraction wells having the relative lowest methane concentration) by decreasing a flow rate of such wells. Otherwise, the process may proceed through the no branch to act 1214.

At act 1214, the multi-well controller uses a measure of energy content (BTU) of the landfill gas collected from the plurality of wells obtained at act 1202 to determine whether the energy content of the landfill gas collected from the plurality of wells is too high, for example, by comparing the measure of energy content to a global range, a global target value, and/or a global upper threshold. When it is determined, at act 1212, that the energy content of the landfill gas collected from the plurality of wells is too high, the process proceeds through the yes branch to act 1222. In some embodiments, the process may first proceed to acts 1218 and/or 1220 before proceeding to act 1222, as described herein. At act 1222, the flow rate of one or more gas extraction wells is adjusted by the multi-well controller and/or one or more local level controllers. In some embodiments, gas extraction wells having the lowest balance gas concentration may be adjusted (e.g., gas extraction wells with balance gas concentrations less than a local threshold, gas extraction wells having the relative lowest balance gas concentration) by increasing a flow rate of such wells. In some embodiments, gas extraction wells having the highest methane concentration may be adjusted (e.g., gas extraction wells with methane concentrations greater than a local threshold, gas extraction wells having the relative highest methane concentration) by increasing a flow rate of such wells. The process then proceeds through the no branch to act 1224 where the system may wait a predetermined period of time (e.g., 60 minutes) before returning to act 1202 to obtain another set of measurements from one or more sensor. When, at act 1214, the multi-well controller determines that the energy content of the landfill gas collected from the plurality of wells is not too high, the process proceeds to act 1216 where the process restarts by returning to act 1202, or alternatively, may end.

As such, FIG. 12 illustrates an example of a site-level control method using multiple characteristics of collected landfill gas to control extraction of landfill gas from a plurality of wells. Although the illustrated embodiment gives a specific example where the process begins by using oxygen concentration to control extraction of landfill gas, then nitrogen concentration, and using energy content last, other orders of process 1200 are possible. In addition, in some embodiments, one or more other characteristics of the landfill gas collected from the plurality of wells may additionally or alternatively be used to control landfill gas extraction, such as methane concentration or flow rate, for example.

Well-Level Landfill Gas Extraction Control

According to some aspects of the technology described herein, landfill gas extraction from respective gas extraction wells may be controlled according to local gas extraction methods in addition or in the alternative to the site-level extraction methods described herein. For example, local gas extraction methods may be based on one or more characteristics of landfill gas extracted from an individual well.

The techniques and devices disclosed herein may be used to modulate the rate of gas extraction of a well or set of wells in accordance with any suitable control scheme. Some examples of control schemes might include, but are not limited to:

Modulation of the flow-control mechanism to maintain and/or obtain a constant vacuum pressure in the gas extraction well (in spite of varying atmospheric pressure, temperature, and/or varying rates of gas generation, etc.);

Modulation of the flow-control mechanism to maintain and/or obtain a constant flow rate of landfill gas from the extraction well;

Modulation of the flow-control mechanism to control the flow rate of landfill gas from the extraction well;

Modulation of the flow-control mechanism to maintain and/or obtain a constant percentage of any of the constituent gases (including but not limited to methane, carbon dioxide, oxygen, nitrogen, etc.) in the landfill gas coming from the extraction well;

Modulation of the flow-control mechanism to control (e.g., increase or decrease) the concentration of any of the constituent gases in the landfill gas coming from the extraction well;

Modulation of the flow-control mechanism to control (e.g., increase and/or decrease) the energy content of the landfill gas (e.g., increase the total quantity of methane extracted in a given period of time, etc.) coming from the extraction well;

Modulation of the flow-control mechanism to control the total volume of the landfill gas (e.g., increase the total quantity of landfill gas extracted in a given period of time, etc.) coming from the extraction well;

Modulation of the flow-control mechanism to increase the rate of extraction during periods of increased energy demand (e.g., increasing generation during the peaks of real time, hourly, daily, weekly, monthly, or seasonal electricity prices);

Modulation of the flow-control mechanism to decrease the rate of extraction during periods of reduced energy demand (e.g., reducing generation during the lows of real time, hourly, daily, weekly, monthly, or seasonal electricity prices);

Modulation of the flow-control mechanism to control (e.g., maintain, improve, and/or establish) the long term stability of the biochemical decomposition processes (aerobic or anaerobic digestion, etc.) occurring within the section of waste that is in the vicinity of the gas extraction well;

Modulation of the flow-control mechanism to control (e.g., increase and/or decrease) the rates of decomposition occurring within the section of waste that is in the vicinity of the gas extraction well;

Modulation of the flow-control mechanism to match the operating parameters or limitations of the gas collection system;

Modulation of the flow-control mechanism to prevent or extinguish underground fires or other potentially dangerous events occurring within the section of waste that is in the vicinity of the gas extraction well;

Modulation of the flow-control mechanism to mitigate emission of odors;

Modulation of the flow-control mechanism to control (e.g., reduce) emissions of landfill gas or components of landfill gas ($H_2S$, methane, etc.) in the vicinity of the gas extraction wells;

Modulation of the flow-control mechanism to control (e.g., reduce) gas losses into the atmosphere;

Modulation of the flow-control mechanism to control (e.g., maintain, improve, and/or establish) compliance of the gas extraction system with local, state and/or federal regulations; and/or Modulation of the flow-control mechanism to reduce damage to an engine, turbine, or other energy generation equipment from contaminants emanating from the vicinity of a gas extraction well.

Examples of local level control methods are now provided herein in further detail. Additional details of local level controls methods are further provided in U.S. Pat. No. 10,576,514, titled "DEVICES AND TECHNIQUES RELATING TO LANDFILL GAS EXTRACTION," filed on Apr. 21, 2017, which is hereby incorporated by reference in its entirety herein.

Local Level Control Methods Using Measurements of Gas Composition

In some embodiments, landfill gas extraction from a gas extraction well may be based at least in part on the composition of landfill gas collected from the gas extraction well. For example, in some embodiments, the In-Situ Control Mechanism of the gas extraction well may adjust the flow rate of the gas extraction well (e.g., by changing a degree to which a valve of the well is open) based on a measured concentration of one or more constituent gasses in the landfill gas collected from the gas extraction well.

For example, in some embodiments, a measure of a concentration of a constituent gas in landfill gas collected from a first well may be obtained and used to determine whether to adjust flow rate of the first well. In some embodiments, the concentration of the constituent gas may be compared to a target value, and a flow rate of the first well may be adjusted when the concentration of the constituent gas does not match the target value. In some embodiments, the concentration of the constituent gas may be compared to a target range, and the flow rate of the first well may be adjusted when the concentration of the constituent gas is outside of the target range. In some embodiments, the concentration of the constituent gas may be compared to an upper threshold, and the flow rate of the first well may be adjusted (e.g., to decrease the concentration of the constituent gas) when the concentration of the constituent gas is above the upper threshold. In some embodiments, the concentration of the constituent gas may be compared to a lower threshold, and the flow rate of the first well may be adjusted (e.g., to increase the concentration of the constituent gas) when the concentration of the constituent gas is below the lower threshold.

In some embodiments, the constituent gas is one of oxygen, nitrogen, and/or balance gas. In such embodiments, when it is determined to adjust a flow rate of the first well to decrease the concentration of nitrogen, oxygen, and/or balance gas, the flow rate may be decreased (e.g., by closing a valve of the first well). Further, when it is determined to adjust a flow rate of the first well to increase the concentration of oxygen, nitrogen, and/or balance gas, the flow rate may be increased (e.g., by opening a valve of the first well)

In some embodiments, the constituent gas is methane. In such embodiments, when it is determined to adjust a flow rate of the first well to decrease the concentration of methane, the flow rate may be decreased (e.g., by closing a valve of the first well). Further, when it is determined to adjust a flow rate of the first well to decrease the concentration of methane, the flow rate may be increased (e.g., by opening a valve of the first well).

Local Level Control Using Measurements of Energy Content

In some embodiments, landfill gas extraction from a gas extraction well may be based at least in part on an energy content of landfill gas collected from the gas extraction well. For example, in some embodiments, the In-Situ Control Mechanism may adjust the flow rate of the gas extraction well (e.g., by changing a degree to which a valve of the well is open) based on a measured energy content of the landfill gas collected from the gas extraction well.

In some embodiments, energy content of extracted landfill gas may be determined based on product of the flow rate of extracted landfill gas from a first well and the concentration of methane in the extracted landfill gas. The calculated measure of energy content may be used to determine whether to adjust a flow rate of the first well. In some embodiments, the measured energy content may be compared to a target value, and a flow rate of the first well may be adjusted when the measured energy content does not match the target value. In some embodiments, the concentration of the constituent gas may be compared to a target range, and the flow rate of the first well may be adjusted when the energy content is outside of the target range. In some embodiments, energy content may be compared to an upper threshold, and the flow rate of the first well may be adjusted (e.g., to decrease the energy content) when the energy content is above the upper threshold. In some embodiments, the energy content may be compared to a lower threshold, and the flow rate of the first well may be adjusted (e.g., to increase the energy content) when the energy content is below the lower threshold.

In some embodiments, a measure of energy content of landfill gas collected from a first well may be obtained prior to adjusting a flow rate of the first well (e.g., by increasing or decreasing the flow rate of the first well). Subsequently, a second measure of energy content may be obtained to determine whether the energy content of the landfill gas stream has increased or decreased as a result of adjusting the flow rate. If the result of adjusting the flow rate is desirable (e.g., increased energy content where it is desired to maximize energy content), the adjustment to the flow rate may be repeated.

Local Level Control Using Measurements of One or More Other Characteristics

In some embodiments, landfill gas extraction from a first well may be controlled based on one or more other characteristics of the landfill gas collected from the first well. For example, in some embodiments, control of landfill gas extraction may be based on a current flow rate of landfill gas extraction (e.g., as compared to a target flow rate, threshold flow rate, and/or target range for flow rates). In some embodiments, control of landfill gas extraction may be based at least in part on landfill gas temperature and/or humidity, for example, as described in U.S. patent application Ser. No. 16/290,387, titled "LANDFILL GAS EXTRACTION SYSTEMS AND METHODS," filed on Mar. 1, 2019, which is hereby incorporated by reference in its entirety herein. In some embodiments, control of landfill gas extraction may be based at least in part on pressure measurements, for example, as described in U.S. patent application Ser. No. 16/589,372, titled "LANDFILL GAS EXTRACTION CONTROL SYSTEM," filed on Oct. 1, 2019, which is hereby incorporated by reference in its entirety herein.

In some embodiments, control of landfill gas extraction may be based on one or more environmental conditions in and around the well, as described herein. In some embodiments, the In Situ Control Mechanism may be configured to control flow based on environmental data which may include information about parameters including, but not limited to atmospheric pressure, ambient temperature, wind direction, wind speed, precipitation, humidity, and/or any other suitable environmental parameter. The In Situ Control Mechanism may use information from one or more other sensors placed in or around the gas extraction well, including, without limitation, atmospheric pressure sensor(s) (sometimes termed barometric pressure sensor(s), subsurface temperature probe(s), subsurface moisture probe(s), collection well liquid level measurement sensors, measurements of the chemical and/or biological processes (for example, pH measurements, tests for the presence of other chemicals or biological by-products, etc.) occurring in the section of waste that is in the vicinity of the gas extraction well, and/or any other suitable information to determine control adjustments to be made to the flow rate of the first well.

Multi-Parameter Local Level Control Methods

Figure 11:
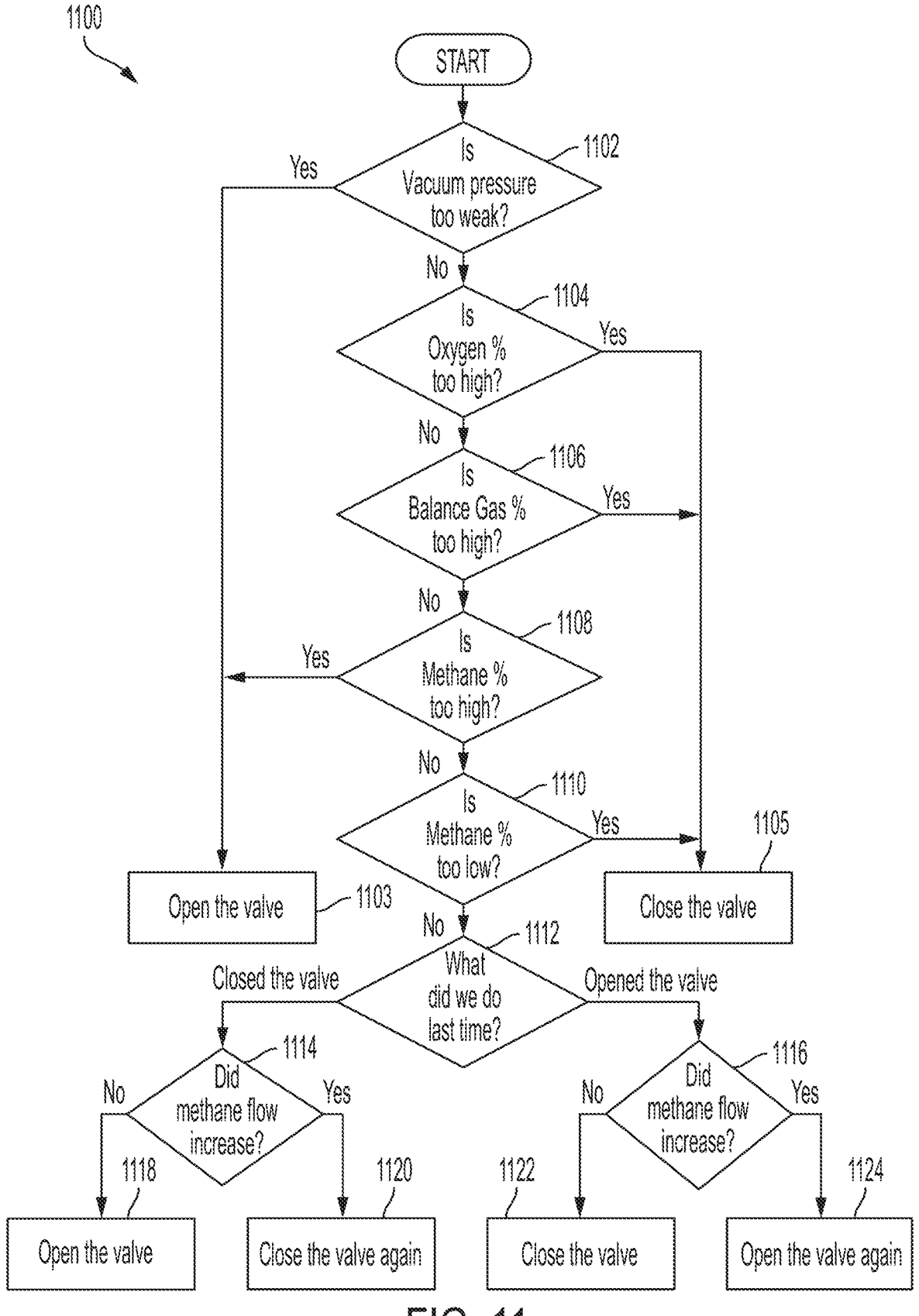
FIG. 11 is a flowchart of another illustrative process for controlling extraction of landfill gas through a gas extraction system, according to some embodiments.

In some embodiments, the techniques described herein for local level control of landfill gas extraction from a first well may be combined to provide a local level control method using multiple characteristics of landfill gas collected from the first well to determine adjustments to be made to the flow rate of landfill gas being extracted from the first well. For example, FIG. 11 illustrates an example process 1100 for local level control of landfill gas extraction from a first well. In some embodiments, the process 1100 is performed by a local level controller (e.g., one or more of local level controllers 610A-C shown in FIG. 6).

Process 1100 begins at act 1102, where it is determined whether vacuum pressure of the gas extraction well is too weak to obtain gas composition measurements. The inventors have recognized that operating the one or more gas composition sensors when the flow of the landfill gas stream is too weak may cause damage to the one or more gas composition sensors as the sample being tested by the one or more gas composition sensors may comprise mostly leachate and/or other contaminants and relatively little landfill gas. Thus, ensuring that the vacuum pressure of the gas extraction well is strong enough (e.g., above a lower threshold) before operating the one or more gas composition sensors may prevent damage to the one or more gas composition sensors. In some embodiments, act 1102 comprise obtaining at least one measure of landfill gas pressure from at least one sensor configured to measure landfill gas pressure in the gas extraction well piping at a location upstream of a valve of the gas extraction well. The measure of landfill gas pressure may be compared to a threshold pressure (e.g., by determining whether the measure of landfill gas pressure is less than or greater than the threshold pressure). In some embodiments the threshold pressure may be atmospheric pressure in a region of the landfill. In some embodiments, the threshold pressure value may be −5 mbar, −4 mbar, −3 mbar, −2 mbar, −1 mbar, 1 mbar, 2 mbar, 3 mbar, 4 mbar, or 5 mbar. When, at act 1102, it is determined that the vacuum pressure in the gas extraction well is too weak (e.g., by determining that the measure of landfill gas pressure is greater than the threshold pressure), the process proceeds through the yes branch to act 1103 to increase a flow rate of the landfill gas being extracted from the first well by opening a valve of the first well. Otherwise, the process proceeds to act 1104.

At act 1104, it is determined whether an oxygen concentration of the landfill gas collected from the first well is too high (e.g., by comparing a measure of oxygen concentration of the landfill gas collected from the first well to an upper threshold). In some embodiments, the upper threshold is 5%, 4.5%, 4%, 3.5%, 3%, 2.5%, 2%, 1.5%, 1%, 0.5% oxygen or any other suitable value including any value within the percentages described herein. When it is determined, at act 1104, that the oxygen concentration of the landfill gas collected from the first well is too high (e.g., by determining that the measure of oxygen concentration of the landfill gas collected from the first well is greater than the upper threshold), the process proceeds through the yes branch to act 1105 to decrease the concentration of oxygen in the landfill gas being extracted from the first well by closing a valve of the first well. Otherwise, the process proceeds to act 1106. Although in the illustrated embodiment act 1104 comprises determining whether the oxygen concentration of landfill gas collected from the first well is too high, in some embodiments act 1104 may additionally or alternatively comprise determining whether a measure of oxygen concentration matches a target value, is outside of a local range, and/or is less than a lower threshold.

At act 1106, it is determined whether a balance gas concentration of the landfill gas collected from the first well is too high (e.g., by comparing a measure of balance gas concentration of the landfill gas collected from the first well to an upper threshold). In some embodiments, the upper threshold is 5%, 4.5%, 4%, 3.5%, 3%, 2.5%, 2%, 1.5%, 1%, 0.5% balance gas or any other suitable value including any value within the percentages described herein. When it is determined, at act 1106, that the balance gas concentration of the landfill gas collected from the first well is too high (e.g., by determining that the measure of balance gas concentration of the landfill gas collected from the first well is greater than the upper threshold), the process proceeds through the yes branch to act 1105 to decrease the concentration of balance gas in the landfill gas being extracted from the first well by closing a valve of the first well. Otherwise, the process proceeds to act 1108. Although in the illustrated embodiment act 1106 comprises determining whether the balance gas concentration of landfill gas collected from the first well is too high, in some embodiments act 1106 may additionally or alternatively comprise determining whether a measure of oxygen concentration matches a target value, is outside of a local range, and/or is less than a lower threshold.

At act 1108, it is determined whether a methane concentration of the landfill gas collected from the first well is too high (e.g., by comparing a measure of methane concentration of the landfill gas extracted from the first well to an upper threshold). In some embodiments, the upper threshold is 55%, 56%, 57%, 58%, 59%, 60%, 61%, 62%, 63%, 64%, 65%, 66%, 67%, 68%, 69%, 70% methane or any other suitable value including any value within the percentages described herein. When it is determined, at act 1108, that the methane concentration of the landfill gas collected from the first well is too high (e.g., by determining that the measure of methane concentration of the landfill gas collected from the first well is greater than the upper threshold), the process proceeds through the yes branch to act 1103 to decrease the concentration of methane in the landfill gas being extracted from the first well by opening a valve of the first well. Otherwise, the process proceeds to act 1110.

At act 1110, it is determined whether a methane concentration of the landfill gas collected from the first well is too low (e.g., by comparing a measure of methane concentration of the landfill gas extracted from the first well to a lower threshold). In some embodiments, the lower threshold is 30%, 31%, 32%, 33%, 34%, 35%, 36%, 37%, 38%, 39%, 40%, 41%, 42%, 43%, 44%, 45% methane or any other suitable value including any value within the percentages described herein. When it is determined, at act 1110, that the methane concentration of the landfill gas collected from the first well is too low (e.g., by determining that the measure of methane concentration of the landfill gas collected from the first well is less than the lower threshold), the process proceeds through the yes branch to act 1105 to increase the concentration of methane in the landfill gas being extracted from the first well by closing a valve of the first well. Otherwise, the process proceeds to act 1112.

At act 1112, a prior adjustment to the flow rate of the first well may be considered to determine whether the prior adjustment opened or closed the valve of the first well. After determining whether the prior adjustment opened or closed the valve at act 1112, it is determined, at acts 1114-1116, whether methane concentration increased as a result of the prior adjustment. At acts 1112-1124, if the prior adjustment resulted in an increase to methane concentration of the landfill gas collected from the first well, the prior adjustment may be repeated by opening or closing the valve again. When the prior adjustment did not result in an increase to methane concentration of the landfill gas being collected from the first well, the prior adjustment is reversed by closing the valve when the prior adjustment opened the valve or opening the valve when the prior adjustment closed the valve. Although the illustrated embodiment gives a specific example where the process begins by using oxygen concentration to control extraction of landfill gas, then balance gas concentration, and using methane concentration last, other orders of process 1100 are possible. In addition, in some embodiments, one or more other characteristics of the landfill gas collected from the plurality of wells may additionally or alternatively be used to control landfill gas extraction.

Hybrid Control Systems and Methods

Figure 13:
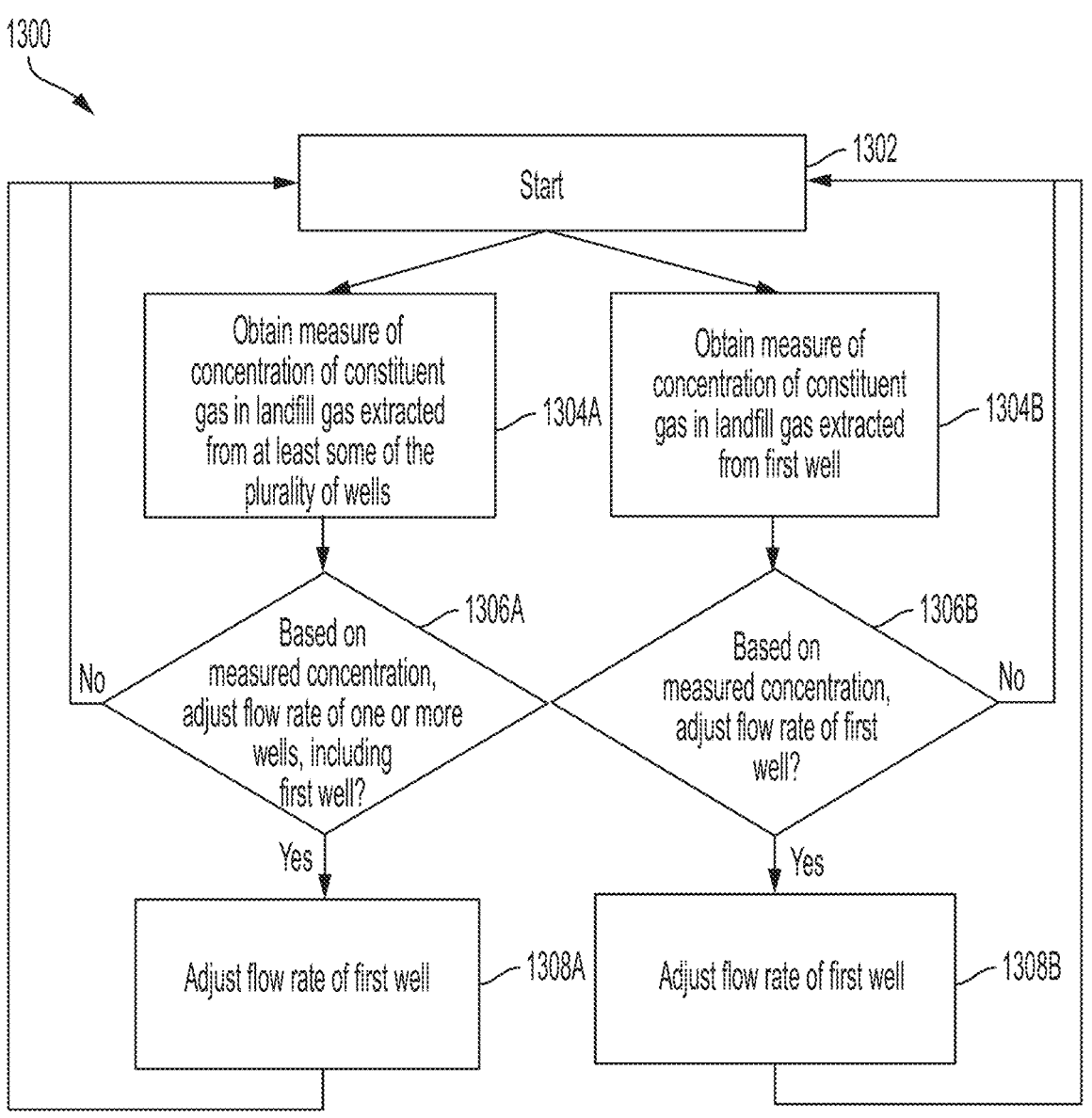
FIG. 13 is a flowchart of another illustrative process for controlling extraction of landfill gas through a gas extraction system, according to some embodiments.

Site-level and well-level methods for controlling extraction of landfill gas have been described herein. In some embodiments, both site-level and well-level control methods may be used to control extraction of landfill gas from one or more wells. For example, FIG. 13 illustrates an example of a hybrid control process 1300 for performing both site-level and well-level control of one or more wells.

Process 1300 begins at act 1302. From act 1302, the process concurrently proceeds to acts 1304A-1308A to perform a global control method as well as acts 1304B-1308B to perform a global control method. In this way, the global and local control methods may each cause respective adjustments to be applied to a particular a local well. For example, a first adjustment may be made to a local well as a result of the global control method, and a second adjustment may be made to the local well as a result of the local control method. In some embodiments, the first and second adjustments may be performed at different times and separately from one another. In other embodiments, the first and second adjustments may be performed simultaneously by determining a net adjustment from the first and second adjustments and applying the net adjustments to the local well.

In some embodiments, the global and local methods may be performed at different frequencies, as described herein. For example, the local control method may be performed more frequently than the global control method. As such, in some embodiments, in a given time period, the local control method may make more adjustments to a local well than the global control method makes. In some embodiments, the local control method may make multiple adjustments to a local well over a period of time where the global control method makes a single adjustment to the local well in the same period of time.

Referring to the global control method, at act 1304A, a measure of a concentration of a constituent gas (e.g., oxygen, methane, nitrogen) in landfill gas extracted from at least some of a plurality of wells is obtained by a multi-well controller. The at least some of the plurality of wells may include at least a first and second well. At act 1306A, the measure of the constituent gas concentration obtained at act 1304A is used, by the multi-well controller, to determine whether to adjust a flow rate of one or more wells of the plurality of wells, including the first well. For example, act 1306A may comprise any of the global control methods described herein for site-level control of landfill gas extraction. When it is determined, at act 1306A, to make an adjustment to the flow rate of the first well, the process may proceed to act 1308 where the multi-well controller and/or one or more local controllers adjust the flow rate of landfill gas being extracted from the first well. Otherwise, the process returns through the no branch to act 1302. After adjusting the flow rate of the first well at act 1308A, the process returns to act 1302, or alternatively, the process may end. Although acts 1306A-1308A are described with reference to a first well of the plurality of wells, it should be appreciated that the method may be performed for any number of the plurality of wells (e.g., each of the plurality of wells, a subset of the plurality of wells, including the second well).

Referring to the local control method, at act 1304B, a measure of a concentration of a constituent gas (e.g., oxygen, methane, balance gas) in landfill gas extracted from the first well is obtained by a local level controller. At act 1306B, the measure of the constituent gas concentration obtained at act 1304B is used by the local level controller to determine whether to adjust a flow rate of the first well. For example, act 1306B may comprise any of the local control methods described herein for well-level control of landfill gas extraction. When the local level controller determines, at act 1306B, to adjust the flow rate of the landfill gas being extracted from the first well, the process proceeds to act 1308B where the local level controller adjusts the flow rate of the landfill gas being extracted from the first well. Otherwise, the process returns through the no branch to act 1302. After adjusting the flow rate of the first well at act 1308B, the process returns to act 1302, or alternatively, may end. It should be appreciated that the global control method described in acts 1304B-1308 may be performed for one or more other wells.

Thus, the process 1300 describes a hybrid control scheme which results in respective adjustments being made to a first well as a product of both site-level and well-level control. As described herein, the global control method may be performed at a first frequency and the local level control process may be performed at a second frequency. In some embodiments, the first frequency is less than the second frequency. In some embodiments, the first frequency comprises no more than once a month, once a week, once every three days, once a day, or any other suitable frequency. In some embodiments, the second frequency comprises at least once a day, at least once each hour, at least once every 15 minutes, at least once every 10 minutes, or any other suitable frequency.

The local level control method may provide fine-tuning of a valve position (and consequently a flow rate) of the first well while the global control method may provide for larger scale adjustments to valve position. For example, in some embodiments, valve adjustments performed by the global control method may comprise changing the degree to which a valve is open by a greater amount than valve adjustments performed by the local control method.

The success or failure of any of the control schemes described herein may be assessed in any suitable way. In some embodiments, attributes of the landfill gas may be monitored over a period of time, and a determination may be made as to whether the monitored values comply with the control scheme. For example, to determine whether a specified quantity of methane has been extracted from the landfill in a specified time period, the concentration of methane in the extracted landfill gas and the flow rate of the extracted landfill gas may be monitored during the time period, and quantity of extracted methane may be determined based on the monitored methane concentration levels and gas flow rates. In some embodiments, attributes of the landfill gas may be measured at a specified time, and a determination may be made as to whether the measured values comply with the control scheme. For example, to determine whether the flow rate of extracted landfill gas matches a target flow rate, the flow rate of extracted landfill gas may be measured at some time and compared to the target flow rate.

In some embodiments, the control system 500 may be used to monitor the effect of other treatments besides just the setting of the control valve (e.g., monitoring effects of microbial treatment, leachate recirculation, watering out/pumping of the wells, adding iron, $H_2S$ abatement, etc.).

Additional Control Aspects

Methods for Scaling Valve Adjustments

Figure 14:
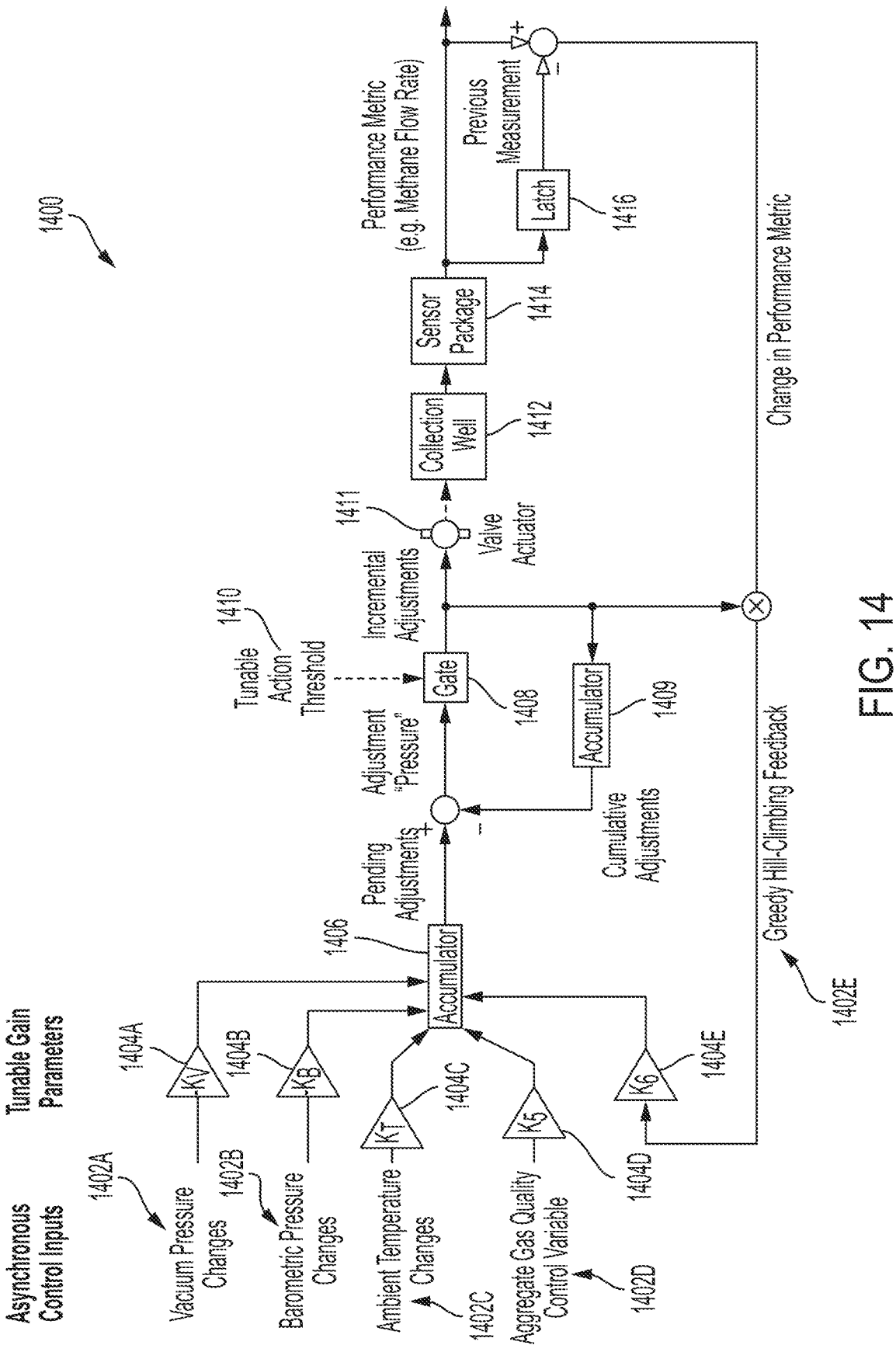
FIG. 14 is a block diagram of an illustrative control system for locally controlling flow of landfill gas at a gas extraction well, according to some embodiments.

FIG. 14 shows a block diagram of a control system 1400 for locally controlling flow of landfill gas at a gas extraction well. In some embodiments, the control system 1400 may be implemented, in part, by one or more local controllers 610A-C described above with reference to FIG. 6.

In the illustrated embodiment, the system 1400 obtains control variables 1402A-E and applies respective gains 1404A-E to the control variables 1402A-E to obtain respective adjustments for each of the control variables. The control variables 1402A-E may be used as control inputs by the system 1400. The system 1400 includes an accumulator 1406 which combines and accumulates the adjustments. The system 1400 includes a gate 1408, which prevents application of the adjustments until a threshold adjustment pressure 1410 is reached. The threshold pressure 1410 may be a minimum magnitude of adjustment required to trigger application of the adjustment by the system 1400. Once the pending adjustments reach the threshold 1410, the pending adjustments are applied to a valve actuator 1411 which then causes the position of a valve disposed in piping of a collection well 1412 to change.

In some embodiments, an adjustment to a valve may be specified in terms of a degree to which a valve is to be opened or closed. For example, the adjustment may be a percentage change in position of the valve (e.g., 10% more open or closed). In another example, the adjustment may be an amount by which the valve position is to be changed (e.g., +/−5 degrees). In some embodiments, an adjustment may be an absolute position of the valve. For example, the adjustment may be a percentage specifying a particular position of the valve (e.g., 0-100% open). In another example, the adjustment may be a degree value specifying an absolute position of the valve (e.g., 0-180 degrees).

In the illustrated embodiment, the system 1400 includes a sensor package 1414 to obtain measurement(s) of one or more performance metrics. The system 1400 includes a latch 1416 for storing a previous measurement of the performance metric(s). The system 1400 compares a measurement of the performance metric(s) taken after application of an adjustment to a measurement of the performance metric(s) taken prior to the application of the adjustment. The result of the comparison is used as feedback control input 1402E. In some embodiments, a performance metric may be an energy content of landfill gas being extracted from the collection well 1412, a concentration of methane in the landfill gas being extracted from the collection well 1412, and/or a flow rate of landfill gas being extracted from the collection well 1412.

In the illustrated embodiment, the system 1400 includes a second accumulator 1409 which accumulates adjustments that have been applied to the valve actuator 1411. The applied adjustments that have been accumulated by the accumulator 1409 are subtracted from pending adjustments such that the adjustments may be applied in discrete increments. For example, if a pending adjustment of 5 degrees meets the action threshold 1410, and is applied to the valve actuator 1411, the 5 degree adjustment that is applied to the valve actuator 1411 is tracked by the accumulator 1409. In a subsequent control cycle, the pending adjustment value may remain at 5 degrees. The previous 5 degree adjustment tracked by the accumulator 1409 is subtracted from the pending adjustment value such that the adjustment pressure is 0. Accordingly, no additional adjustment is applied to the valve actuator 1411. This allows pending adjustments to be applied in discrete increments such that an effect of an applied adjustment can be measured by the sensor package 1414.

In some embodiments, the system 1400 may be configured to use a measured change in vacuum pressure 1402A as a control input. The change in vacuum pressure 1402A may indicate a change in a pressure differential between a gas output and the landfill. The pressure differential causes landfill gas to flow from the landfill to the gas output through collection well 1412. The system 1400 may apply a tunable gain parameter ($-K_V$) 1404A to the measured change in vacuum pressure. If the pressure differential decreases by a certain amount, the system may obtain an adjustment to reduce a flow rate of landfill gas being extracted from the collection well 1412. For example, the adjustment may be one that results in closing the valve further. If the pressure differential increases by a certain amount, the system may obtain an adjustment to increase a flow rate of landfill gas being extracted from the collection well 1412. For example, the adjustment may be opening the valve further.

In some embodiments, the system 1400 may be configured to use a measured change in barometric pressure 1402B as a control input. The change in barometric pressure may be measured over a period of time. An increase in barometric pressure over the period of time may increase a pressure differential between the landfill and air outside of the landfill. As a result, more air may permeate into the landfill and affect composition of landfill gas being extracted from the landfill. In some instances, this may result in decreased concentration of methane in the land fill gas which results in the landfill gas having a lower energy content. The system may apply a gain parameter ($-K_B$) 1404B to the measured change in barometric pressure. If there is a positive change in barometric pressure, the system may determine a corresponding adjustment to reduce a flow rate of landfill gas being extracted from the well 1412 to mitigate effects of the rise in pressure. If there is a negative change in barometric pressure, the system may determine a corresponding adjustment to increase a flow rate of landfill gas being extracted from the well 1412.

In some embodiments, the system 1400 may be configured to continuously obtain measurements of the barometric pressure. In some embodiments, the system 1400 may be configured to obtain a measurement every 1 minute, 2 minutes, 3 minutes, 4 minutes, 5 minutes, 6 minutes, 7 minutes, 8 minutes, 9 minutes, or 10 minutes. In some embodiments, the system 1400 may be configured to calculate a running average rate of change of barometric pressure. In some embodiments, the system 1400 may be configured to determine whether the magnitude of the calculated rate of change of the barometric pressure is greater than a threshold rate of change. In response to determining that the magnitude of the calculated rate of change is greater than the threshold rate of change, the system 1400 may trigger a response to the change in barometric pressure. If there is a positive change in the rate of change of the barometric pressure, the system may determine a corresponding adjustment to reduce a flow rate of landfill gas being extracted from the well 1412 to mitigate effects of the rise in pressure. If there is a negative change in the rate of change of the barometric pressure, the system may determine a corresponding adjustment to increase a flow rate of landfill gas being extracted from the well 1412.

In some embodiments, the threshold rate of change may be 0.05 mbar/hour, 0.1 mbar/hour, 0.15 mbar/hour, 0.2 mbar/hour, 0.25 mbar/hour, 0.3 mbar/hour, 0.35 mbar/hour, 0.4 mbar/hour, 0.5 mbar/hour 0.55 mbar/hour, 0.6 mbar/hour, 0.65 mbar/hour, 0.7 mbar/hour, 0.75 mbar/hour, 0.8 mbar/hour, 0.85 mbar/hour, 0.9 mbar/hour, 0.95 mbar/hour, or 1 mbar/hour.

In some embodiments, the system 1400 may be configured to use a measured change in ambient temperature 1402C as a control input. When an ambient temperature outside of the landfill decreases by a certain amount, the permeability of a covering placed over the landfill may increase. As a result, additional air from the atmosphere around the landfill may enter the landfill and affect composition of the landfill gas being extracted. For example, a concentration of methane in the landfill gas being extracted may be reduced, which results in reduced energy content of the landfill gas being extracted. The system 1400 may be configured to apply a gain parameter $(K_T)$ 1404C to the measured change in ambient temperature. If the ambient temperature decreases over a period of time, the system may obtain a corresponding adjustment that reduces a flow rate of landfill gas from the well 1412 to mitigate effects of the drop in temperature. If the ambient temperature increases, the system may obtain a corresponding adjustment to increase a flow rate of landfill gas being extracted from the well 1412.

In some embodiments, the system 1400 may be configured to use an aggregate gas quality control variable 1402D. The aggregate gas quality control variable may be obtained from a multi-well controller that determines global adjustments to be applied to multiple gas extraction wells at a landfill. The aggregate gas quality control variable may be determined as described below with reference to FIG. 18. The system 1400 may apply a gain parameter $(K_S)$ 1404D to the aggregate gas quality control variable 1402D. The system may determine an adjustment to increase the flow rate of landfill gas being extracted from the well 1412 in response to more positive values of the control variable, and an adjustment to decrease the flow rate of landfill gas being extracted from the well 1412 in response to more negative values of the control variable.

In some embodiments, the system 1400 may be configured to use a feedback control input 1402E determined based on a measured effect of one or more applied adjustments. In some embodiments, the system may be configured to implement a greedy hill climbing feedback input. The system 1400 may multiply a measured effect of the performance metric(s) of an applied adjustment by the applied adjustment. If the applied adjustment resulted in a negative effect on the performance, the feedback 1404E will be an opposite of the applied adjustment. For example, if an applied adjustment of +1 degrees resulted in a −2% decrease in concentration of methane, the value of the feedback input 1402E will be −2 which is in the opposite direction of the applied adjustment. Conversely, if the applied adjustment resulted in a positive effect on the performance, the feedback 1404E will continue in a direction of the applied adjustment. For example, if an applied adjustment of +1 degrees results in a +2% increase in concentration of methane, the value of the feedback input 1402E will be 2. The system 1400 may apply a gain parameter $(K_G)$ 1404E to the feedback 1402E.

In some embodiments, the system 1400 may be configured to use a predicted change in barometric pressure as a control input. An increase in barometric pressure may affect landfill gas being extracted from the well 1412. Using predicted changes in barometric pressure may allow the system 1400 to bias a flow of landfill gas to mitigate effects of future actual changes in barometric pressure on landfill gas being extracted from the well 1412. The system 1400 may apply a gain parameter to a predicted change in barometric pressure. If the system obtains a predicted increase in barometric pressure, the system may obtain a corresponding adjustment to decrease a flow rate of landfill gas being extracted from the well 1412. If the system obtains a predicted decrease in barometric pressure, the system may obtain a corresponding adjustment to increase a flow rate of landfill gas being extracted from the well 1412.

In some embodiments, the system 1400 may be configured to use a predicted change in ambient temperature as a control input. As described above, a change in ambient temperature may affect landfill gas being extracted from the well 1412. Using predicted changes in ambient temperature may allow the system 1400 to bias the flow of landfill gas to mitigate effects of future changes in the ambient temperature on the landfill gas being extracted from the well 1412. The system 1400 may apply a gain parameter to a predicted change in ambient temperature. If the system obtains a predicted increase in ambient temperature pressure, the system may obtain a corresponding adjustment to increase a flow rate of landfill gas being extracted from the well 1412. If the system obtains a predicted decrease in ambient temperature, the system may obtain a corresponding adjustment to decrease a flow rate of landfill gas being extracted from the well 1412.

In some embodiments, the system 1400 may use other control inputs in addition to or instead of those illustrated in FIG. 14. In some embodiments, the system 1400 may be configured to use a value indicating a measured current precipitation and/or predicted precipitation outside of the landfill as a control input. A change in precipitation may affect landfill gas being extracted from the landfill. For example, the value may indicate a measured amount of precipitation (e.g., inches) and/or a type of precipitation (e.g., snow, rain, hail). Some embodiments are not limited to any particular set of control inputs. Some embodiments may use any combination of control inputs described herein.

In some embodiments, the system 1400 may be configured to obtain values of one or more control inputs using local sensors. For example, values of control inputs 1402A-C may be obtained using sensors that are part of the control system. In some embodiments, the system 1400 may be configured to receive values of one or more control inputs from an external system. For example, the system 1400 may access barometric pressure changes, ambient temperature changes, forecasted barometric pressure changes, and forecasted ambient temperature changes from a computer separate from the system 1400.

In some embodiments, the gain parameters used by the system may be tunable. Different wells may react differently to various changes. The gain parameters may be tuned based on unique characteristics of the well 1412. For example, a constituent gas concentration (such as methane concentration, for example) in landfill gas being extracted from a first well may be more sensitive to changes in flow rate than landfill gas being extracted from a second well. In particular, the constituent gas concentration may increase or decrease by a larger amount in response to a change in flow rate as compared to a constituent gas concentration of landfill gas at other wells. In some embodiments, the sensitivity of the landfill gas composition to a change in flow rate for a particular well may be based, at least in part, on the ground cover in a region of the well (e.g., a depth of the ground cover, a density of the ground cover). Each well may have a set of gain parameters that have been tuned for the well. In some embodiments, gain parameters at each well may be tuned to maximize performance at the well. In some embodiments, gain parameters may be tuned such that effects of control inputs are uniform across different wells. In some embodiments, the gain parameters may be tuned manually or automatically.

In some embodiments, the system 1400 may utilize different gains for controlling the opening and closing of the valve. For example, a first set of one or more gains may be used for controlling opening of the valve and a second set of one or more gains may be used for controlling closing of the valve, with the first and second sets of gains being different from one another. For example, different vacuum pressure change gains $K_V$ may be used for controlling opening and closing a valve. Additionally or alternatively, different barometric pressure change gains $K_B$ may be used for controlling opening and closing a valve. Additionally or alternatively, different ambient temperature change gains $K_T$ may be used for controlling opening and closing a valve. Additionally or alternatively, different ambient temperature change gains $K_T$ may be used for controlling opening and closing a valve. Additionally or alternatively, different aggregate gas quality control gains $K_S$ may be used for controlling opening and closing a valve. Additionally or alternatively, different feedback gains $K_G$ may be used for controlling opening and closing a valve. Additionally or alternatively, different action thresholds 1410 may be used for controlling opening and closing a valve. Thus, it should be appreciated that different gains for any one or more of the gains $K_V$, $K_B$, $K_S$, $K_T$, $K_G$ and action thresholds may be used for controlling opening and closing of the valves.

In some embodiments, one or more of the gains for a valve may be based on how quickly the composition of gas flowing through a valve from a well changes as a result of a valve adjustment. When the composition of gas changes more rapidly in response to a valve adjustment operation (e.g., closing or opening), then the gain for that valve operation may be set to a lower value. When the composition of gas changes more slowly in response to a valve adjustment operation, then the gain for that valve operation may set to a higher value. For example, suppose that the composition of gas flowing through a valve from a well changes more rapidly in response to opening of a valve than to closing of the valve. In that situation, one or more gains of the valve may be set lower (e.g., a first gain) for the opening adjustment than for the closing adjustment (e.g., a second gain larger than the first gain).

In some embodiments, the system 1400 may include a gate 1408 that allows application of adjustments that meet a threshold 1410 level of adjustment. In some embodiments, the threshold 1410 may be tuned to adjust sensitivity of the system 1400 to adjustments. For example, a lower threshold 1410 will allow adjustments to be applied more frequently, and will allow application of finer adjustments. A higher threshold 1410 will limit frequency of adjustments applied, and will limit application to coarser adjustments. In some embodiments, the threshold 1410 may be tuned to balance stability of the system 1400 with precision of control. In some embodiments, the controller may have limited power resources, and the gate 1408 may moderate a frequency of application of adjustments to limit use of the power. For example, a controller may be powered by a solar panel which stores energy. The gate 1408 may limit application of adjustments to conserve the stored energy.

In some embodiments, the threshold 1410 may be a minimum percentage of change. For example, the threshold may be a magnitude of 1%, 2%, 3%, 5%, 10%, 15%, or 20%. In some embodiments, the threshold may be a particular number of degrees. For example, the threshold may be 1 degree, 2, 3, 5, 10, 15, 20, or 25 degrees.

In some embodiments, the system 1400 may be configured to maintain one or more limits of the position of the valve. The limit(s) may be referred to as "guard rails." The system 1400 may be configured to prevent adjustments to the position of the valve beyond the limit(s). In some embodiments, the system 1400 may prevent the valve from opening beyond a first limit and/or closing beyond a second limit. The limit may be a particular position of the valve. For example, the system 1400 may prevent the valve from opening beyond a position of 80 degrees. In another example, the system 100 may prevent the valve from closing more than a position of 5 degrees. In yet another example, the system 1400 may prevent the valve from opening beyond a position of 90% open. In yet another example, the system 1400 may not allow the valve to close beyond a position of 10% open.

In some embodiments, the system 1400 may be configured to maintain a threshold concentration of one or more of the gases that make up the landfill gas. In some embodiments, the system 1400 may be configured to determine if a measured concentration of oxygen in the landfill gas is above a maximum oxygen concentration. If the system 1400 determines that the measured concentration of oxygen is above the maximum oxygen concentration, the system 1400 may restrict a flow of landfill gas. For example, the system 1400 may prevent adjustments that further open the valve. In another example, the system 1400 may close the valve by a certain amount. In some embodiments, the system 1400 may be configured to determine if a measured concentration of nitrogen in the landfill gas is above a maximum nitrogen concentration. If the system 1400 determines that the measured concentration of nitrogen is above the maximum nitrogen concentration, the system 1400 may restrict a flow of landfill gas. For example, the system 1400 may prevent adjustments that further open the valve. In another example, the system 1400 may close the valve by a certain amount. In some embodiments, the system 1400 may be configured to determine if a measured concentration of methane in the landfill gas is above a maximum methane concentration. If the system 1400 determines that the measured concentration of methane is above the maximum methane concentration, the system 1400 may restrict a flow of landfill gas. For example, the system 1400 may prevent adjustments that further open the valve. In another example, the system 1400 may close the valve by a certain amount.

Proportional Response

Some of the automated control techniques described herein involve adjusting the degree to which one or more valves are open or closed based on the difference between a measured value of a quantity (e.g., BTU, energy content in gas, percentage of a particular type of gas such as methane or oxygen or nitrogen in the landfill gas, etc.) and a target value for that quantity. In some embodiments, when it is determined that a valve is to be closed or opened, the valve is controlled to close or open by a fixed amount. In some embodiments, when it is determined that a valve is to be closed or opened, the valve is controlled to close or open by an amount that depends on the difference between the measured value of the quantity and the target value for that quantity. For example, when closing the valve serves to decrease the difference between the measured value and the target value of a quantity, then the valve may be closed to a greater degree when the difference between the measured and target values is large than when that difference is small. In this way, a valve may be closed and opened by an amount proportional to the difference between the measured and target value of the quantity used for control. As a further example, in some embodiments, when the measured gas composition at the plant is farther away from the target gas composition, the batch valve open/close command may be greater (as reflected by the larger gains utilized).

Automated Shutoff

In some embodiments, automated control of one or multiple valves in a landfill gas extraction system may be stopped in response to receiving one or more unexpected measurements from one or more sensors parts of the automated control system. In this way, valve adjustments determined by any of the automated control techniques described herein are not determined based on erroneous sensor readings, especially erroneous sensor readings at the power plant.

For example, in some embodiments, automated control may be stopped in response to obtaining gas composition measurement (e.g., from power plant equipment) outside of one or more specified ranges for constituent gasses. As another example, in some embodiments, automated control may be stopped in response to obtaining a BTU measurement (e.g., from power plant equipment) outside of a specified BTU range. For example, automated control may be stopped in response to obtaining a BTU measurement outside of the range of 940-1000 BTUs.

After automated control is stopped, it may be restarted in any suitable way. For example, in some embodiments, the automated control may be restarted after a threshold amount of time has elapsed. As another example, in some embodiments, the automated control may be restarted in response to updated measurements falling within the specified ranges. For instance, if automation control was stopped in response to a measurement of a quantity falling outside of a specified range of "normal" values for that quantity, automated control may be restarted when a subsequent measurement of that same quantity is within the specified range. As yet another example, in some embodiments, automated control may be resumed in response to user input (e.g., provided through a computer interface, such as a graphical computer interface) indicating that the automated control is to be resumed.

Current and Predicted Measurements

The automated control techniques described herein, in some embodiments, control the degree to which one or more valves are open based on one or more sensor measurements (e.g., one or more measurements of gas composition, flow rate, ambient temperature, barometric pressure, BTU measurements at the power plant, etc.). The inventors have recognized that, while such valve adjustments can be effective, in some embodiments the impact of the adjustments takes time to take effect. In other words, the overall response time in the system to a valve adjustment may be slower than desired.

The inventors have recognized that, in some circumstances, the response time to valve adjustments may be reduced, by using a predicted value of a quantity to control the valves instead of a currently measured value of that same quantity. By way of example, suppose that valve control is being performed, in part, based on the percentage of methane in landfill gas. The first measurement may indicate that the percentage of methane is 46%. An hour later, the second measurement may indicate that the percentage of methane is 45%. Another hour later, the third measurement may indicate that the percentage of methane is 44%. A valve adjustment could be made, each hour, based on these measurements. However, by using the 46% and 45% measurements, it may be possible to predict that, in an hour, the predicted value of methane concentration would be 44%. If such a prediction could be made, then the automated control techniques could determine the degree(s) to which to close/open one or more respective values based on the predicted value (i.e., 44%) rather than the measured values of 46% and 45%, and to do so before the 44% value would be measured (an hour later) thereby reducing the overall time needed to control the gas extraction system to a target state.

Accordingly, in some embodiments, one or more (e.g., two, three, etc.) measured values of a quantity (e.g., one or more measurements of gas composition, flow rate, ambient temperature, barometric pressure, BTU measurements at the power plant, etc.) may be used to predict a value that quantity is likely to take during a specified time period in the future (e.g., 1, 5, 10, 15, 20, 25, 30, 35, 40, 45, 50, 55, 60 minutes, 2 hours, 3 hours, between 1 and 5 minutes, between 10 and 20 minutes, between 30 minutes and 2 hours, or any range within these ranges). In some embodiments, two measurements may be used to obtain a predicted value using linear projection (e.g., measure the slope of the line defined by the two measurements and use the measured slope to predict a third value). In embodiments, where a larger number of measurements is used (i.e., three or more), a higher order polynomial projection may be performed.

It should be appreciated that any of the control techniques described herein may use predicted values of measurements for any of the quantities utilized for control (e.g., gas composition, flow rate, ambient temperature, barometric pressure, BTU measurements at the power plant, etc.). In some embodiments, predicted values may be used for all the quantities utilized for control. In some embodiments, one or more predicted values and one or more measured values may be utilized for control. In some embodiments, prediction may not be employed, and only measured values may be used.

Example Computing System

Figure 15:
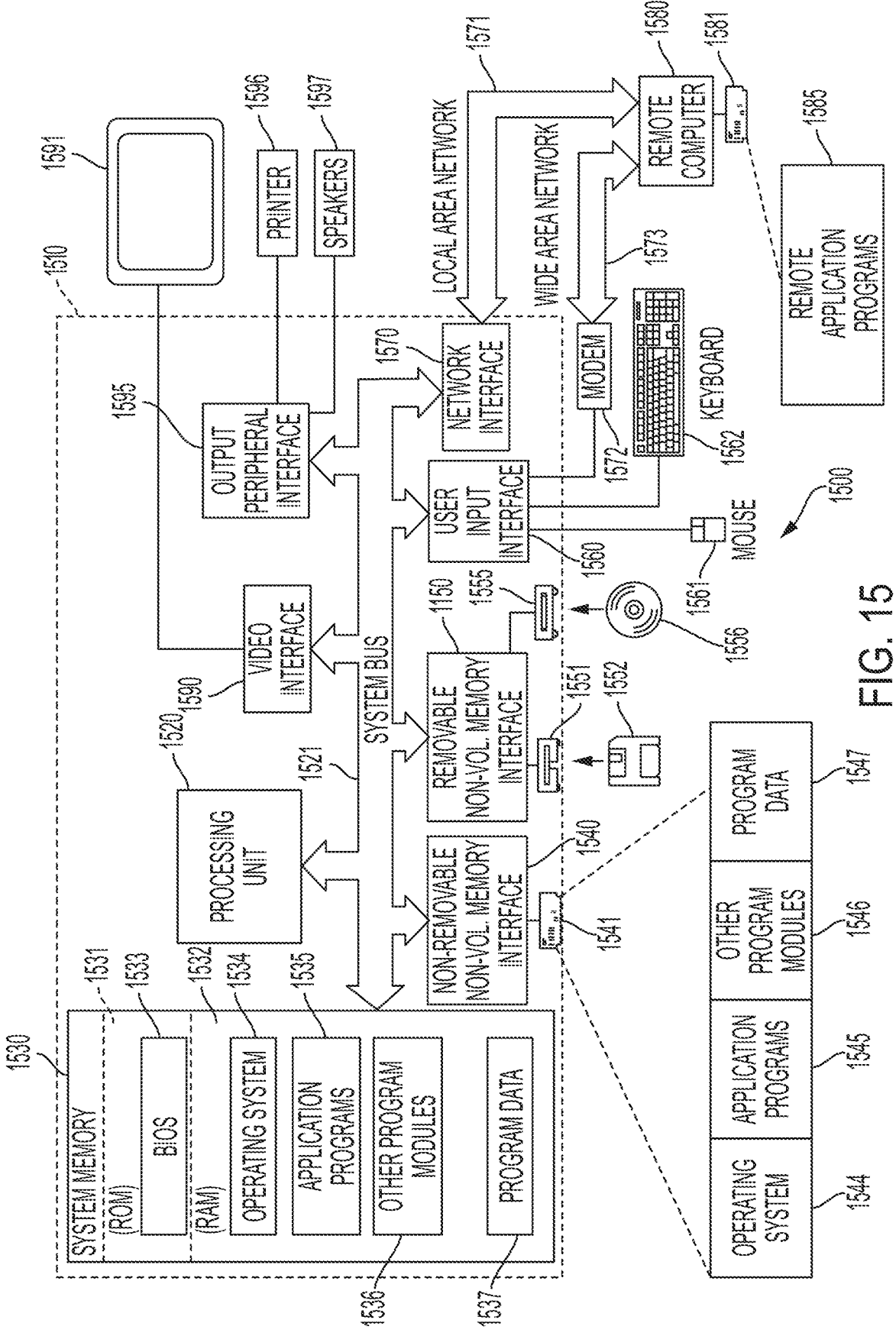
FIG. 15 is a block diagram of an exemplary computer system in which aspects of the present disclosure may be implemented, according to some embodiments.

FIG. 15 illustrates an example of a suitable computing system environment 1500 on which techniques disclosed herein may be implemented. In some embodiments, portions of a landfill gas extraction control system may be implemented in a computing system environment. For example, in some embodiments, Device Manager 502, Controller Module 504, User Interface 508, and/or Database 510 may be implemented in a computing system environment. In some embodiments, aspects of one or more techniques described herein may be implemented in a computing system environment.

The computing system environment 1500 is only one example of a suitable computing environment and is not intended to suggest any limitation as to the scope of use or functionality of the devices and techniques disclosed herein. Neither should the computing environment 1500 be interpreted as having any dependency or requirement relating to any one or combination of components illustrated in the exemplary operating environment 1500.

The techniques disclosed herein are operational with numerous other general purpose or special purpose computing system environments or configurations. Examples of well-known computing systems, environments, and/or configurations that may be suitable for use with techniques disclosed herein include, but are not limited to, personal computers, server computers, hand-held devices (e.g., smart phones, tablet computers, or mobile phones), laptop devices, multiprocessor systems, microprocessor-based systems, set top boxes, programmable consumer electronics, network PCs, minicomputers, mainframe computers, distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The technology described herein may also be practiced in distributed computing environments where tasks are performed by remote processing devices that are linked through a communications network. In a distributed computing environment, program modules may be located in both local and remote computer storage media including memory storage devices.

With reference to FIG. 15, an exemplary system for implementing techniques described herein includes a general purpose computing device in the form of a computer 1510. Components of computer 1510 may include, but are not limited to, a processing unit 1520, a system memory 1530, and a system bus 1521 that couples various system components including the system memory to the processing unit 1520. The system bus 1521 may be any of several types of bus structures including a memory bus or memory controller, a peripheral bus, and/or a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 1510 typically includes a variety of computer readable media. Computer readable media can be any available media that can be accessed by computer 1510 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 1510. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 1530 includes computer storage media in the form of volatile and/or nonvolatile memory such as read only memory (ROM) 1531 and random access memory (RAM) 1532. A basic input/output system 1533 (BIOS), containing the basic routines that help to transfer information between elements within computer 1510, such as during start-up, is typically stored in ROM 1531. RAM 1532 typically contains data and/or program modules that are immediately accessible to and/or presently being operated on by processing unit 1520. By way of example, and not limitation, FIG. 15 illustrates operating system 1534, application programs 1535, other program modules 1536, and program data 1537.

The computer 1510 may also include other removable/non-removable, volatile/nonvolatile computer storage media. By way of example only, FIG. 15 illustrates a hard disk drive 1541 that reads from or writes to non-removable, nonvolatile magnetic media, a magnetic disk drive 1551 that reads from or writes to a removable, nonvolatile magnetic disk 1552, and an optical disk drive 1555 that reads from or writes to a removable, nonvolatile optical disk 1556 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1541 is typically connected to the system bus 1521 through a non-removable memory interface such as interface 1540, and magnetic disk drive 1551 and optical disk drive 1555 are typically connected to the system bus 1521 by a removable memory interface, such as interface 1550.

The drives and their associated computer storage media described above and illustrated in FIG. 15, provide storage of computer readable instructions, data structures, program modules and other data for the computer 1510. In FIG. 15, for example, hard disk drive 1541 is illustrated as storing operating system 1544, application programs 1545, other program modules 1546, and program data 1547. Note that these components can either be the same as or different from operating system 1534, application programs 1535, other program modules 1536, and program data 1537. Operating system 1544, application programs 1545, other program modules 1546, and program data 1547 are given different numbers here to illustrate that, at a minimum, they are different copies. A user may enter commands and information into the computer 1510 through input devices such as a keyboard 1562 and pointing device 1561, commonly referred to as a mouse, trackball or touch pad. Other input devices (not shown) may include a microphone, joystick, game pad, satellite dish, scanner, or the like. These and other input devices are often connected to the processing unit 1520 through a user input interface 1560 that is coupled to the system bus, but may be connected by other interface and bus structures, such as a parallel port, game port or a universal serial bus (USB). A monitor 1591 or other type of display device is also connected to the system bus 1521 via an interface, such as a video interface 1590. In addition to the monitor, computers may also include other peripheral output devices such as speakers 1597 and printer 1596, which may be connected through an output peripheral interface 1595.

The computer 1510 may operate in a networked environment using logical connections to one or more remote computers, such as a remote computer 1580. The remote computer 1580 may be a personal computer, a server, a router, a network PC, a peer device or other common network node, and typically includes many or all of the elements described above relative to the computer 1510, although only a memory storage device 1581 has been illustrated in FIG. 15. The logical connections depicted in FIG. 15 include a local area network (LAN) 1571 and a wide area network (WAN) 1573, but may also include other networks. Such networking environments are commonplace in offices, enterprise-wide computer networks, intranets and the Internet.

When used in a LAN networking environment, the computer 1510 is connected to the LAN 1571 through a network interface or adapter 1570. When used in a WAN networking environment, the computer 1510 typically includes a modem 1572 or other means for establishing communications over the WAN 1573, such as the Internet. The modem 1572, which may be internal or external, may be connected to the system bus 1521 via the user input interface 1560, or other appropriate mechanism. In a networked environment, program modules depicted relative to the computer 1510, or portions thereof, may be stored in the remote memory storage device. By way of example, and not limitation, FIG. 15 illustrates remote application programs 1585 as residing on memory device 1581. It will be appreciated that the network connections shown are exemplary and other means of establishing a communications link between the computers may be used.

Conclusion

Embodiments of the above-described techniques can be implemented in any of numerous ways. For example, the embodiments may be implemented using hardware, software or a combination thereof. When implemented in software, the software code can be executed on any suitable processor or collection of processors, whether provided in a single computer or distributed among multiple computers. In some embodiments, the functions performed by an In Situ Control Mechanism 106 and/or a Controller 204 may be implemented as software executed on one or more processors.

Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the technology described herein may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the technology described herein. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present technology as described above. As used herein, the term "computer-readable storage medium" encompasses only a computer-readable medium that can be considered to be a manufacture (i.e., article of manufacture) or a machine. Alternatively or additionally, the technology described herein may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of technology described herein. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present technology may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the technology described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various events/acts are described herein as occurring or being performed at a specified time. One of ordinary skill in the art would understand that such events/acts may occur or be performed at approximately the specified time.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately," "substantially," and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of the technology, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

What is claimed is:

1. A method for controlling extraction of landfill gas from a landfill, the landfill comprising a plurality of wells coupled to an aggregate gas output, the method comprising:
performing, with at least one controller:
obtaining, using at least one sensor disposed at the aggregate gas output, a measure of a first characteristic of landfill gas collected from at least some of the plurality of wells;
obtaining, using at least one second sensor configured to measure a concentration of a constituent gas in landfill gas collected from a first well of the plurality of wells, a measure of a second characteristic of the landfill gas collected from the first well; and
when it is determined that the measure of the first characteristic of the landfill gas collected from at least some of the plurality of wells is outside of a global range and the measure of the second characteristic of the landfill gas collected from the first well is outside of a local range, adjusting a flow rate of landfill gas being extracted from the first well, wherein:
the first characteristic comprises oxygen concentration and the second characteristic comprises oxygen concentration, or the first characteristic comprises nitrogen concentration and the second characteristic comprises balance gas concentration.

2. The method of claim 1, wherein an upper endpoint of the global range is 5% nitrogen or less.

3. The method of claim 1, wherein an upper endpoint of the local range is 1% oxygen or less.

4. The method of claim 1, wherein an upper endpoint of the local range is 5% balance gas or less.

5. A method for controlling extraction of landfill gas from a landfill, the landfill comprising a plurality of wells coupled to an aggregate gas output, the method comprising:
performing, with at least one controller:
determining, based on one or more measurements made by at least one sensor disposed at the aggregate gas output, whether to adjust a flow rate of landfill gas being extracted from one or more wells of the plurality of wells, the determining comprising:
obtaining, from the at least one sensor disposed at the aggregate gas output, a measure of a first characteristic of landfill gas collected from at least some of the plurality of wells;
determining that the first characteristic of the landfill gas collected from the at least some of the plurality of wells is outside of a global range for the first characteristic; and
determining to adjust the flow rate of landfill gas being extracted from the one or more wells of the plurality of wells when it is determined that the measure of first characteristic of the landfill gas collected from the at least some of the plurality of wells is outside the global range for the first characteristic;

when it is determined to adjust the flow rate of landfill gas being extracted from the one or more wells of the plurality of wells, selecting at least one of the one or more wells to adjust based on one or more measurements made by at least one second sensor, the selecting comprising:

determining that a measure of a second characteristic of landfill gas collected from a first well of the one or more wells is outside of a local range for the second characteristic; and when it is determined that the measure of the second characteristic of landfill gas collected from the first well is outside of the local range for the second characteristic, selecting the first well; and adjusting a flow rate of landfill gas being extracted from the selected at least one of the one or more wells including the first well, wherein:

the first characteristic comprises oxygen concentration and the second characteristic comprises oxygen concentration, or the first characteristic comprises nitrogen concentration and the second characteristic comprises balance gas concentration.

6. The method of claim 5, wherein the selecting further comprises:

determining that a measure of the second characteristic of landfill gas collected from a second well of the one or more wells is outside of the local range for the second characteristic;

when it is determined that the measure of the second characteristic of landfill gas collected from the second well is outside the local range for the second characteristic, selecting the second well; and wherein adjusting the flow rate of landfill gas being extracted from the selected at least one of the one or more wells includes adjusting the flow rate of landfill gas being extracted from the second well.

7. The method of claim 5, wherein an upper endpoint of the global range is 5% nitrogen or less.

8. The method of claim 5, wherein a lower endpoint of the global range is 0% nitrogen or more.

9. The method of claim 5, wherein an upper endpoint of the global range is 0.2% oxygen or less or less.

10. The method of claim 5, wherein an upper endpoint of the local range is 1% oxygen or less.

11. The method of claim 5, wherein adjusting the flow rate of landfill gas being extracted from the first well comprises changing a degree to which a valve of the first well is open.

12. The method of claim 5, further comprising:

determining a scaling factor by which to proportionally adjust a degree to which a valve of the first well is open, the scaling factor being based at least in part on a difference between a measure of the second characteristic of the landfill gas collected from the first well and a target value; and wherein adjusting the flow rate of landfill gas being extracted from the first well comprises adjusting the flow rate of the landfill gas being extracted from the first well according to the scaling factor.

13. The method of claim 5, further comprising:

determining a scaling factor by which to proportionally adjust a degree to which a valve of the first well is open, the scaling factor being based at least in part on at least one characteristic of the first well; and wherein adjusting the flow rate of landfill gas being extracted from the first well comprises adjusting the flow rate of the first well according to the scaling factor.

14. The method of claim 13, wherein the at least one characteristic of the first well comprises a sensitivity of a composition of the landfill gas being extracted from the first well to a change in flow rate.

15. A system for controlling extraction of landfill gas from a landfill, the landfill comprising a plurality of wells coupled to an aggregate gas output, the system comprising:

at least one controller configured to perform a method comprising:

determining, based on one or more measurements made by at least one sensor disposed at the aggregate gas output, whether to adjust a flow rate of landfill gas being extracted from one or more wells of the plurality of wells, the determining comprising:

obtaining, from the at least one sensor disposed at the aggregate gas output, a measure of a first characteristic of landfill gas collected from at least some of the plurality of wells;

determining that the measure of the first characteristic of the landfill gas collected from the at least some of the plurality of wells is outside of a global range for the first characteristic; and determining to adjust the flow rate of landfill gas being extracted from the one or more wells of the plurality of wells when it is determined that the measure of the first characteristic of the landfill gas collected from the at least some of the plurality of wells is outside the global range for the first characteristic;

when it is determined to adjust the flow rate of landfill gas being extracted from the one or more wells of the plurality of wells, selecting at least one of the one or more wells to adjust based on one or more measurements made by at least one second sensor, the selecting comprising:

determining that a measure of a second characteristic of landfill gas collected from a first well of the one or more wells is outside of a local range for the second characteristic; and when it is determined that the measure of the second characteristic of landfill gas collected from the first well is outside of the local range for the second characteristic, selecting the first well; and adjusting a flow rate of landfill gas being extracted from the selected at least one of the one or more wells including the first well, wherein:

the first characteristic comprises oxygen concentration and the second characteristic comprises oxygen concentration, or the first characteristic comprises nitrogen concentration and the second characteristic comprises balance gas concentration.

16. The system of claim 15, further comprising the at least one sensor disposed at the aggregate gas output.

17. The system of claim 15, further comprising the at least one second sensor.

18. A system for controlling extraction of landfill gas from a landfill, the landfill comprising a plurality of wells coupled to an aggregate gas output, the system comprising:

at least one controller configured to perform a method comprising:

obtaining, using at least one sensor disposed at the aggregate gas output, a measure of a first characteristic of landfill gas collected from at least some of the plurality of wells;

obtaining, using at least one second sensor configured to measure a concentration of a constituent gas in landfill gas collected from a first well of the plurality of wells, a measure of a second characteristic of landfill gas collected from the first well; and when it is determined that the measure of the first characteristic of the landfill gas collected from at least some of the plurality of wells is outside of a global range and the measure of second characteristic of the landfill gas collected from the first well is outside of a local range, adjusting a flow rate of landfill gas being extracted from the first well, wherein:

the first characteristic comprises oxygen concentration and the second characteristic comprises oxygen concentration, or the first characteristic comprises nitrogen concentration and the second characteristic comprises balance gas concentration.

19. The system of claim 18, further comprising the at least one sensor disposed at the aggregate gas output.

20. The system of claim 18, further comprising the at least one second sensor.

\* \* \* \* \*